US008862240B2

(12) United States Patent
Goetz et al.

(10) Patent No.: US 8,862,240 B2
(45) Date of Patent: Oct. 14, 2014

(54) AUTOMATED PROGRAMMING OF ELECTRICAL STIMULATION ELECTRODES USING POST-IMPLANT IMAGING

(75) Inventors: Steven M. Goetz, North Oaks, MN (US); Wende L. Dewing, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 676 days.

(21) Appl. No.: 12/359,261

(22) Filed: Jan. 23, 2009

(65) Prior Publication Data
US 2009/0198306 A1 Aug. 6, 2009

Related U.S. Application Data

(60) Provisional application No. 61/025,168, filed on Jan. 31, 2008, provisional application No. 61/025,158, filed on Jan. 31, 2008.

(51) Int. Cl.
| | | |
|---|---|---|
| *A61N 1/00* | (2006.01) | |
| *G06T 7/00* | (2006.01) | |
| *A61N 1/36* | (2006.01) | |
| *A61N 1/05* | (2006.01) | |
| *A61N 1/372* | (2006.01) | |

(52) U.S. Cl.
CPC ............ *A61N 1/0551* (2013.01); *G06T 7/0042* (2013.01); *A61N 1/36185* (2013.01); *G06T 2207/30052* (2013.01); *G06T 2207/10116* (2013.01); *G06T 2207/30196* (2013.01); *A61N 1/37247* (2013.01); *G06T 7/0012* (2013.01); *A61N 1/37264* (2013.01)
USPC ..................... 607/60; 607/32; 607/59; 607/30

(58) Field of Classification Search
USPC ......................................... 607/59, 60, 30, 32
See application file for complete search history.

(56) References Cited

U.S. PATENT DOCUMENTS

| 3,069,654 | A | | 12/1962 | Hough |
| 6,026,142 | A | | 2/2000 | Gueziec et al. |
| 6,068,652 | A | * | 5/2000 | Cohen et al. ................... 607/57 |

(Continued)

FOREIGN PATENT DOCUMENTS

| AU | 709374 | 12/1997 |
| WO | WO 97/43871 | 11/1997 |
| WO | WO 99/37358 | 7/1999 |
| WO | WO2007/007058 A1 | 1/2007 |

OTHER PUBLICATIONS

McIntyre et al., "Electric Field and Stimulating Influence Generated by Deep Brain Stimulation of the Subthalamic Nucleus," Clinical Neurophysiology, vol. 115, 2004, pp. 589-595.

(Continued)

*Primary Examiner* — Niketa Patel
*Assistant Examiner* — William Levicky
(74) *Attorney, Agent, or Firm* — Shumaker & Sieffert, P.A.

(57) ABSTRACT

In general, the disclosure is related to characterization of implanted electrical stimulation electrode arrays using post-implant imaging. The electrode arrays may be carried by implanted leads. Characterization of implanted electrode arrays may include identification of the type or types of leads implanted within a patient and/or determination of positions of the implanted leads or electrodes carried by the leads relative to one another or relative to anatomical structures within the patient. In addition, the disclosure relates to techniques for specifying or modifying patient therapy parameters based on the characterization of the implanted electrode arrays.

53 Claims, 33 Drawing Sheets

(56) References Cited

U.S. PATENT DOCUMENTS

| | | | |
|---|---|---|---|
| 6,358,245 | B1 | 3/2002 | Edwards et al. |
| 6,373,918 | B1 | 4/2002 | Wiemker et al. |
| 6,393,325 | B1 * | 5/2002 | Mann et al. ............. 607/46 |
| 6,697,664 | B2 | 2/2004 | Kienzle, III et al. |
| 6,993,384 | B2 | 1/2006 | Bradley et al. |
| 7,239,920 | B1 | 7/2007 | Thacker et al. |
| 7,346,382 | B2 | 3/2008 | McIntyre et al. |
| 7,831,307 | B1 * | 11/2010 | Moffitt ............. 607/46 |
| 7,853,321 | B2 * | 12/2010 | Jaax et al. ............. 607/2 |
| 2003/0139781 | A1 | 7/2003 | Bradley et al. |
| 2004/0098063 | A1 | 5/2004 | Goetz |
| 2005/0171587 | A1 | 8/2005 | Daglow et al. |
| 2006/0122653 | A1 | 6/2006 | Bradley et al. |
| 2006/0122654 | A1 | 6/2006 | Bradley et al. |
| 2006/0153468 | A1 | 7/2006 | Solf et al. |
| 2006/0195145 | A1 | 8/2006 | Lee et al. |
| 2007/0106360 | A1 | 5/2007 | Gibson et al. |
| 2007/0126967 | A1 | 6/2007 | Choi et al. |
| 2007/0142888 | A1 | 6/2007 | Chavez |
| 2007/0156136 | A1 | 7/2007 | Godara et al. |
| 2007/0185544 | A1 | 8/2007 | Dawant et al. |
| 2007/0203539 | A1 | 8/2007 | Stone et al. |
| 2007/0203545 | A1 | 8/2007 | Stone et al. |
| 2007/0288064 | A1 | 12/2007 | Butson et al. |
| 2008/0052312 | A1 | 2/2008 | Tang et al. |
| 2008/0126968 | A1 * | 5/2008 | West et al. ............. 715/771 |
| 2009/0118635 | A1 | 5/2009 | Lujan et al. |
| 2009/0306746 | A1 * | 12/2009 | Blischak ............. 607/59 |
| 2011/0040546 | A1 | 2/2011 | Gerber et al. |

OTHER PUBLICATIONS

Freeman, et al. "Determining the Minimum-Area Encasing Rectangle for an Arbitrary Closed Curve", Comm. ACM, Jul. 1975, pp. 409-413.

Lindeberg, "Feature Detection With Automatic Scale Selection", International Journal of Computer Vision 30 (2), 1998, pp. 79-116.

Lowe, "Distinctive Image Features from Scale-Invariant Keypoints", International Journal of Computer Vision 60 (2), 2004, pp. 91-110.

Lindeberg, "Detecting Salient Blob-Like Image Structures and Their Scales with a Scale-Space Primal Sketch: A Method for Focus-of-Attention," International Journal of Computer Vision 11 (3), 1993, pp. 283-318.

U.S. Appl. No. 61/025,168, filed Jan. 31, 2008, entitled "Characterization of Electrical Stimulation Electrodes Using Post-Implant Imaging" by Goestz, et al.

U.S. Appl. No. 61/025,158, filed Jan. 31, 2008, entitled "Automated Programming of Electrical Stimulation Electrodes Using Post-Implant Imaging" by Goetz, et al.

U.S. Appl. No. 12/359,247, filed Jan. 23, 2009, entitled "Characterization of Electrical Stimulation Electrodes Using Post-Implant Imaging" by Goetz, et al.

U.S. Appl. No. 12/359,264, filed Jan. 23, 2009, entitled "Electrode-To-Lead Association Using Post-Implant Imaging" by Goetz, et al.

Notification of Transmittal of the International Search Report and the Written Opinion of the International Searching Authority for corresponding patent application No. PCT/US2009/031916, mailed May 18, 2009, 10 pages.

Communication pursuant to Article 94(3) EPC for European Application No. 09 706 151.9-2305, dated Jan. 19, 2011, 3 pages.

Reply to Written Opinion for corresponding patent application No. PCT/US2009/031916, filed Nov. 2, 2009, 12 pages.

Notification of Transmittal of the International Preliminary Report on Patentability for patent application No. PCT/US2009/031916, mailed Jun. 7, 2010, 10 pages.

Office action for U.S. Appl. No. 12/359,247, mailed Aug. 1, 2011, 22 pages.

Office action for U.S. Appl. No. 12/359,264, mailed Aug. 30, 3011, 20 pages.

Response to office action for U.S. Appl. No. 12/359,247, filed Oct. 31, 2011, 24 pages.

Response to office action for U.S. Appl. No. 12/359,247, filed Nov. 1, 2011, 24 pages.

Response to office action for U.S. Appl. No. 12/359,264, filed Nov. 29, 2011, 9 pages.

Office Action dated Aug. 3, 2012 for U.S. Appl. No. 12/625,167, (22 pgs.).

Office Action from U.S. Appl. No. 12/625,167, dated Dec. 21, 2012, 23 pp.

Non-Final Office Action from U.S. Appl. No. 12/625,167, dated Jul. 11, 2013, 20 pp.

Response to Office Action dated Aug. 3, 2012, from U.S. Appl. No. 12/625,167, filed Nov. 2, 2012, 17 pp.

Office Action for U.S. Appl. No. 12/625,167, dated Mar. 26, 2013, 23 pp.

Response to Office Action dated Dec. 21, 2012, from U.S. Appl. No. 12/625,167, filed Feb. 20, 2013, 5 pp.

Response to Office Action dated Mar. 26, 2013, from U.S. Appl. No. 12/625,167, filed May 29, 2013, 10 pp.

Response to Office Action dated Jul. 11, 2013, from U.S. Appl. No. 12/625,167, filed Oct. 10, 2013, 7 pages.

Final Office Action from U.S. Appl. No. 12/625,167, dated Mar. 7, 2014, 22 pp.

* cited by examiner

Actual electrodes marked by black rectangles to highlight illustration of pixel scale Representative of actual electrode image

AUTOMATED PROGRAMMING OF ELECTRICAL STIMULATION ELECTRODES USING POST-IMPLANT IMAGING

This application claims priority from U.S. Provisional Application Ser. No. 61/025,168, filed Jan. 31, 2008, and also claims priority from U.S. Provisional Application Ser. No. 61/025,158, filed Jan. 31, 2008, the entire contents of each being incorporated herein by reference.

TECHNICAL FIELD

The disclosure relates to electrical stimulation therapy and, more particularly, to characterization of implanted neurostimulation electrodes.

BACKGROUND

Implantable electrode arrays may be used to deliver therapy to patients to treat a variety of symptoms or conditions such as chronic pain, tremor, Parkinson's disease, epilepsy, urinary or fecal incontinence, sexual dysfunction, obesity, or gastroparesis. For example, an implantable medical device may deliver neurostimulation therapy via leads that include electrodes located proximate to the spinal cord, pelvic nerves, peripheral nerves, the stomach or other gastrointestinal organs, or within the brain of a patient. In general, the implantable medical device may deliver electrical stimulation therapy in the form of electrical pulses via one or more electrodes carried by one or more implantable leads. Alternatively, electrical stimulation may be delivered by electrode arrays associated with leadless stimulators.

A clinician selects values for a number of programmable parameters in order to define the stimulation therapy to be delivered to a patient. For example, the clinician may select an amplitude, which may be a current or voltage amplitude, and a pulse width for a stimulation waveform to be delivered to the patient, as well as a rate at which the pulses are to be delivered to the patient. The clinician may also select particular electrodes within an electrode array as an electrode combination to be used to deliver the pulses, and polarities of the selected electrodes. In some cases, for current-based systems, electrodes may be identified as source or sink electrodes. A group of parameter values may be referred to as a program in the sense that they drive the stimulation therapy to be delivered to the patient.

Modern neurostimulation systems typically support a variety of electrode array configurations. Different leads, for example, may vary in number of electrodes, shapes and sizes of the electrodes, and spacing between individual electrodes. A patient may have one or more leads, possibly of varying shapes and sizes, implanted to address a particular disease state. Characterization of the types of leads implanted within a patient and the relative positions of the leads and electrodes may be of interest to the caregiver. However, the complexities of modern electrode arrays and uncertainty with respect to implant location and optimum target tissue can make characterization of implanted electrode arrays difficult.

SUMMARY

In general, the disclosure is related to characterization of implanted electrical stimulation electrode arrays using post-implant imaging and analysis. The electrode arrays may be carried by one or more implanted leads or leadless stimulators. Characterization of implanted electrode arrays may include identification of the type or types of leads implanted within a patient as a lead configuration and/or determination of positions of the implanted leads or electrodes carried by the leads relative to one another or relative to anatomical structures within the patient. A programmer may use the characterization to define a representation of the lead configuration for display and programming purposes.

The disclosure also relates to techniques for automatically generating an adjustment to electrical stimulation therapy based on characterization of implanted electrode arrays. For example, a programmer may use relative position information obtained from post-implant image analysis to adjust stimulation parameters such as amplitude, pulse width, pulse rate, electrode combination, polarity or the like. In addition, post-implant image analysis may be used to detect changes in relative positioning, e.g., due to lead migration or position or posture changes. A programmer may automatically generate adjustments to stimulation parameters based on the image analysis to compensate for post-implant migration, position or posture dependencies and promote continued therapeutic efficacy.

In one embodiment, the disclosure provides a method comprising analyzing an electronic image of an electrical stimulation electrode array implanted within a patient to identify one or more physical characteristics of the electrode array, wherein the electrode array includes one or more electrodes, characterizing the array based on the identified physical characteristics, and automatically generating an indication of the characterization of the array.

In another embodiment, the disclosure provides a device comprising an image analysis unit that analyzes an electronic image of an electrical stimulation electrode array implanted within a patient to identify one or more physical characteristics of the electrode array, wherein the electrode array includes one or more electrodes, and a characterization unit that characterizes the electrode array based on the identified physical characteristics, and that automatically generates an indication of the characterization of the array.

In an additional embodiment, the disclosure provides a system comprising an image capture device that obtains an electronic image of an electrical stimulation electrode array implanted within a patient, wherein the array includes one or more electrodes, an image analysis unit that analyzes the electronic image of the electrical stimulation electrode array to identify one or more physical characteristics of the lead, a characterization unit that characterizes the array based on the identified physical characteristics, and that automatically generates an indication of the characterization of the array, and a programmer for an electrical stimulation device coupled to the array.

In a further embodiment, the disclosure provides a computer-readable medium comprising instructions to cause a processor to analyze an electronic image of an electrical stimulation electrode array implanted within a patient to identify one or more physical characteristics of the electrode array, wherein the electrode array comprises one or more electrodes, characterize the electrode array based on the identified physical characteristics, and automatically generate an indication of the characterization of the electrode array.

In another embodiment, the disclosure provides a method comprising obtaining an analysis of an electronic image of an electrical stimulation electrode array implanted within a patient, wherein the electrode array includes one or more electrodes, automatically generating an adjustment to electrical stimulation therapy delivered via the electrode array based on the analysis.

In an additional embodiment, the disclosure provides a device comprising an image analysis interface that obtains an analysis of an electronic image of an electrical stimulation electrode array implanted within a patient, wherein the electrode array includes one or more electrodes, and a programming unit that automatically generates an adjustment to electrical stimulation therapy delivered via the electrode array based on the analysis.

In a further embodiment, the disclosure provides a system comprising an image capture device that obtains an electronic image of an electrical stimulation electrode implanted within a patient, wherein the electrode array includes one or more electrodes, an image analysis device that analyzes the electronic image of the electrical stimulation electrode array, and a programming device that automatically generates an adjustment to electrical stimulation therapy delivered by an electrical stimulation device via the electrode array.

In yet another embodiment, the disclosure provides a system comprising an image analysis unit that calculates distances between representations of electrodes in an electronic image and that identifies groups based on the calculated distances. Each identified group includes a plurality of electrode representations. A distance between a first electrode representation and a second electrode representation in the electronic image is substantially a same distance as a distance between the second electrode representation and a third electrode representation in the electronic image. The system further comprises a characterization unit that determines one or more lead types based on the identified groups.

In a further embodiment, the disclosure provides a method comprising calculating distances between representations of electrodes in an electronic image, identifying groups based on the calculated distances. Each identified group includes a plurality of electrode representations. A distance between a first electrode representation and a second electrode representation of the plurality of electrode representations is substantially a same distance as a distance between the second electrode representation and a third electrode representation of the plurality of electrode representations in the electronic image. The method further comprises determining one or more lead types based on the identified groups.

In a further embodiment, the disclosure provides a system comprising means for calculating distances between representations of electrodes in an electronic image, means for identifying groups based on the calculated distances. Each identified group includes a plurality of electrode representations. A distance between a first electrode representation and a second electrode representation of the plurality of electrode representations is substantially a same distance as a distance between the second electrode representation and a third electrode representation of the plurality of electrode representations in the electronic image. The system further comprises means for determining one or more lead types based on the identified groups.

In a further embodiment, the disclosure provides a computer-readable storage medium comprising instructions that cause one or more processors to, calculate distances between representations of electrodes in an electronic image, identify groups based on the calculated distances. Each identified group includes a plurality of electrode representations. A distance between a first electrode representation and a second electrode representation of the plurality of electrode representations is substantially a same distance as a distance between the second electrode representation and a third electrode representation of the plurality of electrode representations in the electronic image. The computer-readable storage medium comprises instructions that further cause the one or more processors to determine one or more lead types based on the identified groups.

The details of one or more embodiments of techniques described in this disclosure are set forth in the accompanying drawings and the description below. Other features, objects, and advantages of the techniques descried in this disclosure will be apparent from the description and drawings, and from the claims.

DETAILED DESCRIPTION

Figure 1A:
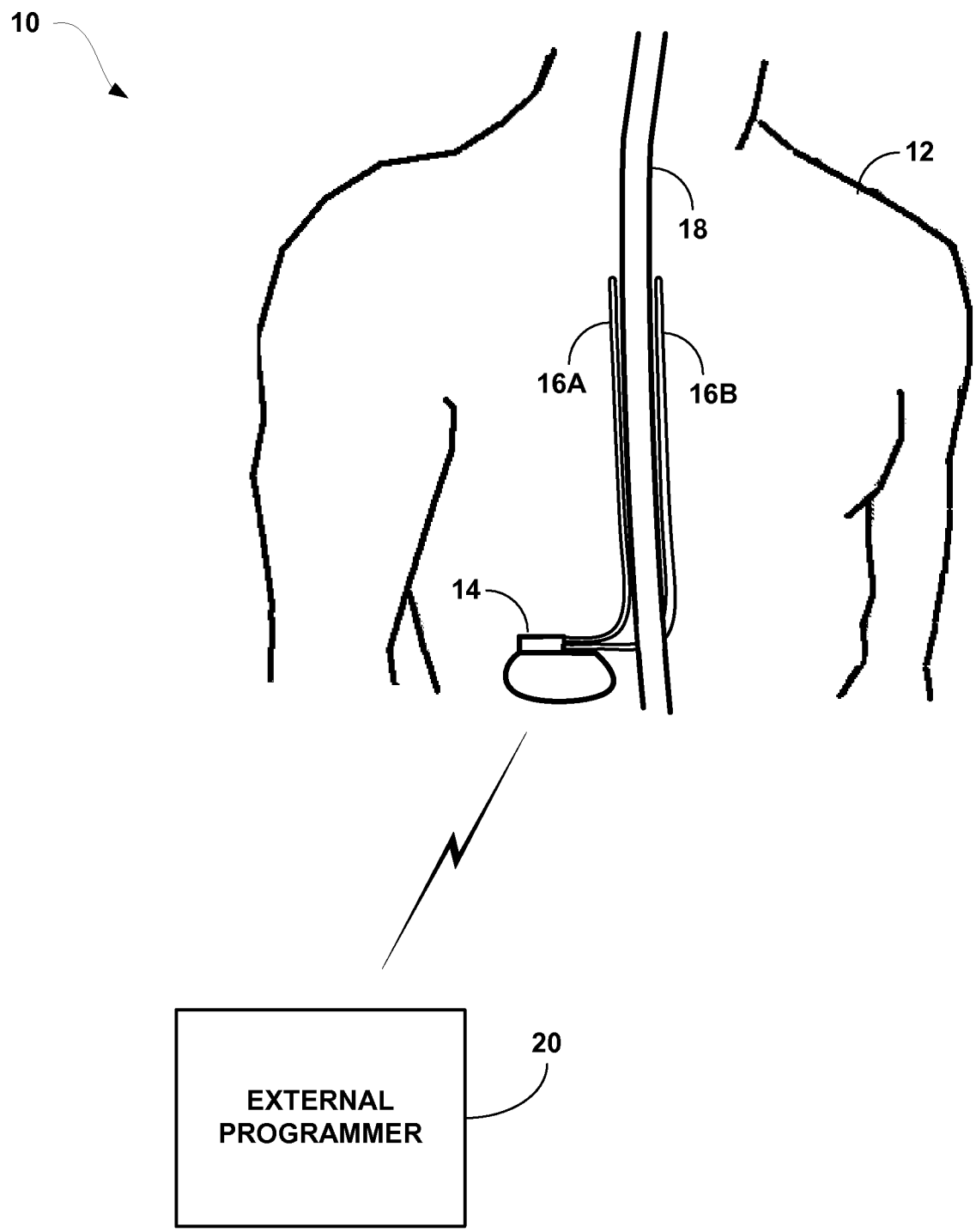
FIG. 1A is a schematic diagram illustrating an implantable stimulation system including a pair of electrode arrays deployed on implantable stimulation leads.

The disclosure is related to characterization of electrical stimulation electrodes using post-implant image analysis. The electrodes may be carried on one or more implantable leads. Characterization of implanted leads may include identification of a lead configuration. A lead configuration may be defined, for example, by the type or types of leads implanted within a patient, the number of leads, and the positions of the implanted electrodes carried by the leads relative to one another and/or relative to anatomical structures within the patient. In addition, the disclosure relates to techniques for generating adjustments to patient therapy parameters based on the characterization of the implanted leads. Hence, the disclosure describes methods and devices that may be useful in automatically characterizing electrical stimulation leads to aid in programming electrical stimulation therapy parameters for a patient.

Electrical stimulation systems, such as systems for neurostimulation, may support electrode arrays that vary in number of electrodes, electrode shape, electrode size, electrode position, and intra-lead electrode spacing. Typically, the electrode arrays are carried by implantable leads. A patient may have one or more leads implanted to form a lead configuration. Some of the leads in a multi-lead configuration may have different physical characteristics, such as different electrode numbers, shapes, sizes, and spacings. Knowledge of the physical characteristics of a lead or lead configuration is desirable for programming electrical stimulation therapy parameters for a patient. When multiple leads are implanted to target an anatomical structure, the relative positioning of the leads and the electrodes carried by the leads also may be of interest. In general, the term "electrode array" may refer to electrodes deployed on percutaneous leads, axial leads, paddle leads, other lead configurations, or in leadless arrangements.

Intra-lead electrode spacing generally refers to the distance between adjacent electrodes on the same lead, and is distinguishable from inter-lead electrode spacing, which generally refers to the distance between electrodes on different leads in a lead configuration. Intra-lead electrode spacing is generally fixed, although it may vary somewhat due to stretching, compression, curvature, twisting or other types of lead migration. Inter-lead spacing, however, may vary substantially depending on implant locations, lead migration or deformation, and patient postures.

As an example, for leads implanted parallel to one another, it may be useful to activate anodes on one lead to help shape stimulation delivered by a cathode on another lead. In this case, the distance between an anode on one lead and a cathode on another lead would be the inter-lead electrode spacing between the electrodes used to form the anode and cathode. As will described in this disclosure, programming algorithms executed by an electrical stimulation device programmer may rely on lead characterization information such as lead type and relative positioning in order to function appropriately.

If a programming algorithm includes a feature to transition stimulation in a transverse fashion, for example, activation of such a feature may be inappropriate for a lead configuration that lacks multiple columns of electrodes. Transverse movement of a stimulation field may be appropriate for a paddle electrode lead having two or more columns or electrodes or a set of two or more parallel leads. However, transverse movement is generally not appropriate for a lead configuration comprising a single lead.

Neurostimulation systems typically rely on user input to determine and record a lead characterization. In particular, a user ordinarily has the task of entering physical characteristics such as lead type, number of leads and relative positioning of leads for a given patient, e.g., into an electrical stimulation device programmer. The lead characterization information may be entered based on the user's own knowledge of the lead configuration and the implant procedure. Unfortunately, such lead characterization information may be entered incorrectly due to error or lack of knowledge, or not entered at all. In addition, for relative positioning of electrodes, the characterization information may be limited in the degree of accuracy, e.g., due to a lack of knowledge concerning the actual post-implant positioning of leads and electrodes in a lead configuration.

Moreover, post-implant migration of leads or patient posture changes may alter the initial relative positioning of the leads. Over time and due to patient movement, one or more of the implanted leads may drift or migrate from their original positions. Lead migration may require a caregiver, such as a physician or clinician, to again determine lead types and attempt to ascertain relative positions in subsequent clinical visits by the patient. In many cases, determining actual relative positions of electrodes is very difficult. In addition, changes in relative positioning due to lead migration may require adjustments to electrical stimulation parameters over time to promote continued efficacy of the electrical stimulation therapy. Determination of proper adjustments may require substantial time and effort on the part of a physician, clinician or other caregiver.

In accordance with various embodiments of this disclosure, lead characterization information can be obtained automatically based on analysis of a post-implant image of the leads within the patient. Automated generation of lead characterization information based on post-implant image analysis, in various embodiments, may reduce clinician time spent determining and entering lead type and relative positioning information, improve the accuracy of such information, and/or yield detailed relative positioning information that otherwise would not be available.

The resulting lead characterization information can then be used to support manual programming by a caregiver, support automated programming algorithms for initial or subsequent adjustment of therapy parameters, or otherwise enhance delivery of electrical stimulation therapies to the patient. In addition, post-implant lead images may be analyzed at later times to detect electrode migration, permitting further manual or automated adjustments to program parameters to promote continued therapeutic efficacy. Automated adjustments may be fully automatic or semi-automatic.

In operation, following implantation of one or more leads within a patient to form a lead configuration, a caregiver may obtain a post-implantation image of the lead configuration within the patient using any of a various imaging modalities, such as fluoroscopy, x-ray imaging, magnetic resonance imaging (MRI) or ultrasound imaging. The imaging modality may generate an electronic image of the implanted lead configuration. An initial electronic image may be obtained upon implantation and relied upon throughout the life of the lead configuration. Alternatively, as mentioned above, the initial electronic image may be supplemented by one or more additional images taken during later clinical visits. Such images, or lead characteristics obtained from such images, may be compared with one another to detect post-implant electrode migration and permit therapy adjustment. Also, in some embodiments, an initial electronic image may include two or more images from different perspectives, e.g., to aid in generation of three-dimensional positioning information.

An image processing device analyzes the image to identify one or more physical characteristics of the lead or leads in the lead configuration. A characterization unit characterizes the electrode array or arrays. For example, the characterization unit may characterize a lead or leads based on the identified physical characteristics, and automatically generate an indication of the lead characterization. The characterization information may be presented on an output device such as a display associated with an electrical stimulation device programmer or some other device. A user may rely on the characterization information to manually adjust various electrical stimulation parameters. Alternatively, or additionally, an automatic or guided programming algorithm may rely on the information to automatically adjust various electrical stimulation parameters. Adjustment of stimulation parameters may refer to initial setting of parameters or modification of existing parameters.

The physical characteristics of the lead may include an electrode number characteristic, an electrode size characteristic, and an intra-lead electrode spacing characteristic. The electrode size characteristic may include an electrode width of one or more electrodes of the leads. As described in more detail below, the electrode width of the electrode may be determined via a size estimation technique. The size estimation technique includes centering an observing rectangle within an electronic image of an identified electrode. The observing rectangle is stretched until the observing rectangle overspills the identified electrode. The observing rectangle may then be rotated and stretched, assuming that stretching the observing rectangle does not already overspill the identified electrode. The observing rectangle may be stretched until the observing rectangle overspills the identified electrode. The process of rotating and stretching the observing rectangle may be repeated until the observing rectangle is fully rotated by 360 degrees. The final width of the observing rectangle may be an approximation of the width of the electrode.

FIG. 1A is a schematic diagram illustrating an implantable stimulation system 10 including a pair of implantable electrode arrays in the form of stimulation leads 16A, 16B implanted within a patient 12. As shown in FIG. 1A, system 10 includes an implantable stimulator 14 and an external programmer 20 shown in conjunction with patient 12. Although FIG. 1A shows an implantable stimulator 14 coupled to fully implanted leads 16A, 16B, the techniques described in this disclosure may be applied to external stimulators coupled to leads via percutaneous lead extensions. In the example of FIG. 1A, leads 16A, 16B are implanted adjacent a spinal cord 18 of patient 12, e.g., for spinal cord stimulation (SCS) to alleviate pain. However, the techniques described in this disclosure are applicable to leads implanted to target any of a variety of target locations within, such as leads carrying electrodes located proximate to spinal cord 18, pelvic nerves, peripheral nerves, the stomach or other gastrointestinal organs, or within the brain of a patient.

In the example of FIG. 1A, stimulation energy is delivered from stimulator 14 to spinal cord 18 of patient 12 via one or more electrodes carried by axial leads 16A and 16B (collectively "leads 16") implanted within the patient. In various applications, such as spinal cord stimulation (SCS), the adjacent implantable leads 16 may have longitudinal axes that are substantially parallel to one another. Various combinations of electrodes carried by the leads 16 may be used to deliver electrical stimulation, including combinations of electrodes on a single lead or combinations of electrodes on both leads. Also, in some embodiments, electrodes may be carried by paddle leads in which an array of electrodes may be arranged in a two-dimensional pattern, e.g., as columns or rows of electrodes.

Although deployment of electrodes via axial leads 16 will be described for purposes of illustration, arrays of electrodes may be deployed in different ways. For example, a housing associated with a leadless stimulator may carry an array of electrodes, e.g., rows, columns, or other patterns of electrodes. For leads or other electrode arrays, electrodes may be formed as any of a variety of electrodes such as ring electrodes, surface electrodes, needle electrodes, pad electrodes, or the like. In general, the term "electrode array" may refer to electrodes deployed on percutaneous leads, axial leads, paddle leads, other lead configurations, or in leadless arrangements. In each case, techniques described in this disclosure may be useful in characterizing electrode arrays in terms of a variety of physical characteristics such as electrode count, size, shape, spacing, and relative positioning.

Using post-implant imagery, the implanted leads may be characterized to identify the type or types of leads implanted within a patient and/or determine positions of the implanted leads and/or electrodes carried by the leads relative to one another and/or or relative to anatomical structures within the patient. In this manner, a caregiver operating programmer 20 may more effectively specify electrical stimulation program parameters such as current or voltage amplitude, pulse rate, pulse width, electrode combination and/or electrode polarity. Acquisition of lead characterization information by post-implant image analysis may promote programming efficiency and accuracy of lead characterization information, including the accuracy of electrode count, shape, size, position and spacing information as well as accuracy of positioning of electrodes relative to one another and, in some cases, relative to anatomical targets for delivery of therapy.

In some embodiments, identified leads may be clustered into groups by system 10. For example, system 10 may have a first set of two leads with four electrodes each (2×4) implanted high in the spine (e.g., near the T9 vertebra) for low back pain and a second set of 2×4 leads implanted in the lumbar region for leg or foot pain. These leads could be clustered based on a distance threshold. For example, the two leads with electrodes implanted near the T9 vertebra could be grouped together on the basis that they are closer to one another than they are to the leads implanted that target the lumbar region. In this case, the T9 and lumbar leads may be identified as two separate groups of two leads each instead of one group of four leads. For example, the two lumbar leads may be identified as group 1 and the two T9 leads may be identified as group 2.

The separate groups may be managed accordingly via the user interface associated with programmer 20, e.g., by separate representation on a display forming a programming screen. As an example, the separate groups may be represented independently of one another on different screens of the display device, possibly with different anatomy links such that electrode combinations are prevented from having anodes and cathodes across groups of leads targeting different anatomical structures. In other words, programmer 20 may be configured to prevent electrode combinations from including electrodes from separate groups.

A variety of therapies may benefit from such a grouping feature. For example, peripheral nerve field stimulation (PNFS) and deep brain stimulation (DBS) therapies may make use of groups of leads implanted to target different anatomical structures. As an illustration, for DBS, different leads may be deployed to stimulation the left and right hemispheres of the brain. In this case, it may be undesirable to permit combinations of electrodes from different lead groups, such as electrodes targeting the left hemisphere in combination with electrodes targeting the right hemisphere.

In addition to lead groups, group of devices and non-lead hardware also could be identified in groups. For example, an image can be analyzed and the user provided with a manifest of implanted hardware, which may include leads, implantable stimulation generators, catheters, implantable drug pumps, or the like, e.g., for purposes of reimbursement or device registration. Recognition of devices and other hardware, such as lead anchors, lead extensions or the like, could be determined on the basis of unique silhouettes or other dimensions (relative to lead dimensions). Also, devices having radio-opaque letter codes in header blocks or other locations could facilitate recognition of devices or other non-lead hardware.

Also, in some embodiments, it may be possible to follow lead and/or lead extension wires back to device connections to determine which leads are coupled to which devices, and which ports in which devices. As an illustration, image analysis may be used to determined that a left lead in the image traces back to the header block socket for electrodes 0-7 of an implantable stimulator, and a right lead in the image traces back to the header block socket for electrodes 8-15. In this manner, it may be possible to determine from the image which lead carries which electrodes in a given lead configuration.

As a further option, images may be used to assess lead and/or system patency. In some cases, lead fractures, kinks or disconnections from the device header block may be automatically identified by an image processing device based on unique image patterns or signatures. In this manner, an image processing device and/or programmer may provide useful system diagnostic information to caregivers during troubleshooting procedures.

Leads 16 may migrate on a short-term or longer-term basis. For example, patient posture changes or movement may cause short-term lead migration. Over time, leads 16 may undergo more long term migration. In each case, the positions of the electrodes carried by the leads 16 may be different from the positions of the electrodes at initial implantation. The different positions of the electrodes due to migration may be different relative to the position of other electrodes, e.g., on different leads. In addition, the different positions due to migration may be different relative to anatomical targets for the delivery of stimulation.

Due to the migration of leads 16, a clinician may not be able to identify the particular lead types that were implanted in the patient. For example, lead 16A and lead 16B may migrate so that it is difficult for the clinician or patient to determine exactly which lead is in which position. Electrodes of lead 16A may overlap with lead of 16B, or vice versa. This may cause the clinician or patient to incorrectly identify the type of lead that was implanted. Additionally, leads 16 may migrate such that the programmed therapy is no longer effective.

For example, lead 16A may migrate horizontally, vertically, or a combination of both, relative to lead 16B, such that electrodes forming an electrode combination are spaced further apart than upon initial implantation. In this case, the programmed amplitude of the electrical pulse may be too low to provide continued efficacy of therapy for the patient's condition, such that it may be desirable to increase amplitude or select another electrode on one of the leads 16 to reduce the spacing. As another example, one or both of leads 16 may migrate vertically or horizontally, or both, relative to an anatomical target. In this case, the current program may be delivering electrical stimulation to electrodes that are not located sufficiently near to an anatomical target, in which case it may be desirable to select different electrodes for delivery of stimulation energy.

In a case in which a set of electrodes or leads are observed to have high positional or postural variability such that the positions of the electrodes or leads varies greatly from posture to posture or position to position, programmer 20 may be configured to discourage use of such electrodes or leads for chronic therapy. For example, programmer 20 may generate notifications to the user, indicating that use of the electrodes or leads for chronic therapy may be undesirable. Alternatively, or additionally, programmer 20 may be configured to place such electrodes or leads later in a sequence of potential electrodes or leads presented to the user for selection as part of a guided search protocol.

In the example of FIG. 1A, leads 16 carry electrodes that are placed adjacent to the target tissue of spinal cord 18. In particular, leads 16 may be implanted in the epidural space adjacent spinal cord 18, and coupled to an implanted stimulator 14. In the example of FIG. 1A, stimulation energy may be delivered to spinal cord 18 to eliminate or reduce pain perceived by patient 12. However, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, gastric stimulation, and the like. The stimulation may be configured to alleviate a variety of symptoms or conditions such as chronic pain, tremor, Parkinson's disease, epilepsy, urinary or fecal incontinence, sexual dysfunction, obesity, or gastroparesis. The stimulation delivered by stimulator 14 may take the form of stimulation pulses or continuous waveforms, and may be characterized by controlled voltage levels or controlled current levels, as well as pulse width and pulse rate in the case of stimulation pulses.

The stimulation energy may be delivered via selected combinations of electrodes carried by one or both of leads 16. The target tissue may be any tissue affected by electrical stimulation energy, such as electrical stimulation pulses or waveforms. Such tissue may include nerves, nerve branches, smooth muscle fiber, and skeletal muscle fiber. In the example illustrated by FIG. 1A, the target tissue is spinal cord 18. Stimulation of spinal cord 18 may, for example, prevent pain signals from traveling thorough the spinal cord and to the brain of the patient. Patient 12 may perceive the interruption of pain signals as a reduction in pain and, therefore, efficacious therapy. However, as described above, inaccurate or imprecise knowledge of lead position or lead migration can result in delivery of therapy with sub-optimal parameters and insufficient efficacy.

With reference to FIG. 1A, a user, such as a clinician, physician or patient 12, may interact with a user interface of external programmer 20 to program stimulator 14. Programming of stimulator 14 may refer generally to the generation and transfer of commands, programs, or other information to control the operation of the stimulator. For example, programmer 20 may transmit programs, parameter adjustments, program selections, group selections, or other information to control the operation of stimulator 14, e.g., by wireless telemetry. Parameter adjustments may refer to initial parameter settings or adjustments to such settings. A program may specify a set of parameters that define stimulation. A group may specify a set of programs that define different types of stimulation, which may be delivered simultaneously using pulses with independent amplitudes or on a time-interleaved basis.

An example of a commercially available clinician programmer is the Medtronic N'Vision® Programmer Model 8840, marketed by Medtronic, Inc., of Minneapolis, Minn. An example of a commercially available patient programmer is the Medtronic myStim® Programmer, marketed by Medtronic, Inc. In some cases, external programmer 20 may be a physician or clinician programmer if it is primarily intended for use by a physician or clinician. In other cases, external programmer 20 may be a patient programmer if it is primarily intended for use by a patient. In general, a physician or clinician programmer may support selection and generation of programs or parameters by a clinician for use by stimulator 14, whereas a patient programmer may support more limited adjustment and selection of such programs or parameters by a patient during ordinary use.

Stimulator 14 may be implanted in patient 12 at a location minimally noticeable to the patient. Alternatively, stimulator may be external to patient 12 and coupled to implanted leads via a percutaneous extension. For spinal cord stimulation (SCS), stimulator 14 may be located, for example, in the lower abdomen, lower back, or other location to secure the stimulator. Leads 16 may be tunneled from stimulator 14 through tissue to reach the target tissue adjacent to spinal cord 18 for stimulation delivery. At the distal tips of leads 16 are one or more electrodes (not shown) that transfer stimulation energy from the lead to the tissue. The electrodes may be electrode pads on a paddle lead, circular (i.e., ring) electrodes, surrounding the body of leads 16, conformable electrodes, cuff electrodes, or any other type of electrodes capable of forming unipolar, bipolar or multipolar electrode configurations. In general, ring electrodes arranged at different axial positions at the distal ends of leads 16 will be described for purposes of illustration.

Each of the electrode combinations specifies a combination of electrodes arranged along lengths of two or more leads. If each lead 16 includes four electrodes, then the leads can be viewed as having four axial positions or levels. An electrode combination may include combinations of electrodes on one lead or multiple leads, as well as one or more electrodes on a housing of stimulator 14 in some cases. In each case, some electrodes in an electrode combination may form anodes while other electrodes form cathodes, establishing paths for flow of electrical stimulation current relative to an anatomical target such as spinal cord nerve tissue at a desired position on the spinal cord. As an example, for SCS, stimulation may be delivered in the vicinity of the T7, T8 and T9 vertebrae, although other positions on the spinal cord are possible. In a current-based system, instead of cathodes and anodes, electrodes maybe selected to form current sources and sinks.

External programmer 20 presents an interface that permits modification of the current program by adjustment of parameter values such as amplitude, pulse width, pulse rate, electrode combination, and electrode polarity. Adjustments may be desirable in the case of lead migration, accommodation, or disease progression, in which cases the current (i.e., present) stimulation program may no longer be as effective as when the program was initially established. Lead characterization based on analysis of post-implant imagery, as described in this disclosure, may aid the caregiver or an automated programming algorithm in adjusting stimulation parameters to enhance therapeutic efficacy.

Figure 1B:
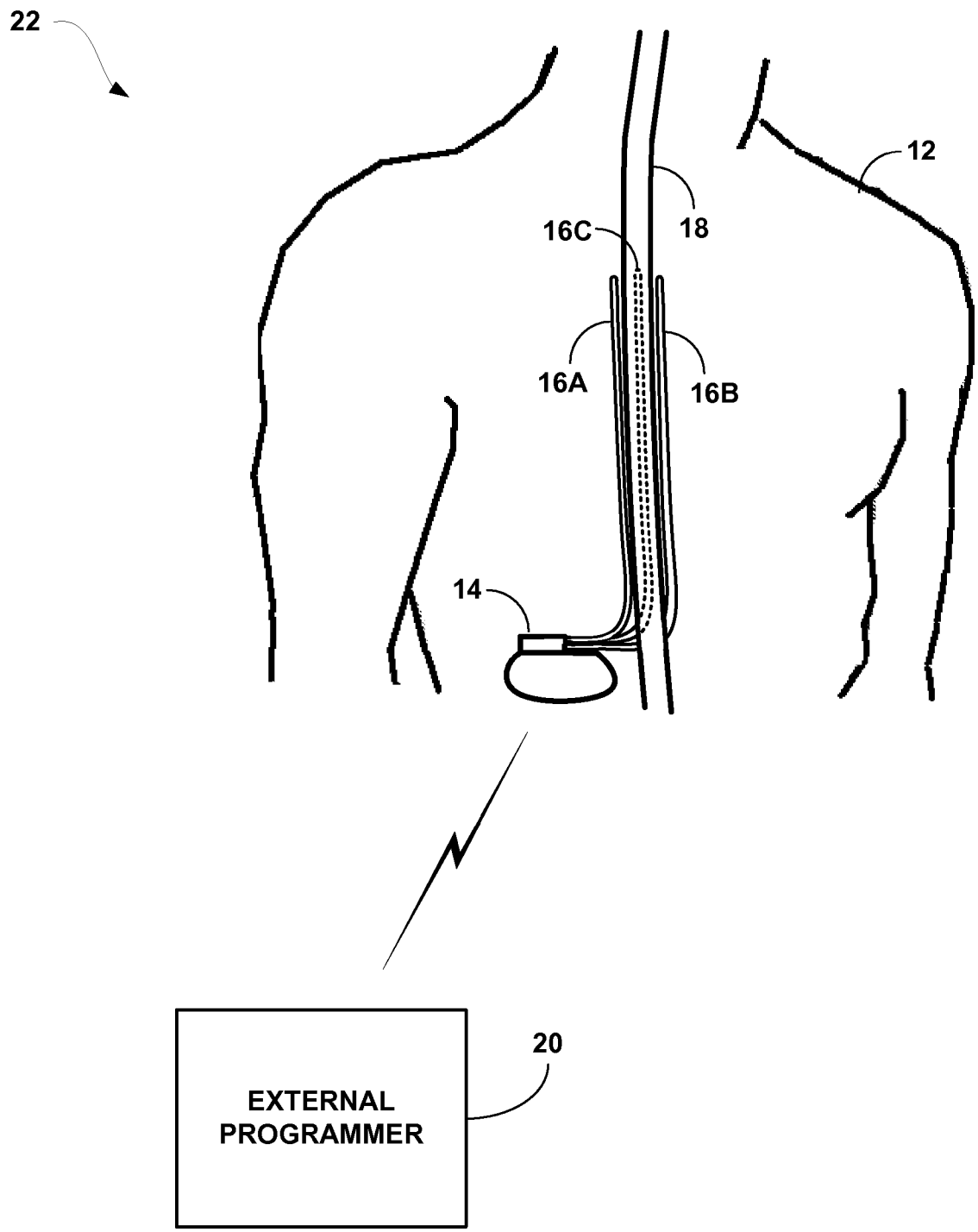
FIG. 1B is a schematic diagram illustrating an implantable stimulation system including a trio of electrode arrays deployed on implantable stimulation leads.

FIG. 1B is a schematic diagram illustrating an implantable stimulation system 22 including a trio of implantable stimulation leads 16A, 16B, 16C (collectively leads 16). System 22 generally conforms to system 10 of FIG. 1A, but includes a third lead 16C. Accordingly, stimulator 14 may deliver stimulation via combinations of electrodes carried by all three leads 16, or a subset of the three leads. Third lead 16C may reside spatially between leads 16A and 16B. Third lead 16C may include the same number of electrodes as leads 16A and 16B, or a greater number of electrodes than leads 16A and 16B. In the latter case, additional electrodes on lead 16C may be used to form more numerous and more complex electrical stimulation patterns in conjunction with the stimulation electrodes on lead 16A and/or lead 16B. With different electrode counts, sizes, positions and intra-lead electrode spacing among leads 16A, 16B and 16C, as well as variation in relative inter-lead electrode spacing among the leads, lead characterization information can be helpful for effective programming of the electrical stimulation delivered by stimulator 14 via the leads.

Figure 2:
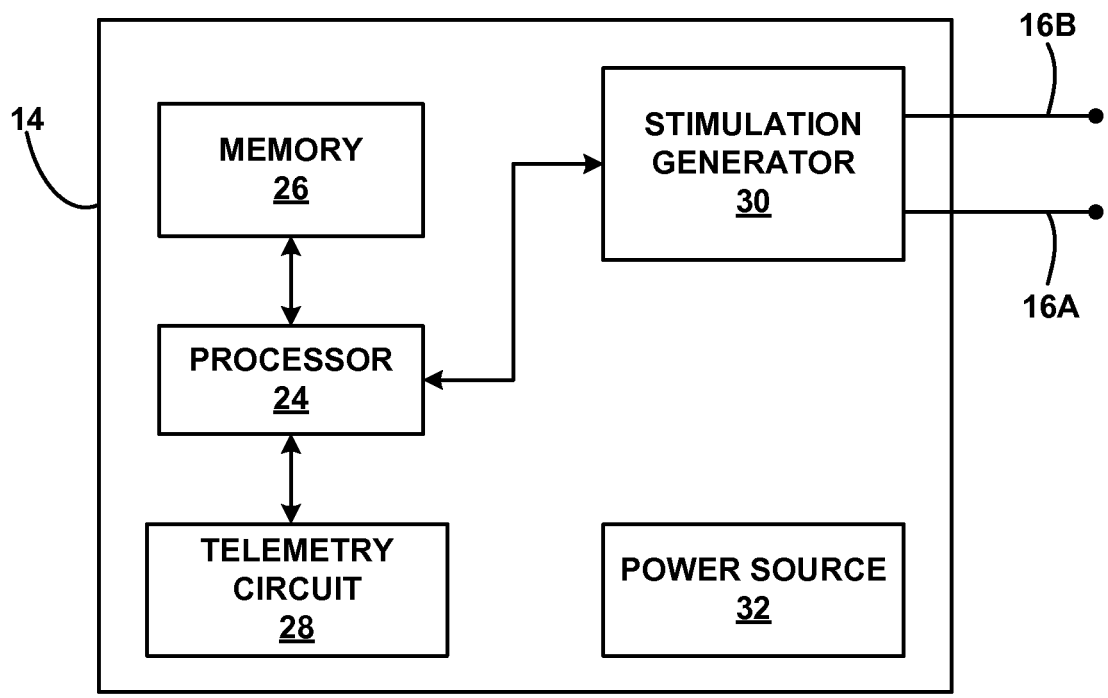
FIG. 2 is a functional block diagram illustrating various example components of an implantable electrical stimulator.

FIG. 2 is a functional block diagram illustrating various components of an implantable stimulator 14. In the example of FIG. 2, stimulator 14 includes a processor 24, memory 26, stimulation signal generator 30, telemetry circuit 28, and power source 32. Memory 26 may store instructions for execution by processor 24, stimulation therapy program data, sensor data, operational and status data, and any other information regarding therapy or patient 12. Stimulation program data may include stimulation parameters transmitted from programmer 20, as well as programs defined by such parameters, and program groups. Some data may be recorded for long-term storage and retrieval by a user. Memory 26 may include separate memories for storing different types of data.

Processor 24 controls stimulation generator 30 to deliver electrical stimulation via electrode combinations formed by electrodes in one or more electrode arrays. For example, stimulation generator 30 may deliver electrical stimulation therapy via electrodes of one or more leads 16, e.g., as stimulation pulses or continuous waveforms. Stimulation generator 30 may include stimulation generation circuitry to generate stimulation pulses or waveforms and switching circuitry to switch the stimulation across different electrode combinations, e.g., in response to control by processor 24. In particular, processor 24 may control the switching circuitry on a selective basis to cause stimulation generator 30 to deliver electrical stimulation to selected electrode combinations and to shift the electrical stimulation to different electrode combinations. Alternatively, in some embodiments, stimulation generator 30 may include multiple current or voltage sources to control delivery of stimulation energy to selected combinations of electrodes carried by leads 16.

Electrode combinations and other parameters associated with different therapy programs may be represented by data stored in a memory location, e.g., in memory 26, of stimulator 14. Processor 24 may access the memory location to determine the electrode combination for a particular program and control stimulation generator 30 to deliver electrical stimulation via the indicated electrode combination. Each program may specify a set of parameters for delivery of electrical stimulation therapy. As an example, a program may specify electrode combination, electrode polarities, current or voltage amplitude, pulse rate and pulse width. Additional parameters such as duty cycle, duration, and delivery schedule also may be specified by a therapy program.

Using an external programmer, such as programmer 20, a user may select individual programs for delivery on an individual basis, or combinations of programs for delivery on a simultaneous or interleaved basis. In addition, a user may adjust parameters associated with the programs. The programs may be stored in memory 26 of implantable stimulator 14, as shown in FIG. 2. Alternatively, the programs may be stored in memory associated with external programmer 20. In either case, the programs may be selectable and adjustable to permit modification of therapy parameters. In addition, a physician programmer may permit generation of new programs, which may be loaded into memory 26, and adjustment of parameters associated with existing programs.

Upon selection of a particular program or program group from memory 26, processor 24 may control stimulation generator 30 to deliver stimulation according to the programs in the groups, e.g., simultaneously or on a time-interleaved basis. A group may include a single program or multiple programs, each of which specifies an electrode combination. Again, the electrode combination may specify particular electrodes in a single array or multiple arrays, e.g., on a single lead or among multiple leads.

Stimulator 14 may be responsive to adjustments of programming parameters and electrode configurations by a user via programmer 20. In particular, processor 24 may receive adjustments to program parameters from programmer 20 via telemetry circuit 28. Telemetry circuit 28 may support wireless telemetry with external programmer 20 or another device by radio frequency (RF) communication, proximal inductive interaction of stimulator 14 with external programmer 20, or other techniques. Telemetry circuit 28 may send information to and receive information from external programmer 20 on a continuous basis, at periodic intervals, or upon request from the stimulator or programmer. To support RF communication, telemetry circuit 28 may include appropriate electronic components, such as amplifiers, filters, mixers, encoders, decoders, modulators, demodulators and the like.

Power source 32 delivers operating power to the components of stimulator 14. Power source 32 may include a small rechargeable or non-rechargeable battery and a power generation circuit to produce the operating power. Recharging may be accomplished through proximal inductive interaction between an external charger and an inductive charging coil within stimulator 14. In some embodiments, power requirements may be small enough to allow stimulator 14 to utilize patient motion and implement a kinetic energy-scavenging device to trickle charge a rechargeable battery. In other embodiments, traditional nonrechargeable batteries may be used for a limited period of time. As a further alternative, an external inductive power supply could transcutaneously power stimulator 14 when needed or desired.

Figure 3:
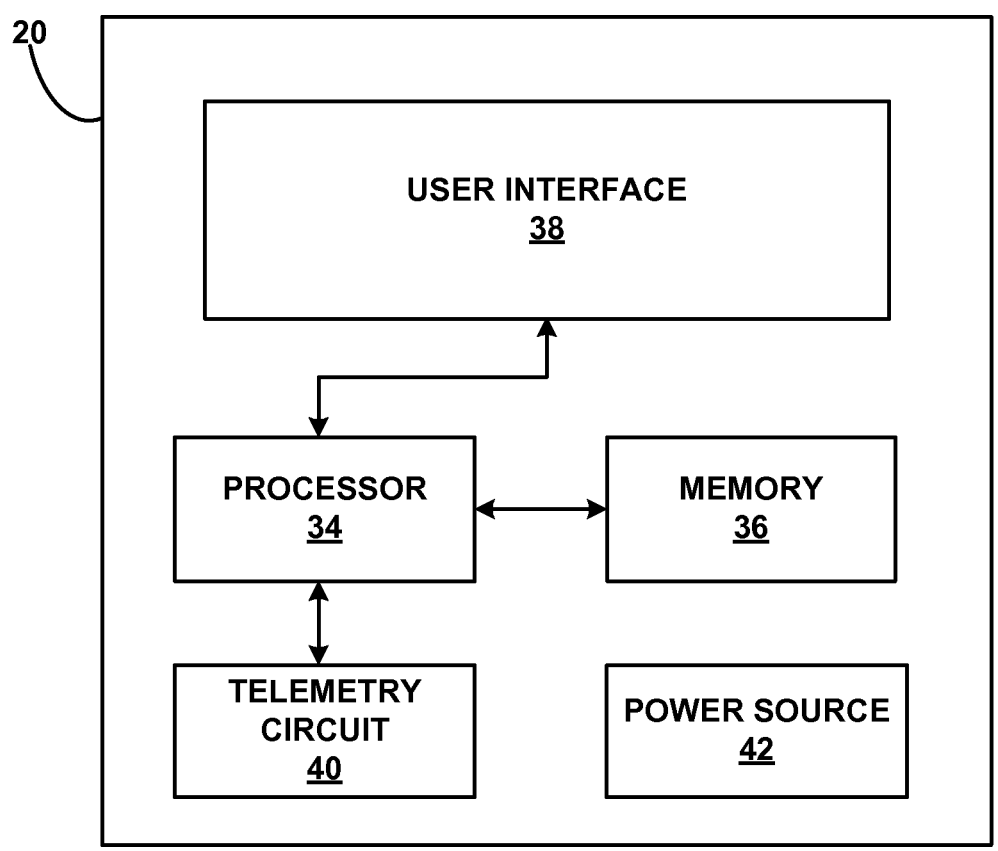
FIG. 3 is a functional block diagram illustrating various example components of a programmer for use in programming parameters of an electrical stimulator.

FIG. 3 is a functional block diagram illustrating various components of an external programmer 20 for an implantable stimulator 14. As shown in FIG. 3, external programmer 20 includes processor 34, memory 36, telemetry circuit 40, user interface 38, and power source 42. In the case of a clinician programmer, a clinician interacts with user interface 38 in order to generate programs and adjust program parameters, such as voltage or current amplitude, pulse width, pulse rate, electrode combinations and electrode polarities. Generation of programs and adjustment of program parameters may be aided by automated programming algorithms that guide the physician or clinician to select particular programs and program parameters. In the case of a patient programmer, a patient interacts with user interface 38 to select programs and adjust program parameters, e.g., on a limited basis as specified by the physician or clinician.

User interface 38 may include a screen and one or more input buttons, as shown in FIG. 2, that allow external programmer 20 to receive input from a user. The screen may be a liquid crystal display (LCD), dot matrix display, or touch screen. The input buttons may include a touch pad, increase and decrease buttons, emergency shut off button, and other buttons needed to control the stimulation therapy. In some cases, the user may interact with user interface 38 via a stylus, soft keys, hard keys, directional devices, and any of a variety of other input media. Processor 34 receives input from user interface 38, presents data via the user interface, retrieves data from memory 36 and stores data within the memory. Processor 34 also controls the transmission of data via telemetry circuit 40 to stimulator 14. Memory 36 may include operational instructions for processor 34 or program parameter sets.

Telemetry circuit 40 allows the transfer of data to and from stimulator 14. Telemetry circuit 40 may communicate automatically with telemetry circuit 28 of stimulator 14 at a scheduled time or when the telemetry circuit detects the proximity of the stimulator. Alternatively, telemetry circuit 40 may communicate with stimulator 14 when signaled by a user through user interface 38. To support RF communication, telemetry circuit 40 may include appropriate electronic components, such as amplifiers, filters, mixers, encoders, decoders, modulators, demodulators and the like. Power source 42 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Figure 4A:
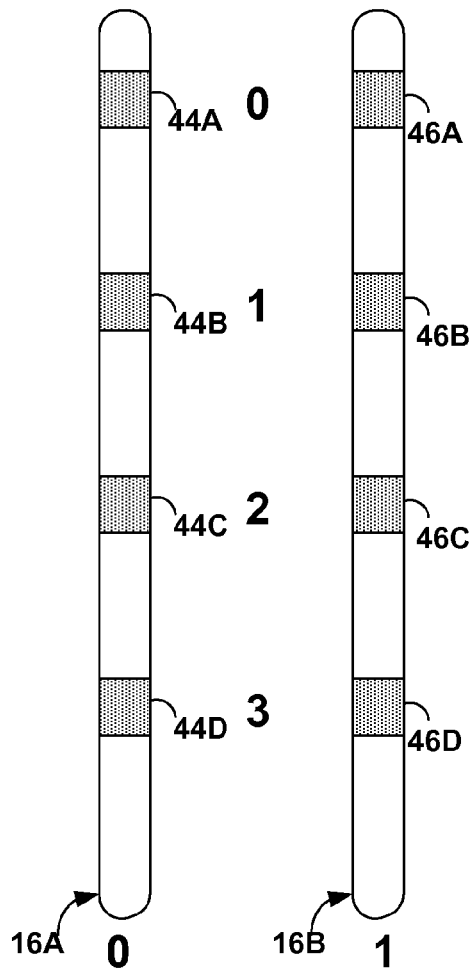
FIG. 4A is a schematic diagram illustrating a pair of leads with the same electrode counts, sizes, positions and intra-lead electrode spacing.

FIG. 4A is a schematic diagram illustrating a pair of leads 16 with the same electrode count, electrode size, electrode shape and intra-lead electrode spacing. Electrodes 44A-44D (herein referred to as electrodes 44) reside on lead 16A. Electrodes 46A-46D (herein referred to as electrodes 46) reside on lead 16B. Post-implant characterization of the electrode arrays carried by leads 16 may be helpful in initial programming of implantable stimulator 14. Although leads 16 are substantially identical, it is important to know that the leads are substantially identical so that appropriate programming can be applied by programmer 20. Post-implant image analysis can provide an automated technique for determining and recording the lead characterization based on physical characteristics of the leads 16. In this manner, programmer 20 can present programming options appropriate for the actual lead configuration implanted in the patient. For example, if the two leads 16 each have four electrodes, i.e., a 2×4 lead configuration, it would be inappropriate to present programming options for a 2×8 (two lead with eight electrodes each), 4-8 (a four electrode lead and an eight electrode lead) or 4-8-4 (an eight electrode lead between two four electrode leads) lead configuration in which one lead has eight electrodes while the other lead or leads have four electrodes.

In addition, even though leads 16 are substantially identical, the precise relative positioning of the electrodes carried by the leads may vary due to different implant positions of the leads. In the case of SCS, for example, one lead 16A may be implanted somewhat higher along the spinal cord that the other lead 16B. Accordingly, distances between respective electrodes 44, 46 may vary with different implant positions. Knowledge of relative electrode positions and/or identified groupings of leads may be important in adjusting respective stimulation amplitudes or selecting different combinations of electrodes. As will be described, in some embodiments, multiple images may be obtained from different perspectives to ascertain relative positioning of electrodes in different dimensions. In addition, image analysis may be used to determine positioning of electrodes relative to anatomical targets, e.g., particular vertebrae of the spinal column in the case of SCS.

Also, as leads 16 migrate over time, the characterization of electrodes 44 and electrodes 46, and particularly relative positioning, may need to be modified so that stimulation parameters can be adjusted. For example, with further reference to FIG. 4A, assuming an electrode combination included electrode 44A as a cathode and electrode 46A as an anode, if leads 16 migrated horizontally away from one another, it may be desirable to increase stimulation amplitude due to increased distance between electrodes 44A and 46A. If leads 16 migrated horizontally away from one another the amplitude of the electric stimulation may be too low to properly provide therapy to the patient.

If leads 16 migrated vertically relative to one another, it likewise may be desirable to increase amplitude. For example, if leads 16 migrated vertically, electric stimulation from electrodes 44A to 46A may not provide therapy to the correct target tissue. If significant migration occurs relative to an anatomical target, e.g., such as the T7 vertebra of the spinal cord 18, it may be desirable to select a different electrode combination that more effectively delivers stimulation therapy to the target. In each case, post-implant image analysis can aid in adjustment of stimulation parameters such as amplitude, pulse width, pulse rate, electrode combination and electrode polarity to promote continued therapeutic efficacy.

Figure 4B:
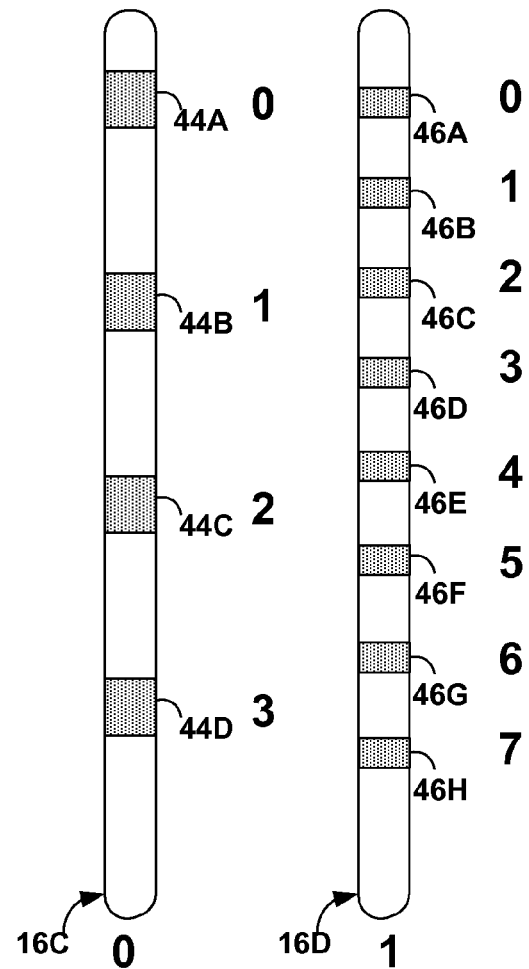
FIG. 4B is a schematic diagram illustrating a pair of leads with different electrode counts, sizes, positions and intra-lead electrode spacing.

FIG. 4B is a schematic diagram illustrating a pair of leads 16C and 16D with different electrode count, electrode size, and intra-lead electrode spacing. Lead 16C in FIG. 4B includes four electrodes 44A-44D (collectively electrodes 44), whereas lead 16D includes eight electrodes 46A-46H (collectively electrodes 46). The size of electrodes 44 is different from the size of electrodes 46 in the example of FIG. 4B. For example, the axial length of each electrode along the longitudinal length of each lead 16 is different. In particular, in FIG. 4B, the axial length of each electrode 46 is less than the axial length of each electrode 44. To establish programming options for combinations of electrodes between leads 16C and 16D, as well as associated parameters such as amplitude, pulse width and pulse rate, it is important to know the lead configuration produced by the 4-8 combination of leads 16C and 16D.

Post-implant image analysis can provide automatic characterization of leads 16C and 16D. For example, by image analysis, leads 16C and 16D may be recognized as particular types of leads with particular electrode counts, sizes, shapes and intra-lead electrode spacing. In addition, post-implant image analysis can provide actual relative positioning information for the electrodes carried by the leads. With each type of information, programmer 20 can present appropriate programming options and parameters to a user for use in programming stimulator 14. For example, based on the image analysis, programmer 20 can present options and parameters for a 4-8 combination of leads rather than an 8-8 or 4-8-4 combination.

Figure 5A:
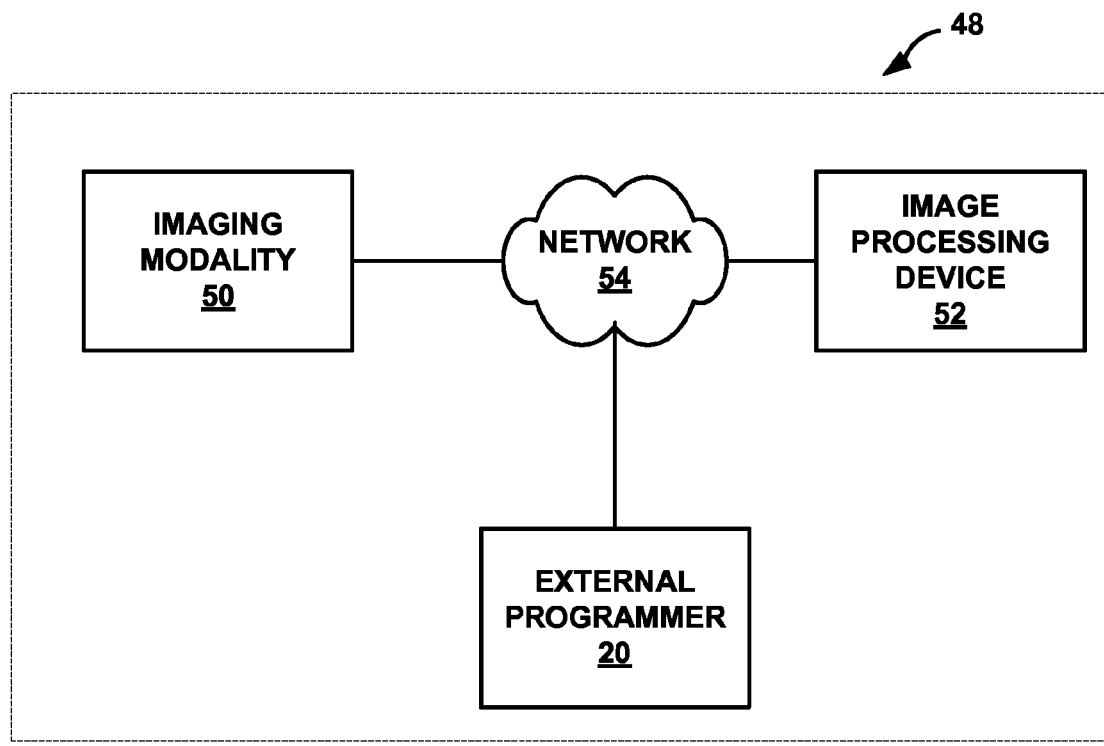
FIG. 5A is a block diagram illustrating an example system for characterizing implanted electrode arrays using post-implant image analysis.

FIG. 5A is a schematic diagram illustrating a system 48 for obtaining lead characterization information based on post-implant image analysis. In the example of FIG. 5A, system 48 includes at least one imaging modality 50, an image processing device 52, and an external programmer 20. Imaging modality 50, image processing device 52 and programmer 20 may be coupled via a network 54 to exchange information with one another. For example, image processing device 52 may receive electronic images from imaging modality 50 via network 54, and external programmer 20 may receive electrode array characterization information from image processing device 52 via network 54. As alternatives, one or more of imaging modality 50, image processing device 52, and external programmer 20 may exchange information by other techniques, such as direct connect interfaces, wireless telemetry, exchange of data storage media such as memory cards or disks, or the like.

In addition, although imaging modality 50, image processing device 52 and external programmer 20 are shown as separate devices, in other embodiments, one or more of such components may be integrated with one another. For example, image processing device 52 may be partially or fully integrated as components or features of imaging modality 50. As another example, some or all of the aspects of image processing device 52 may be integrated as components or features of external programmer 20. In some cases, however, imaging modality 50 may be located in an imaging department of a health care facility, and communicate electronic imagery to an image processing device 52 located in a different department of the health care facility via network communication, e.g., according to Digital Imaging and Communications in Medicine (DICOM) protocols for distributing and viewing medical images. Accordingly, in terms of implementation, the example of FIG. 5A is provided for purposes of illustration and should not be considered limiting of the techniques broadly embodied and described in this disclosure.

Imaging modality 50 may be any type of device useful in obtaining a post-implant image of leads 16. For example, imaging modality 50 may be fluoroscopy device, X-ray device, magnetic resonance imaging (MRI) device, ultrasound imaging device, or the like. In some embodiments, imaging modality 50 may be an image archival system such as a so-called picture archiving and communication system (PACS) that stores previously acquired images for retrieval by viewing stations, image processing devices and the like. Hence, image processing device 52 may obtain the post-implant image directly from an imaging device or from an archival device such as a PACS device.

Imaging modality 50 may produce the image in a digital, pixelized format. As will be described below, FIGS. 10, 11A, 11B, 11C, and 12 provide examples of a fluoroscopy image of implanted leads, and various image processing and analysis operations that may be applied to identify physical characteristics of the leads to produce lead characterization information. In the example of FIG. 5A, imaging modality 50 transmits the image to image processing device 52 via network 54. In some embodiments, imaging modality 50 or image processing device 52 may provide the image, or a reduced spatial resolution version of the image, to external programmer 20. In further embodiments, the image may be a volumetric model or three-dimensional in nature. For example, slices of the model can be taken to obtain two-dimensional pixel images at different planes. In this case, the image analysis process may be applied to image slices. Alternatively, or additionally, the image analysis process can proceed in 3D with volume pixels (voxels) or equivalent volumetric entities.

In some embodiments, external programmer 20 may be configured to present an image or representation of the image obtained by imaging modality 50 on a selective basis when desired by a user. In some cases, the image may form part of the lead characterization information provided to external programmer 20 by image processing device 52. Image processing device 52 may also display the image on a display unit coupled to the image processing image, e.g., for viewing by user before, during or after image analysis. In some embodiments, operation of image processing device 52 may be entirely automatic. In other embodiments, operation of image processing device 52 may be aided by interaction with a user to direct one or more image processing operations.

Network 54 may be any type of network known in the art to communicatively couple imaging modality 50, image processing device 52, and external controller 20. For example, network 54 may include a local area network (LAN), a wide area network (WAN), or a global network such as the Internet, and may rely on wired connections, wireless connections, or a combination of both. As mentioned above, in some cases, imaging modality 50 and image processing device 52 may be equipped to communicate image information according to DICOM protocols. Imaging modality 50 and/or image processing device 52 also may include memory and/or data storage media to archive and temporarily store image data for use in post-implant image analysis. For example, image data may be stored in a long-term archive for retrieval at later dates, e.g., for analysis of lead migration. Alternatively, or additionally, lead migration may be analyzed using comparison of characterization information produced by image analysis, rather than comparison of image data itself. In either case, archival of image data and characterization data may be desirable.

Image processing device 52 may be any type of device capable of processing images. For example, image processing device 52 may be a general purpose computer that includes suitable hardware and software for image analysis as described in this disclosure. In some embodiments, image processing device 52 may be any suitable stand-alone computer. In other embodiments, all or some of the structural and functional aspects of image processing device 52 may be integrated with or form part of external programmer 20 or imaging modality 50. As a further embodiment, instead of a general purpose computer, image processing device 52 may be a dedicated computing device that is specially configured for image processing. Hence, in some embodiments, imaging modality 50 or external programmer 20 may form image processing device 52. As shown in FIG. 5A, imaging modality 50 is connected to image processing device 52 via network 54. However, in some embodiments, image processing device 52 may be a part of imaging modality 50. In some embodiments, image processing device 52 may not be needed. In such cases, external programmer 20 may perform some or all of the functions of image processing device 52.

In some embodiments, a digital scanner or digital camera may be used to capture an image from a fluoroscopy imaging machine in an operating room. Hence, an image capture device, such as a scanner or camera, may operate as an intermediate device between imaging modality 50 and image processing device 52. For example, the scanner or camera could capture the image from a sheet of film or from a display screen associated with a fluoroscopy imaging machine. The scanner or camera may be an independent, stand-alone device or may be built into programmer 20 or some other device. The image obtained from the scanner or camera may be analyzed in a computer associated with image processing device 52, or by computing hardware associated with programmer 20 or some other device. A scanner or digital camera may be useful in cases where image capture logistics are more complicated. For example, if a facility does not store or communicate images electronically, image capture from film or a display screen may permit image analysis for lead characterization.

Imaging modality 50 obtains an electronic image of an electrode array implanted within the patient. Image processing device 52 processes and analyzes the electronic image to identify one or more physical characteristics of the electrode array, characterizes the array based on the identified physical characteristics, and generates an indication of the characterization of the array. The physical characteristics may include electrode count, electrode shape, electrode size, intra-lead electrode spacing on a given lead, lead identification markers or fiducials, anatomical landmarks, and relative positions of electrodes on different leads. In addition, the physical characteristics may include electrode array orientation, i.e., vertical, horizontal, or diagonal relative to the length of the patient's body. One or more such physical characteristics may be used to characterize the electrode array or arrays so that appropriate programming options and parameters may be presented by external programmer 20. In some cases, image processing device 52 may specify the types of leads implanted within the patient based on comparison of physical characteristics obtained from image analysis to physical characteristics of known lead types.

A variety of additional features may be added to leads to assist in lead identification. For example, some leads may include radio-opaque identification codes, such as bar codes, alphanumeric information, shapes, or the like to aid in automated or user-aided identification of leads. In some cases, these types of features may support more immediate recognition of lead types for purposes of lead characterization, and permit the image analysis process to proceed more quickly analysis of relative electrode and/or lead positioning.

Figure 5B:
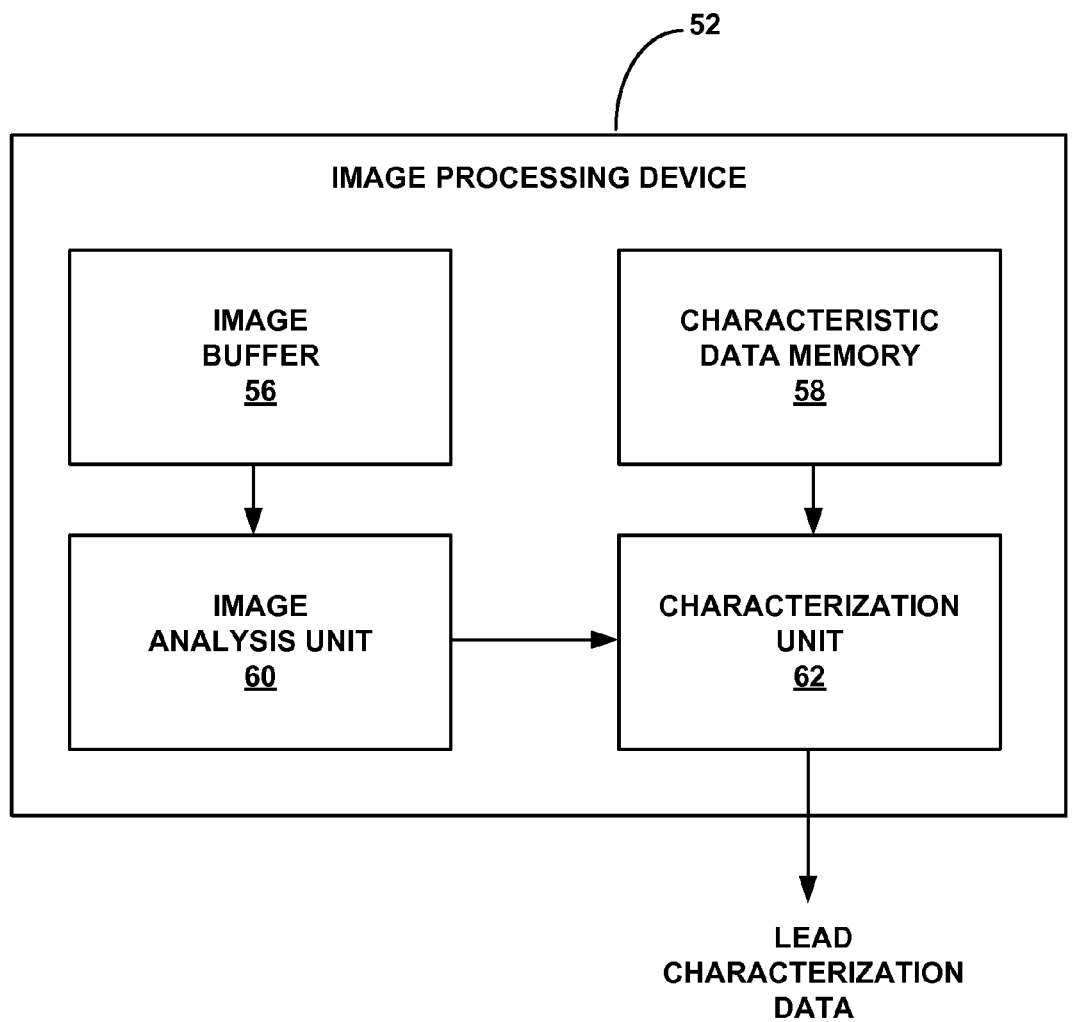
FIG. 5B is a block diagram illustrating example components of an image processing device used to analyze post-implant imagery for characterization of implanted electrode arrays.

FIG. 5B is a block diagram illustrating example components of an image processing device 52 used to analyze post-implant imagery for characterization of implanted electrode arrays. In the example of FIG. 5B, image processing device 52 includes a lead image buffer 56, an image analysis unit 60, a lead characterization unit 62, and a characteristic data memory 58. However, other components or arrangements are possible. Lead image buffer 56 may provide a memory buffer that receives from imaging modality 50 a post-implant image of one or more electrode arrays implanted within patient 12 and stores the image. Image analysis unit 60 retrieves the electronic image of the electrical stimulation electrode array implanted within the patient 12 from lead image buffer 56 and analyzes the image to identify one or more physical characteristics of the implanted electrode array or arrays.

Characterization unit 62 receives the physical characteristics from image analysis unit 60 and compares them to physical characteristics of known electrode array types stored in characteristic data memory 58. Again, although leads will be described for illustration, electrode arrays may be implanted as part of leadless stimulators or other devices. Characterization unit 62 characterizes the electrode array based on the identified physical characteristics and automatically generates an indication of the characterization of the array. For example, characterization unit 62 may determine the types of one or more implanted leads based on the comparison of the physical characteristics produced by image analysis unit 60 to physical characteristics of different types of known leads. Hence, the characterization produced by characterization unit 62 may include a determination of the type of lead or leads in the implanted lead configuration.

To identify lead type, the physical characteristics used by characterization unit 62 may include one or more of an electrode number characteristic, electrode shape, an electrode size characteristic, and an intra-lead electrode spacing characteristic. The electrode number characteristic may indicate the number of electrodes on a given lead. The electrode size characteristic may be based on the width and/or length of each electrode, and may be represented by a ratio of electrode length to electrode width. The intra-electrode spacing characteristic may be based on the distance between adjacent electrodes on a lead, and may be represented by a ratio of electrode length to intra-lead electrode spacing. Electrode shape may include rectangular or circular shapes carried by some paddle leads. The aspect ratio of a rectangular profile may be different, depending on whether the rectangular shape of an electrode is produced from a two-dimensional view of a cylindrical ring electrode on a percutaneous lead, or whether the rectangular shape is the true rectangular shape of a flat rectangular electrode on a paddle lead.

In addition to determination of array types, e.g., lead types, characterization unit 62 may record the number of leads in the lead configuration. In particular, image analysis unit 60 may analyze an electronic image of multiple leads forming a lead configuration to identify one or more physical characteristics associated with the multiple leads. In addition, image analysis unit 60 may provide an indication of relative positioning of electrodes within the leads. Using information such as lead type, number of leads, and relative positioning, characterization unit 62 produces lead characterization output data that provides an indication of the lead characterizations for use by programmer 20 in recording the lead configuration, and presenting appropriate programming options and parameters for the pertinent lead configuration.

In some embodiments, image processing device 52 may arrange identified leads into groups, e.g., based on a distance threshold. For example, as mentioned previously, two leads with electrodes implanted near the T9 vertebra could be grouped together on the basis that they are closer to one another than they are to the leads implanted that target the lumbar region. Accordingly, image processing device 52 may identify the T9 and lumbar leads as two separate groups of leads. Programmer 20 may then use the group identifications to manage programming of the separate lead groups. For example, programmer 20 may display the separate groups independently of one another on different screens of the display device. Programmer 20 also may be configured to prevent a user from selecting electrode combinations that would include electrodes from separate lead groups.

Image processing device 52 may be configured to automatically identify other implanted hardware, such as leads, implantable stimulation generators, catheters, implantable drug pumps, lead anchors, lead extensions, or the like. Also, in some embodiments, image processing device 52 may be configured to automatically trace leads and/or lead extension wires back to device connections to determine which leads are coupled to which devices, and which ports in which devices.

Also, in some embodiments, image processing device 52 may be configured to automatically assess integrity of the leads, e.g., in terms of operational status. For example, image processing device 52 may automatically detect image patterns or signatures indicative of lead fractures, kinks or disconnections from the device header block may, and provide information to programmer 20 indicating detection of such features either separately or as part of the lead characterization information.

In various embodiments, programmer 20 may be configured to alter programming based on the image analysis by image processing device 52 and the lead characterization information generated from the image analysis. Programmer 20 may automatically adjust electrical stimulation therapy based on the image analysis, e.g., by setting initial electrical stimulation parameters or adjusting existing electrical stimulation parameters based on the analysis. In some cases, the adjustments may be based at least in part on one or more inter-electrode distances and/or one or more electrode sizes determined based on the analysis. In addition, programmer 20 may automatically generate a programming search sequence for electrode combinations for delivery of electrical stimulation therapy based on the analysis. For example, programmer 20 may select candidate electrodes for evaluation by the user, e.g., based on inter-electrode distances, distances relative to anatomical targets, or the like.

Also, programmer may automatically inhibit selection of particular electrode combinations for delivery of electrical stimulation therapy based on the analysis. For example, programmer 20 may exclude from consideration by the user electrode combinations including electrodes in different lead groups, electrodes that are too far apart, electrodes that are too close to one another, or electrodes that are too far away from or too close to particular anatomical structures. In this manner, programmer 20 may use the image analysis to inhibit or prevent nonsensical electrode selections or parameters given the particular lead configuration implanted within the patient. Hence, in various embodiments, image analysis may support a variety of guided programming features that may promote programming accuracy, efficiency and speed.

Figure 5C:
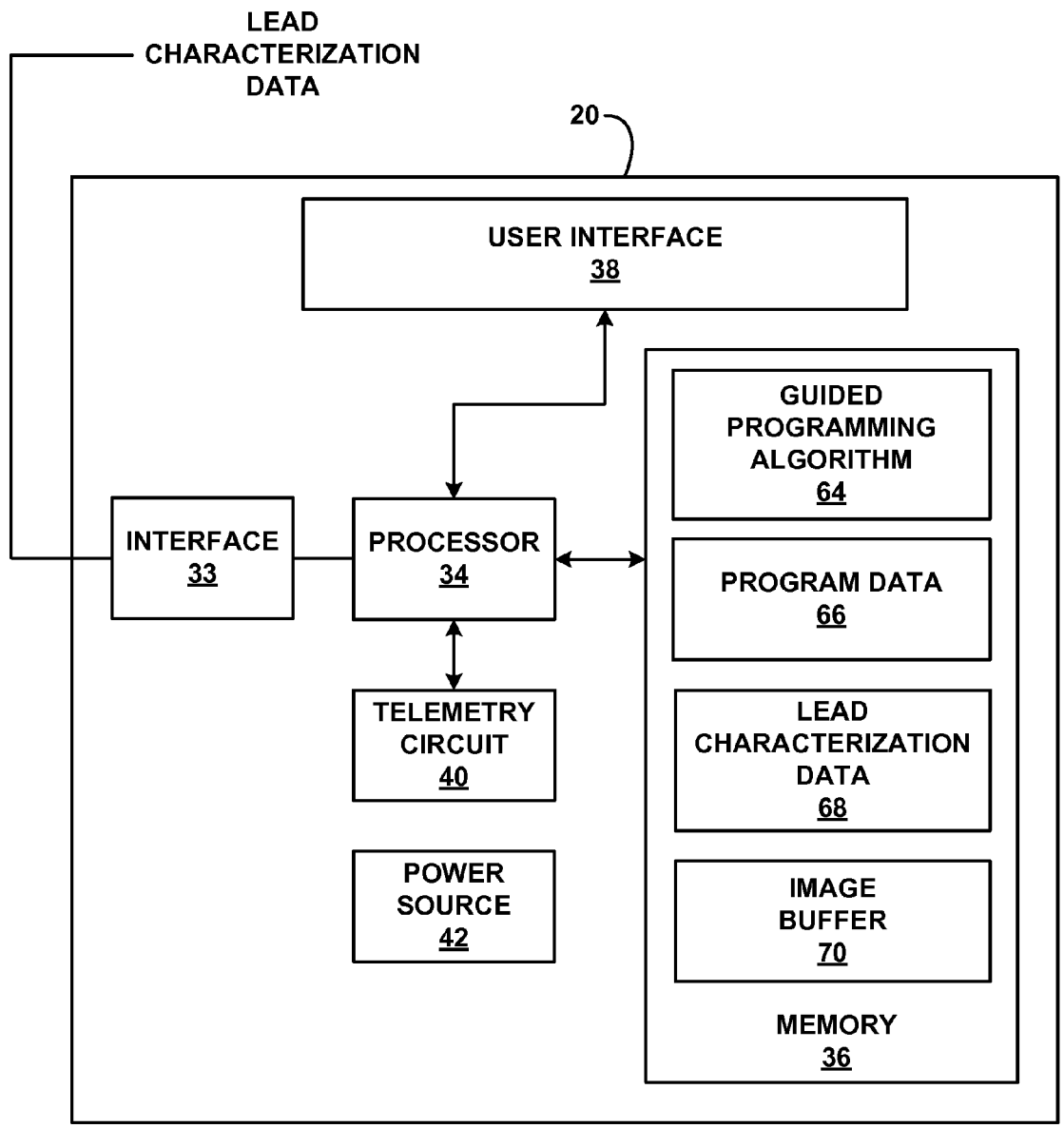
FIG. 5C is a block diagram illustrating example components of an electrical stimulation device programmer useful in adjusting patient therapy parameters based on the characterization of implanted electrode arrays.

FIG. 5C is a block diagram illustrating example components of an electrical stimulation device programmer 20 useful in generating adjustments to patient therapy parameters based on the characterization of implanted electrode arrays. Adjustments may include specification of initial parameter settings or modifications of initial settings. Programmer 20 shows an example of the programmer of FIGS. 3 and 5A in greater detail. In the example of FIG. 5C, processor 34 receives lead characterization data, e.g., from characterization unit 62 of image processing device 52. For example, programmer 20 may include an image analysis interface 33, such as a network controller, to receive the lead characterization data via network 54, or some other interconnection interface. Alternatively, in some embodiments, telemetry circuit 40 may function as an image analysis interface.

Processor 34 of programmer 20 obtains, via interface 33, an analysis of the electronic image of the implanted lead configuration, e.g., as represented by the lead characterization data produced by characterization unit 62. Based on the lead characterization data, processor 34 may present a representation of the implanted lead configuration via user interface 38. In addition, processor 34 may use the lead characterization data to specify the lead configuration for programming purposes. For example, processor 34 may automatically generate an adjustment to electrical stimulation therapy delivered via the lead configuration based on the analysis. The automatically generated adjustment may be applied automatically by programmer 20 to change one or more parameters associated with a program, or presented as a proposed adjustment for review and approval by a user prior to changing the program. Using the lead characterization data, programmer 20 also may present appropriate programming options for the lead configuration indicated by the lead characterization data.

The lead characterization data may include a determination of the configuration of the one or more implanted leads, such as lead types, lead orientations, lead positions, number of leads, and relative positions of the electrodes carried by the leads, based on the analysis by image analysis unit 60 and lead characterization unit 62. Accordingly, the adjustment may be automatically generated based on the configuration of the leads. The adjustment may include an adjustment of one or more parameters associated with the electrical stimulation therapy delivered via the lead. For example, the adjustment may include an adjustment of one or more electrode combinations associated with the electrical stimulation therapy delivered via the lead, and/or an adjustment of amplitude, pulse width, pulse rate, or the like.

Memory 36 of programmer 20 may store a variety of information for use by processor 34 in presenting programming options and other information to a user in order to program stimulation therapies delivered by the stimulator 14. In the example of FIG. 5C, memory 36 stores instructions to support execution of a guided programming algorithm 64, program data 66 generated or retrieved by processor 34 for control of stimulator 14, lead characterization data 68 obtained from image processing device 52, and an image buffer 70 for storage of electronic imagery representative of implanted leads and/or anatomical targets, e.g., as obtained by imaging modality 50 and provided to programmer 20 by imaging modality 50 or image processing device 52. Lead characterization data 68 obtained from image processing device 52 may include historical data from previous characterization efforts for the same lead array to aid in detecting lead migration.

Guided programming algorithm 64 may include instructions to cause processor 34 to perform various steps, procedures and operations to guide a user, via user interface 38, through a process of programming stimulation parameters for one or more stimulation programs to be used by stimulator 14. Processor 34 may use lead characterization data as input data for guided programming algorithm 64. Based on the lead characterization data, guided programming algorithm 64 may support presentation of an appropriate lead configuration and programming choices via user interface 38. A guided programming algorithm executed by processor 34 may use anatomy information such as distances between electrodes and target anatomy if such information is available. The guided programming algorithm also may use other types of information such as the degree of change of spacing between electrode pairs in different patient positions or postures. In this case, selection of electrode combinations that exhibit significant variation in inter-electrode spacing for positional or posture changes may be discouraged.

As an illustration, if the lead characterization data obtained from characterization unit 62 and stored in lead characterization data memory 68 indicates a trio of leads having four electrodes, eight electrodes and four electrodes, respectively, i.e., a 4-8-4 configuration, guided programming algorithm 64 may support visual presentation of a 4-8-4 lead configuration by user interface 38, and present possible programs, electrode combinations, and individual parameters appropriate for the lead configuration indicated by the lead characterization data.

If the lead characterization data includes relative positioning data, the visual presentation may also present relative positioning of the electrodes on the various leads. In addition, in executing guided programming algorithm, processor 34 may use the relative positioning information provided by the analysis of the electronic image of the implanted lead configuration to automatically generate adjustments to stimulation parameters, e.g., based on relative spacing between respective electrodes. The parameter adjustments may be applied automatically or may be subject to review and approval by a user via user interface 38, and stored with program data 66 for a pertinent program. In addition, in the course of programming, a user may evaluate programs and parameter adjustments by applying them to the patient via stimulator 14 and eliciting efficacy feedback from the patient.

Lead characterization data 68 stores lead characterization data obtained from image processing device 52. Program data 66 may store data relating to default programs, programs previously prepared by the user, and programs newly prepared by the user via guided programming algorithm 64. Programmer 20 may download some or all of the programs in program data 66 to an implanted, implantable, or external stimulator 14. The stored program data 66 may define parameters for electrical stimulation including one or more of amplitude, pulse rate, pulse width, electrode combination and electrode polarity. In conjunction with guided programming algorithm 64 and lead characterization data 68, processor 34 may enforce programming rules such that the program data 66 is consistent with the lead configurations indicated by the lead characterization data 68.

In some embodiments, program data 66 also may store rating data that indicates perceived therapeutic efficacy for the various programs, e.g., based on patient feedback and/or other factors such as power efficiency. Also, program data 66 may be organized in a variety of ways. For example, programs may be arranged according to different categories of symptom relief, such as leg pain, torso pain, back pain, or the like, and may be applied independently or in combination with one another on a simultaneous or interleaved basis. In each case, guided programming algorithm 64 may ensure that the programs are consistent with the lead configuration indicated by the lead characterization data 68. For example, if the lead configuration is 4-8-4, then the programming options presented to the user should not specify electrode combinations for an 8-8 lead configuration.

Image buffer 70 may store image data representing one or more post-implant images of the leads implanted within the patient. The image data may be obtained directly from imaging modality 50 or from image processing device 52. In some embodiments, the image data may be provided as part of the lead characterization data, and may be provided at less than the full spatial resolution of the original image data obtained by imaging modality 50 and processed by image processing device 52. In some embodiments, a user of programmer 20 may selectively view a graphical representation of the lead configuration produced according to guided programming algorithm 64 or an actual image produced based on the image data in image buffer.

A reduced resolution version of the image data may facilitate transmission storage of the image data in memory 36 and presentation of the imagery via user interface 38. The imagery also may be presented in other altered forms, in addition or as an alternative to reduce resolution. For example, the imagery may be cropped, enhanced in contrast or brightness, rotated, sharpened, or the like. In some cases, the image may be presented independently or in combination with a graphic representation of the lead configuration via a display associated with user interface 38. Also, in some embodiments, the image data in image buffer 70 may be used to present anatomical targets in combination with a graphic representation of the lead configuration. Alternatively, anatomical targets may be graphically depicted based on lead characterization data or based on user input specifying proximity to anatomical targets, e.g., by positioning graphical depictions of anatomical targets relative to graphical depictions of lead configurations in a manner consistent with the actual post-implant imagery.

Figure 6:
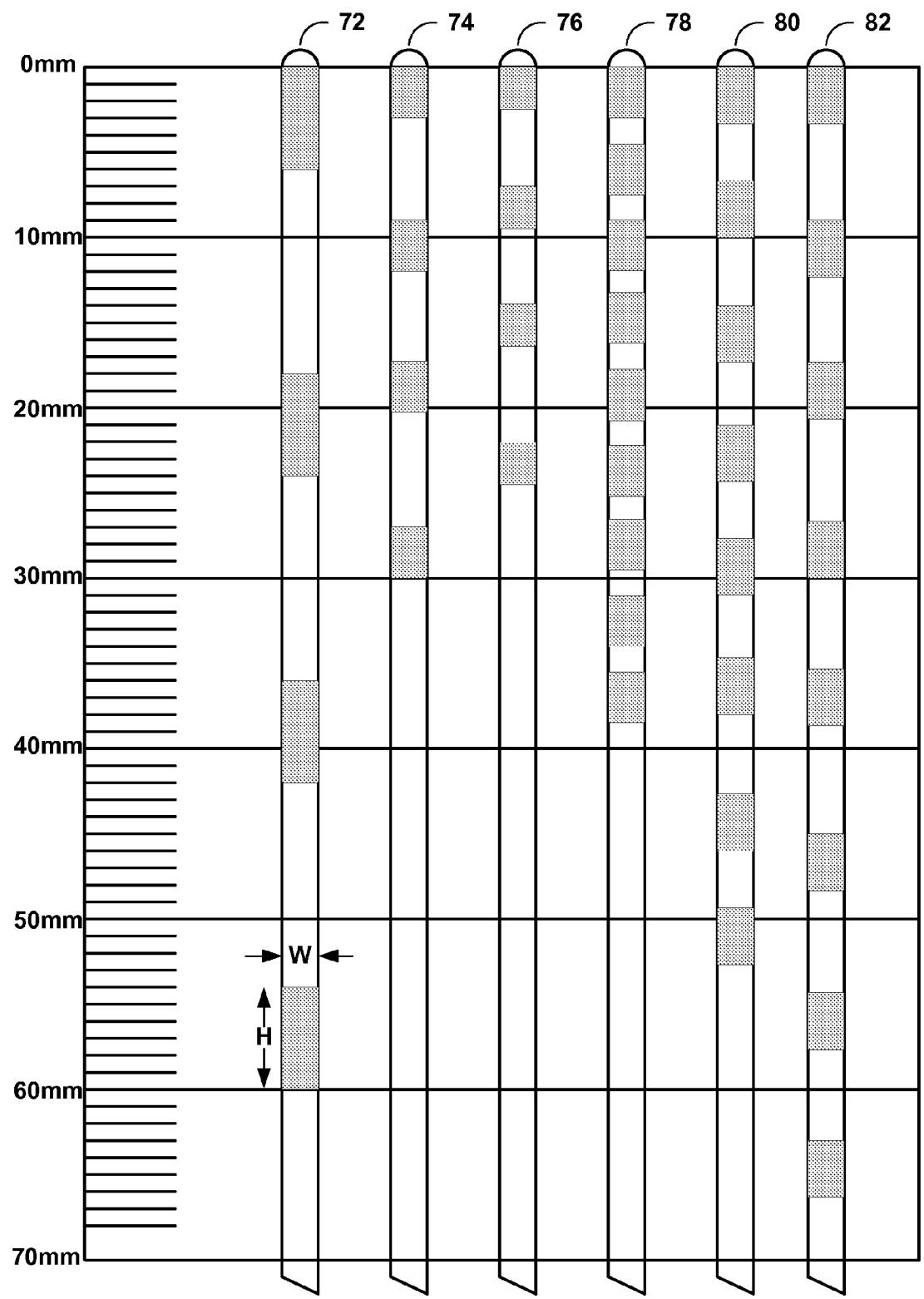
FIG. 6 is a schematic diagram illustrating a variety of different example lead types, including different electrode counts, sizes, positions and intra-lead electrode spacing.

FIG. 6 is a schematic diagram illustrating a variety of different example lead types, including different electrode counts, sizes, positions and intra-lead electrode spacing. FIG. 6 includes a length scale from 0 to 70 millimeters (mm) to illustrate the widths and positions of electrodes for the various lead types. In operation, image analysis unit 60 of image processing device 52 processes and analyzes the electronic, post-implant image to identify one or more physical characteristics of the implanted lead configuration. Characterization unit 62 compares the physical characteristics to those of known lead types, e.g., by reference to sets of characteristics in characteristic data memory 58. FIG. 6 shows examples of six different lead types that may be implanted individually, in combination with one or more other leads of the same lead type, or in combination with one or more other leads of different lead types.

In the example of FIG. 6, lead 72 represents a Medtronic Quad Plus lead, lead 74 represents a Medtronic Pisces Quad® lead, lead 76 represent a Medtronic Pisces Quad® Compact lead, lead 78 represents a Medtronic 1×8 Subcompact lead, lead 80 represents a Medtronic 1×8 Compact lead, and lead 82 represents a Medtronic 1×8 Standard lead. Notably, the different types of leads 72-82 are characterized by different electrode counts, e.g., four versus eight, different electrode lengths, e.g., 3 mm versus 6 mm, and different intra-lead electrode spacing, e.g., 12 mm versus 6 mm versus 4 mm versus 1.5 mm.

The leads in FIG. 6 are examples of known percutaneously implantable leads with known lead and electrode geometries. Percutaneously implantable leads are described for purposes of illustration. Various techniques described in this disclosure may be applied to other types of leads, such as surgically implanted leads. Other types of leads, including leads marketed by Medtronic or other manufacturers, may be represented by data stored in characteristic data memory 58 to permit ready identification of implanted leads by characterization unit 62. In addition, data may be stored by image processing device 52 and/or programmer 20 to represent other types of devices, such as lead anchors, lead extensions, lead adaptors, implantable stimulators, implantable drug delivery devices, spinal hardware, such as screws or cages, or other devices. Accordingly, the leads shown in FIG. 6 are exemplary and should not be considered limiting in any way. The dimensions for leads of FIG. 6 are given in Table 1 below, with the characteristics of leads 72-82 being represented from left to right. All dimensions in Table 1 are in millimeters (mm) and are exemplary.

TABLE 1

| | Lead Number | | | | | |
|---|---|---|---|---|---|---|
| | 72 | 74 | 76 | 78 | 80 | 82 |
| Electrode Width (mm) | 1.5 | 1.5 | 1.5 | 1.5 | 1.5 | 1.5 |
| Electrode Length (mm) | 6 | 3 | 2.5 | 3 | 3 | 3 |
| Electrode Spacing (mm) | 12 | 6 | 5 | 1.5 | 4 | 6 |
| Number of Electrodes | 4 | 4 | 4 | 8 | 8 | 8 |
| Ratio of Electrode Width to Electrode Length | 1.5/6 = 0.25 | 1.5/3 = 0.5 | 1.5/2.5 = 0.6 | 1.5/3 = 0.5 | 1.5/3 = 0.5 | 1.5/3 = 0.5 |
| Ratio of Electrode Length to Electrode Spacing | 6/12 = 0.5 | 3/6 = 0.5 | 2.5/5 = 0.5 | 3/1.5 = 2 | 3/4 = 0.75 | 3/6 = 0.5 |

In Table 1 above, electrode width refers to the width of the lead, and hence the width of the electrode carried by the lead, if the lead were taken in cross-section along a longitudinal axis of the lead. Width is denoted by W in FIG. 6 with respect to lead 72. Electrode length refers to the length of each electrode in the direction of the longitudinal axis of the lead, and is denoted by L in FIG. 6 with respect to lead 72. Electrode spacing refers to the intra-lead electrode spacing between adjacent electrodes on a given lead. Number of electrodes refers the electrode count for each lead, e.g., four for leads 72, 74, and 76, and eight for leads 78, 80, and 82. Ratio of electrode width to electrode length and ratio of electrode length to electrode spacing provide physical characteristics that can be used to define lead/electrode geometry and facilitate identification of lead type by characterization unit 62.

If image analysis makes use of three-dimensional (3D) images or models, analogous measurements can be used. Instead of width, diameter or radius of a cylindrical electrode could be used for 3D analysis to distinguish different electrode sizes. Spacing could be measured from centroid to centroid of cylindrical electrodes, rather than edge to edge or center to center in two-dimensional (2D) analysis. Because the important metrics may be ratios in various embodiments, specific units of measure may not be material as long as all measures make use of the same units.

Characterization unit 62 (FIG. 5B) may access characteristic data memory 58 to obtain one or more physical characteristics, such as those illustrated in FIG. 6 and described above with respect to Table 1, in order to characterize a lead versus known lead types. Alternatively, a lead may be characterized independently of known lead types. However, characterization versus known lead types may be more efficient, and permit lead characterization with better confidence and accuracy. Hence, characterization unit 62 may generate lead characterization data that simply includes an indication of lead type, the number of leads of each lead type in a lead configuration, and relative positioning of the leads or the electrodes carried by the leads.

Alternatively, as another example, instead of lead type, lead characterization data may include electrode count, size, and intra-lead electrode spacing data for each lead, and relative positioning of the leads or electrodes carried by the leads. Programmer 20 may use such information to build a representation of a lead configuration. However, it may be more desirable to access a representation of a known lead configuration using the lead information. Relative positioning of leads may be presented by positional indices, such as 0, 1, 2, etc., to indicate lead positions from left to right at the implant site. In addition, relative positioning of leads and/or electrodes may be represented by absolute positions within a coordinate system or relative distances between leads and/or electrodes. Lead characterization data may be presented in a variety of different ways. Accordingly, the illustrations of lead characterization data provided above should not be considered limiting of the techniques described in this disclosure.

Figure 7:
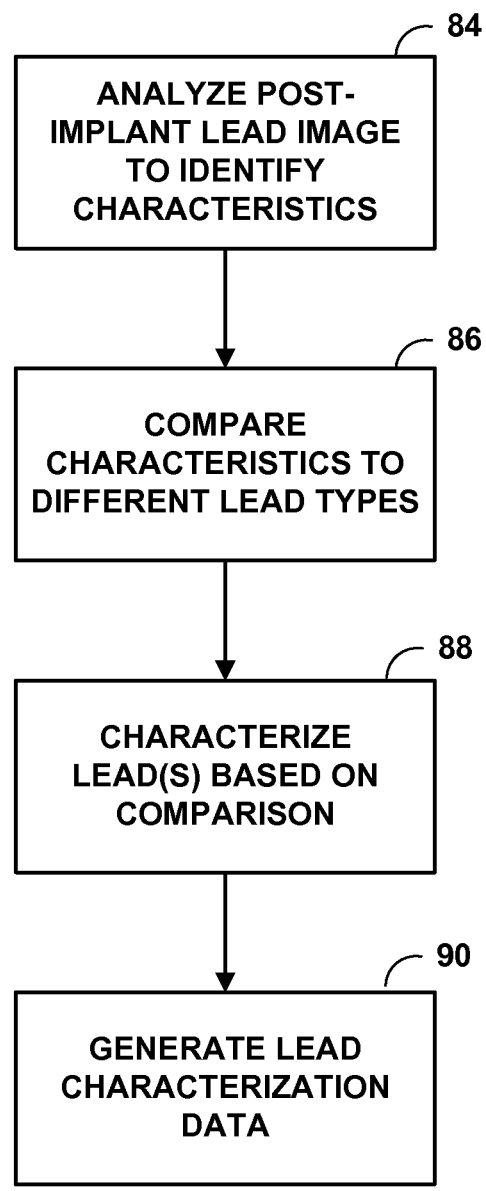
FIG. 7 is a flow chart illustrating an example technique for generating a lead characterization using analysis of post-implant imagery.

FIG. 7 is a flow chart illustrating an example technique for generating a lead characterization using analysis of post-implant imagery. In the example of FIG. 7, image processing device 52 analyzes a post-implant lead image obtained by image modality 50 to identify one or more physical characteristics of the lead (84). Image processing device 52 compares the one or more physical characteristics identified from analysis of the image to similar physical characteristics for a set of different, known lead types (86). Based on the comparison, image processing device 52 characterizes the implanted lead configuration (88), e.g., by indicating the lead type and relative positions of the leads and associated electrodes. The lead characterization may include, as an alternative or in addition to lead type, one or more of the physical characteristics such as electrode count, size, and spacing, shape, identifier marks or fiducials, anatomical landmarks, as well as physical ratios derived for the leads, e.g., as shown in Table 1. Image processing device 52 generates lead characterization data for the implanted lead configuration (90). The lead characterization data may be stored and/or provided to external programmer 20 for use in programming an electrical stimulator 14 to deliver electrical stimulation therapy via the implanted lead configuration.

Figure 8:
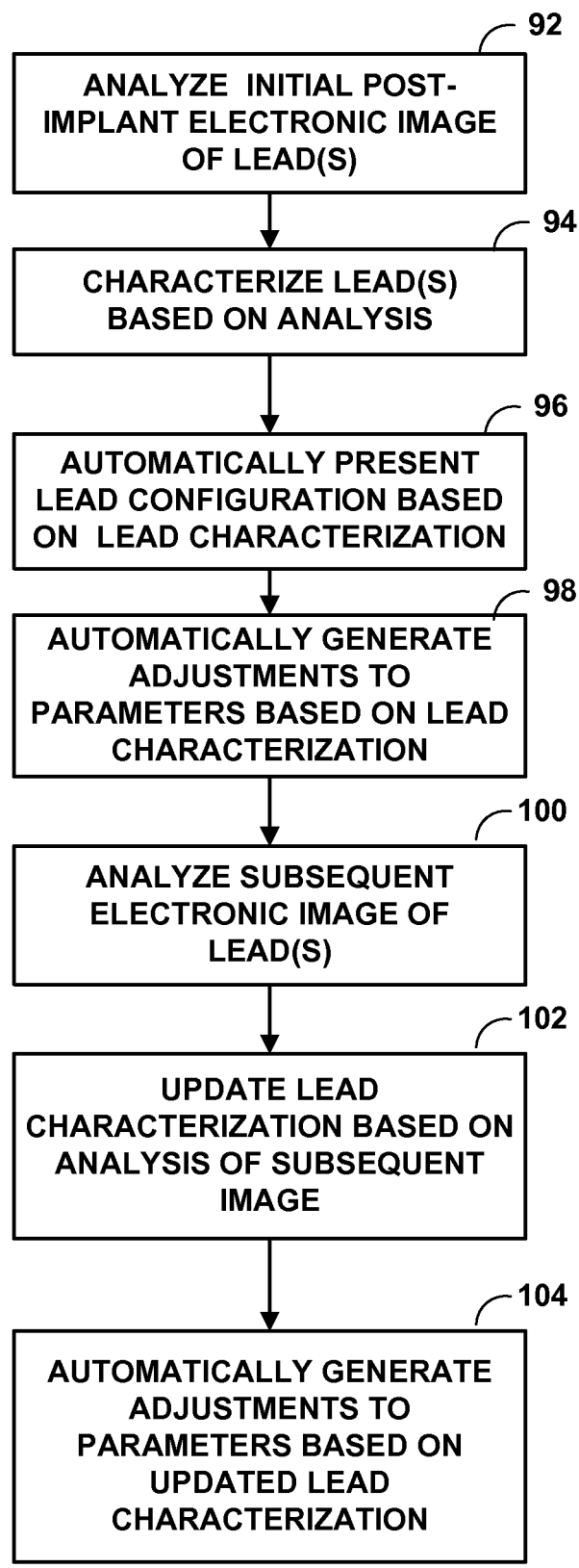
FIG. 8 is a flow chart illustrating an example technique for specifying electrical stimulation parameters based on a lead characterization obtained from analysis of post-implant imagery.

FIG. 8 is a flow chart illustrating an example technique for adjusting electrical stimulation parameters based on a lead characterization obtained from analysis of post-implant imagery. Using lead characterization data, external programmer 20 may present suitable programming options and parameters, consistent with the lead configuration indicated by the lead characterization data. In the example of FIG. 8, image processing device 20 analyzes an initial post-implant electrode image of the implanted leads (92) and characterizes the leads based on the analysis (94), e.g., in a manner similar to that described with reference to FIG. 7.

External programmer 20 may store lead characterization data for review by the user and for use in programming stimulator 14. In addition, based on the lead characterization, external programmer 20 may automatically present the lead configuration to a user via the user interface of the programmer (96). For example, external programmer 20 may display a graphical depiction of the lead configuration and permit the user to interact with the graphical depiction, e.g., by touchscreen or other input media, to specify electrode combinations and parameters.

In presenting the lead configuration (96), programmer 20 may present programming options that are appropriate for the lead configuration indicated by the characterization data. For example, as part of a guided programming algorithm, programmer 20 may permit the user to select only electrode combinations and parameters that are actually supported by the lead configuration indicated by the characterization data. If the lead configuration includes a combination of only two leads, each carrying four electrodes, programmer 20 does not permit, or present as a possibility, electrode combinations that would involve electrodes on three different leads, or combinations that would involve electrodes at intermediate positions that could be realized by an eight-electrode lead but not a four-electrode lead. In this manner, programmer 20 may automatically generate appropriate programming options for the identified lead configuration without the need for the user to enter lead configuration data, thereby reducing user effort and promoting accuracy. In addition, in some embodiments, the lead characterization data may be supplemented by actual relative position data, further promoting accuracy and therapeutic efficacy.

Based on the lead characterization data, which may optionally include relative position data, programmer 20 may also automatically generate adjustments to stimulation parameters (98). For example, with or without user direction, programmer 20 may retrieve any of a variety of base or default programs for the identified lead configuration. The base programs may specify different electrode combinations and parameters for delivery of electrical stimulation via the electrode combinations. Programmer 20 may select a list of such base programs identified as appropriate for the lead configuration. In addition, if the lead characterization data includes relative position information, programmer 20 may automatically specify the stimulation parameters according to the position information.

For example, programmer 20 may adjust the base program parameters based on the position information to compensate for actual distances between electrodes on different leads. If the base program assumes a default distance, for example, an amplitude parameter could be increased if the actual distance if larger than the default distance. Similarly, if the actual distance is smaller than the default distance, then programmer 20 may automatically reduce the amplitude parameter. Programmer 20 may be configured to automatically adjust other parameters, in addition to amplitude, based on lead configuration and relative position information. Programmer 20 may download the adjustments to stimulator 14 either automatically or upon user review and approval.

A variety of possible adjustments of stimulation based on lead characterization and relative electrode positioning may be provided. As an example, programmer 20 may adjust amplitude upward (increase amplitude) based on increased spacing between electrodes, or downward (decrease amplitude) based on decreased spacing between electrodes. As another example, amplitude may be adjusted upward or downward if spacing between electrodes and an anatomical target increases or decreases, respectively. If one or more different leads are implanted to replace or supplement one or more previously implanted leads, amplitude may be adjusted by programmer 20 to account for different surface areas of electrode contacts associated with different types of leads. In some embodiments, a lead characterization may include an indication of electrode shapes, sizes and/or surface area. If surface area increases or decreases, amplitude may be decreased or increased, respectively. In addition, if one or more different leads are implanted to replace or supplement one or more previously implanted leads, amplitude may be adjusted by programmer 20 to account for different properties of the leads themselves. For example, amplitude may be automatically increased when a low impedance lead is replaced by a normal impedance lead.

As a further example, if one or more different leads are implanted to replace or supplement one or more previously implanted leads, stimulation amplitude or pulse width may be adjusted to account for charge density limits that may be dependent on electrode geometry or size. Also, default or previously used combinations of electrodes may be changed due to offset leads at implant or due to lead migration. For example, a transverse tripole that normally starts at the 0-0+, 1-0−, 2-0+ might instead start at 0-0+, 1-0−, 2-1+ if lead 2 is shifted upwards one level. In the above notation, 0-0 refers to the most proximal electrode on a first lead (Lead 0), 1-0 refers to the most proximal electrode on a second lead (Lead 1), and 2-0 refers to the most proximal electrode on a third lead (Lead 2). Similarly, 2-1 refers to a second most proximal electrode on the third lead. The + and − signs indicate whether the electrode combination establishes a cathode or anode, respectively, at a particular electrode in the combination.

For a current-based stimulator in which electrical stimulation current pulses are delivered simultaneously, the percentage of activation may change with changes in relative spacing between electrodes. In this case, the activation levels of a +−+ electrode combination could be adjusted to 30%+, 100%−, 70%+ for the electrodes on left, center and right leads, respectively, if the center lead were nearer to the left lead than the right. In this case, the activation percentage of the electrode left lead could be less than the electrode on the right lead because it is closer to the electrode on the center lead. In the above notation, +−+ refers to a combination of electrodes having a current source electrode on a left lead, a current sink electrode on a center lead and a current source electrode on a right lead. The percent of activation may refer to a percentage of a maximum current level to be sourced or sinked by a respective electrode. In general, the percentages delivered via the left and right leads are unbalanced as a result of the unbalanced spacing between the left and center leads and the right and center leads.

In some embodiments, programmer 20 may be configured to limit programming options due to electrodes being too far apart and therefore ineffective, too close to one another and therefore inefficient, or in different identified groups of leads. If electrodes are in different identified groups, for example, they may be associated with leads that are implanted relative to different anatomical targets. Also, programmer 20 may be configured to present programming options or messages that discourage use of particular electrodes to high positional or posture-based variability of the electrode positions. In addition, programmer 20 may be configured to disallow programming options due to proximity of one or more electrodes to undesirable stimulation targets. As a further feature, programmer 20 may be configured to support directional programming tools to adjust amplitude up or down if parts of leads are known to be farther from or closer to, respectively, a target anatomy.

A program group may define delivery of different stimulation programs simultaneously or on a time-interleaved basis. Each program may define different stimulation parameters, such as amplitude, pulse width, pulse rate, electrode combination, and the like. The order of activation and inter-program activation delay of multiple programs in a single group of programs delivered by the implantable stimulator may be altered to optimize recruitment of particular fibers, tissues and/or muscles. For example, in dysphagia, swallowing is a pattern of recruitment. In this case, the order in which programs (in a program group) are turned "on" and the time between each program as they are turned "on" may be important to ensuring a successful swallow. Electrode settings and/or amplitude settings may be adjusted to accommodate lead position changes due to migration. Alternatively, or additionally, lead size/spacing information obtained from image processing device 52, in conjunction with anatomical information, may be used to suggest optimal timing between programs.

The lead characterization data alternatively or additionally may include information that indicates positioning of leads and/or electrodes relative to one or more anatomical targets, such as particular vertebrae associated with the spinal cord. The anatomical positioning information may be generated automatically, e.g., by automated recognition of anatomical targets or features such as radio-opaque markers associated with such targets. Alternatively, a user of image processing device 52 or programmer 20 may supplement the lead characterization data with such positioning information, e.g., by measurements during surgery or human inspection of post-implant imagery.

Also, bone shapes may be visible in images, and can be used to estimate proximity to particular anatomical targets. Formulas for adjustment of stimulation parameters may be applied based on some easily identifiable landmarks (e.g., AC-PC line for STN stimulation). Other imagery, on which it is easier to view target anatomy, may be overlayed with imagery of the lead configuration. Also, anatomical atlas approaches, possibly with patient specific warping, could be used.

With the aid of anatomical positioning information, programmer 20 may automatically generate further adjustments to one or more parameters, either for automatic application or application upon review and approval by the user. If the anatomical positioning information indicates that the distance of one or more electrodes in an electrode combination to an anatomical target is longer or shorter than a default distance of distance range, then programmer 20 may automatically adjust an amplitude or other parameter upward or downward, respectively.

Also, programmer 20 may be configured to automatically generate different electrode combinations if the distance of current electrode combination to an anatomical target is not deemed sufficient for reliable therapeutic efficacy, or perhaps less efficacious that another electrode combination considered more optimal. In some embodiments, programmer 20 may distinguish between adjustments based on lead configuration positioning, i.e., relative positioning of leads and/or electrodes relative to each other, and anatomical positioning, i.e., positioning of leads and/or electrodes relative to one or more anatomical targets. In this manner, the user may consider and approve such adjustments separately.

In addition to specifying lead configuration and parameters, programmer 20 may be configured to accept updated lead characterization data at a later time in order to accommodate possible lead migration. For example, at some time after initial implantation, e.g., days, months or years, a patient may return to the clinic to permit imaging modality 50 to obtain one or more subsequent electronic images of the implanted lead configuration. Image processing device 52 then may analyze the subsequent electronic image or images (100), and automatically generate an updated lead characterization (102) based on the analysis of the subsequent electronic image.

Assuming there has been no subsequent implant procedure to replace or modify the originally implanted leads, the updated lead characterization should indicate the same lead types. Due to lead migration, however, the actual relative positioning between the leads and electrodes carried by the lead may have changed. In this case, the updated lead characterization data may include updated relative position information. Based on the updated lead characterization data, programmer 20 may automatically generate adjustments to existing programs delivered via the implanted lead configuration (104), e.g., with or without user review and approval. Image processing device 52 may be configured to distinguish between lead migration and revised or newly implanted leads.

In this case, programmer 20 may be configured to present a notification to a user advising of a revised or newly implanted lead.

If lead migration resulted in an increase or decrease in the distance between electrodes in an electrode combination, for example, programmer 20 may adjust amplitude upward or downward, respectively, to compensate for the migration. Other parameters, alternatively or additionally, may be adjusted based on lead migration indicated by the updated lead characterization data. Alternatively, or additionally, programmer 20 may adjust, as a parameter, the electrode combinations associated with one or more programs. For example, if leads have moved vertically, horizontally, or diagonally relative to one another, it may be appropriate to select different combinations of electrodes rather than adjust parameters of stimulation delivered by an existing electrode combination. In each case, the modified parameters may be applied to stimulator 14 either automatically or upon user review and approval. In addition, a user may be permitted to evaluate the proposed adjustments to elicit efficacy feedback from the patient. To select a new electrode combination in the case of migration, programmer 20 may identify a target zone stimulated by the original electrode combination prior to migration, determine coordinates of the target zone, map those coordinates to the new, post-migration lead geometry, and select the best correspond electrodes to use to stimulate the target zone.

Figure 9:
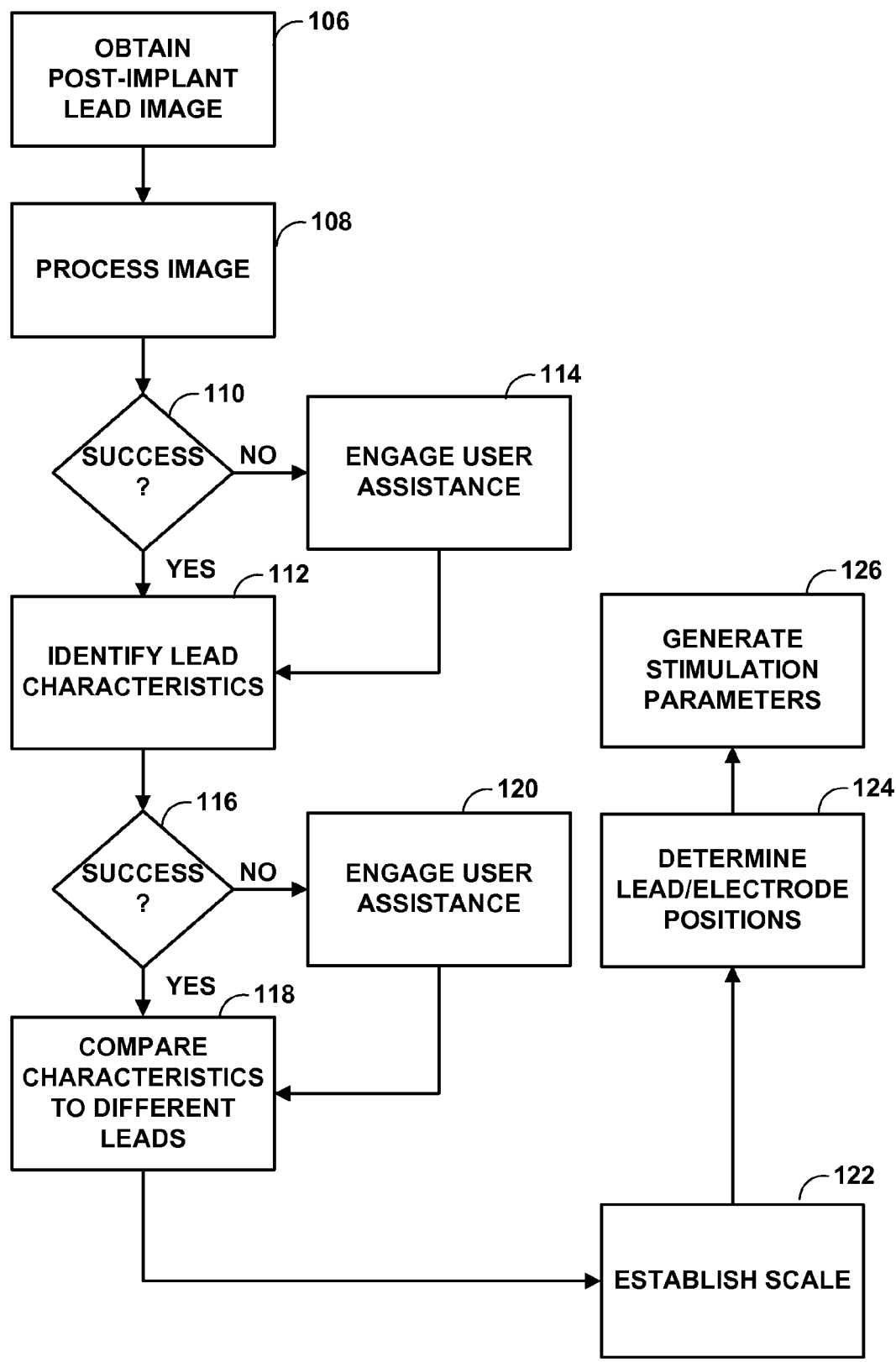
FIG. 9 is a flow chart illustrating an example technique for generating a lead characterization and generating adjustments to stimulation parameters in greater detail.

FIG. 9 is a flow chart illustrating an example technique for generating a lead characterization and specifying stimulation parameters in greater detail. The example of FIG. 9 indicates stages of the image analysis process that may be aided by user intervention. As shown in FIG. 9, imaging modality 50 obtains the post-implant lead image (106). Image modality 50 may provide the post-implant lead image to image processing device 52, where the image is stored in image buffer 56. Image processing device 52 processes the image (108), e.g., in image analysis unit 60. As will be described, image processing may include assigning an x-axis and a y-axis coordinate origin to the post-implant lead image (e.g., the origin may be the bottom left corner of the image), converting the image to a black and white contrast image, analysis of pixels to identify electrodes and establishment of a pixel to distance dimensional scale to determine actual relative positioning of electrodes. If image processing is not successful (NO of 110), image processing device 52 may generate a request to engage user assistance (114).

Image processing may be unsuccessful when, for example, the number of electrodes identified are too few or too numerous to determine a lead type in a reliable manner. As another example, image conversion to black and white may result in introduction of artifacts that appear as electrodes, or eliminate actual electrodes. In each case, the user may be called upon to review the image and provide user input to assist in image processing. As an example, the user input may specify whether particular features are electrodes that should be considered as lead characteristics or artifacts that should be ignored. The user may also manually adjust the image contrast, brightness or other characteristics to aid the image processing operation. As one illustration, a user may be asked to draw a bounding box around the leads, e.g., using a mouse, stylus, or other pointing tool, so that extraneous sections of the image may be discarded from consideration. As another illustration, a user may be asked to identify the center of all the electrodes. The user may utilize the mouse, stylus, or other pointing tool to indicate the center of one or more of the electrodes. In one example, image buffer 56 within image processing device 52 may store the locations of the user-identified centers. The locations of the user-identified centers may be stored in terms of coordinates relative to an origin of the implant image.

Next, using the processed image, image processing device 52 analyzes the image to identify physical lead characteristics (112) such as lead count, electrode count, electrode size and electrode spacing, and number of leads. In addition, as lead characteristics, image processing device 52 may generate ratios such as length to width ratios similar to those shown in Table 1 above. Identification of lead characteristics may be unsuccessful when, for example, leads overlap each other, are substantially displaced from one another, are positioned so closely that it is difficult to determine the spacing between the leads, or are positioned so closely that it is difficult to determine where one electrode ends and another begins.

If identification of lead characteristics is not successful (NO of 116), image processing device 52 may generate a request to engage user assistance for identification of lead characteristics (120). In this case, the user may provide user input to image processing device 52 to aid in identifying lead characteristics. For example, the user may inspect a displayed version of the image and enter lead characteristic data such as lead types, lead count, electrode count, electrode size, and intra-lead electrode spacing. In some embodiments, the image may be displayed with a size scale to permit the user to provide absolute or relative size and spacing parameters. As another example, in some embodiments, the user may be asked to draw a trace of each lead for use by image processing device 52 in determining lead characteristics. With such a trace or traces, image processing device 52 may be better able to identify the particular electrodes associated with each lead. As yet another example, in some embodiments, the image may be displayed with coordinates of the center of the electrodes to permit the user to provide electrode size and spacing parameters relative to the displayed coordinates.

Upon identification of lead characteristics, either automatically or with the user assistance, image processing device 52 may compare the lead characteristics to those of different known leads (118) in order to identify the types of leads in the implanted lead configuration. For example, various lead characteristic ratios as shown in Table 1 may be compared to lead characteristic ratios of known lead types. The implanted lead may be equated to a known lead with substantially similar lead characteristics. In this manner, the implanted lead may be determined to be the known lead type with substantially similar lead characteristics.

After the implanted lead or leads are determined to be of a known lead type or types, a pixel dimension may be calculated to establish a scale for determination of actual relative positioning of leads and/or electrodes (122). The pixel dimension is the actual length or width of a pixel in the image of the implanted electrode array. Alternatively, in a 3D setting, voxel dimensions may be determined. The pixel dimension may be calculated, for example, by equating the number of pixels necessary to display a lead characteristic to the actual dimension of that lead characteristic. For example, the number of pixels used to present the width of an electrode may be equated to the actual dimension of the electrode width.

The pixel dimension scale may then be calculated by dividing the actual dimension of the electrode width, which may be known by the actual electrode width associated with a known lead type, by the number of pixels used to present the electrode width. As an illustration, if the width of an electrode is 1.5 mm, and the number of pixels extending along the width of the electrode is 10 pixels, then the pixel dimension is 1.5 mm divided by 10 pixels, which is equivalent to 0.15 mm per pixel. Electrode length or spacing, as well as other lead characteristics, may be similarly used to determine pixel dimension and establish a dimensional scale of pixels for the electronic image. The dimensional scale can then be used to determine actual relative positioning of electrodes based on pixels corresponding to the electrodes and the dimensional scale.

In some embodiments, dimension estimates determined from different characteristics of electrodes or leads may be compared as an accuracy cross-check. In other words, the accuracy of the characterization of a lead or lead configuration may be verified, e.g., by the image analysis unit, based on comparison of metrics derived from different physical characteristics of the electrode array. For example, a metric such as a millimeter scale derived from the number of pixels forming electrode height should match the millimeter scaled derived from the number pixels forming electrode width. In particular, the pixel per mm scale should substantially match. Also, scales derived from different leads should substantially match. If different scales are detected, it may be highly likely that the image processing operation has encountered an error. In this case, the user may be notified by image processing device 52, programmer 20 or both.

In summary, a type of lead may be identified by relative characteristics, such as a ratio of electrode width to electrode length and/or a ratio of electrode length to electrode spacing, e.g., as shown in Table 1. Hence, lead type identification can be made based on the ratio of the numbers of pixels associated with the electrode width, electrode length and/or spacing. Once the lead type is known, the actual electrode width and length are known because the type of lead and its characteristics are known. Then, the pixel dimension can be determined as indicated above. After the pixel dimension is calculated, the relative positions of the leads and/or electrodes may be determined by image processing device 52 (124).

The actual relative positions of the leads and/or electrodes may be calculated by determining the number of pixels between the leads and/or electrodes and multiplying that number by the pixel dimension. In this manner, the actual distances between leads and/or electrodes can be calculated. Programmer 20 then may automatically specify stimulation parameters (126) to be delivered via particular electrode combinations. Given the actual relative positioning information, as part of the lead characterization information, programmer 20 may generate one or more stimulation parameters appropriate for the lead configuration and the distances between electrodes forming an electrode combination.

Various operations and procedures for processing and analyzing a post-implant image to produce a lead characterization will now be described in more detail. Upon obtaining an image from imaging modality 50, image processing device 52 may convert the image from imaging modality to a gray scale image in the event the original image was stored as red-green-blue (RGB) color pixel data. In other words, if each pixel in the image is represented with an RGB value, image processing device 52 may convert the three R, G and B color values of each pixel to a single gray scale value. As an example, imaging processing device 52 may convert the RGB color values for a pixel to gray scale values using the following equation:

$$\text{Gray} = (\text{Color(red)} + \text{Color(green)} + \text{Color(blue)})/3 \qquad a$$

The above technique of converting to RGB pixel data to a gray scale image value is merely exemplary. Accordingly, other techniques may be used.

Figure 10:
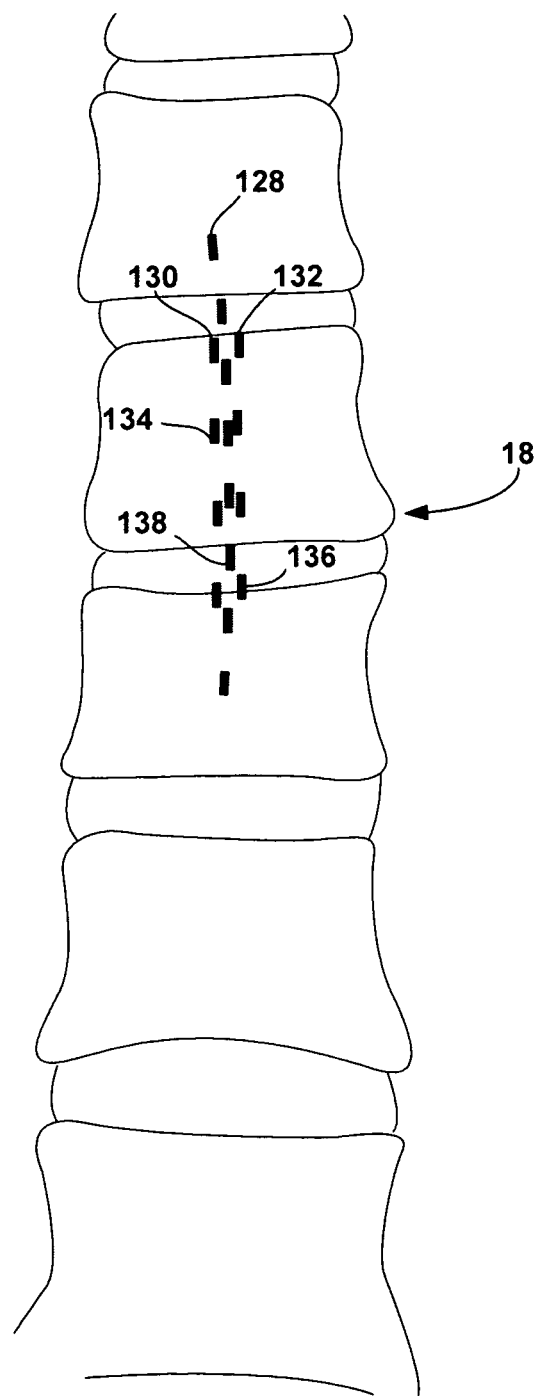
FIG. 10 is an example of an electronic post-implant image of a set of three implanted stimulation leads.

FIG. 10 is an example of an electronic post-implant image of a set of three implanted stimulation leads presented as a gray scale image. In FIG. 10, the three leads extend vertically along spinal cord 18, which is partially visible in the image. Hence, FIG. 10 is an example of an image of an implanted lead configuration for spinal cord stimulation (SCS). The three leads in FIG. 10 are generally identified as leads 128, 130, and 132. Some of the electrodes associated with leads 128, 130, and 132 are identified by reference numerals 134, 136, and 138, respectively. In general, the electrodes form vertical columns that correspond to their respective leads. Left-most lead 130 and right-most lead 132 each include four electrodes, and central lead 128 includes eight electrodes.

After converting the original RGB image to a gray scale image, image processing device 52 may convert the gray scale values to a binary (black/white) picture. Image processing device 52 may convert the image to a binary picture by, for example, threshold filtering. Threshold filtering may involve comparing the gray scale value for each pixel of the image to a threshold value. If the gray value for a given pixel is less than the threshold, that pixel may be assigned a "1." A value of "1" may designate that the pixel is associated with an object in the foreground. In general, electrodes on the leads typically appear as high contrast areas and may be darker than other portions of the image. Therefore, this process will cause the electrodes to stand out relative to the background such that each pixel assigned a "1" may be a pixel of an electrode. If the gray value of a pixel is greater than the threshold, that pixel may be assigned a "0." A value of "0" may designate that the pixel is in the background, and does not form part of a dark electrode. The above description refers to a fixed threshold. However, threshold filtering may be fixed or adaptive. In an adaptive version of threshold filtering, image processing device 52 may make use of a histogram of the gray values in the image and select a value that is a percentage of the peak of the histogram. The histogram may be bimodal where the peaks are relatively far apart. In some examples, the threshold value typically lies in the global minimum between the bimodal peaks. Other techniques of converting the gray scale to a binary (black/white) image may be used.

However, in some examples, electrodes on the leads may not appear as high contrast areas and may not be much darker than other portions of the image. In these examples, no threshold value for the adaptive version of threshold filtering may be found. In such situations, in the adaptive version of threshold filtering, the histogram may generate only one peak instead of bimodal peaks. In such examples, a threshold value may be manually selected using trial and error to convert the gray scale to a binary (black/white) image. However, even with trial and error, a threshold value may, in some instances, not be found because there may not be enough contrast between the electrodes and portions of the image. As described in more detail below, and noted above with respect to 114 in FIG. 9, a user may manually locate the center of each electrode. Image processing device 52 may then store the coordinates of the user located center for each electrode. In situations where no threshold value can be found, the conversion from gray scale to binary may not be necessary.

Figure 11A:
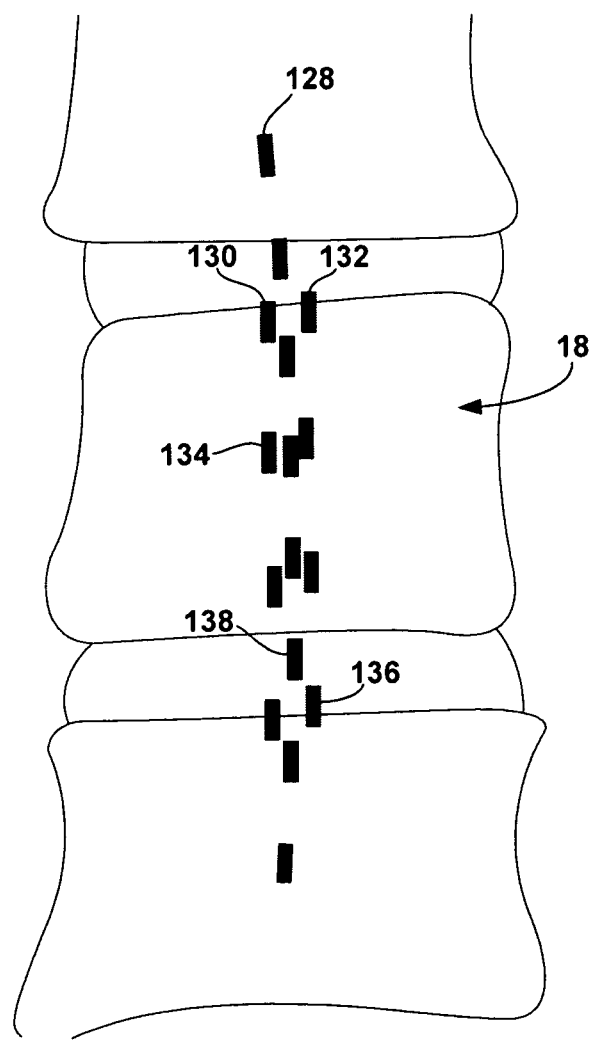
FIGS. 11A, 11B and 11C are diagrams of the leads of FIG. 10 illustrating example image processing operations to identify physical characteristics of the leads.
Figure 11B:
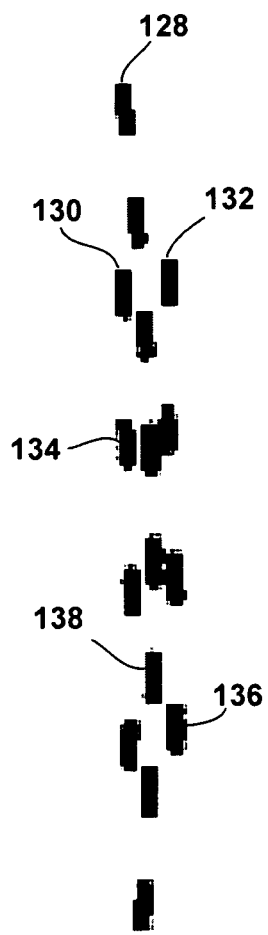
Figure 11C:
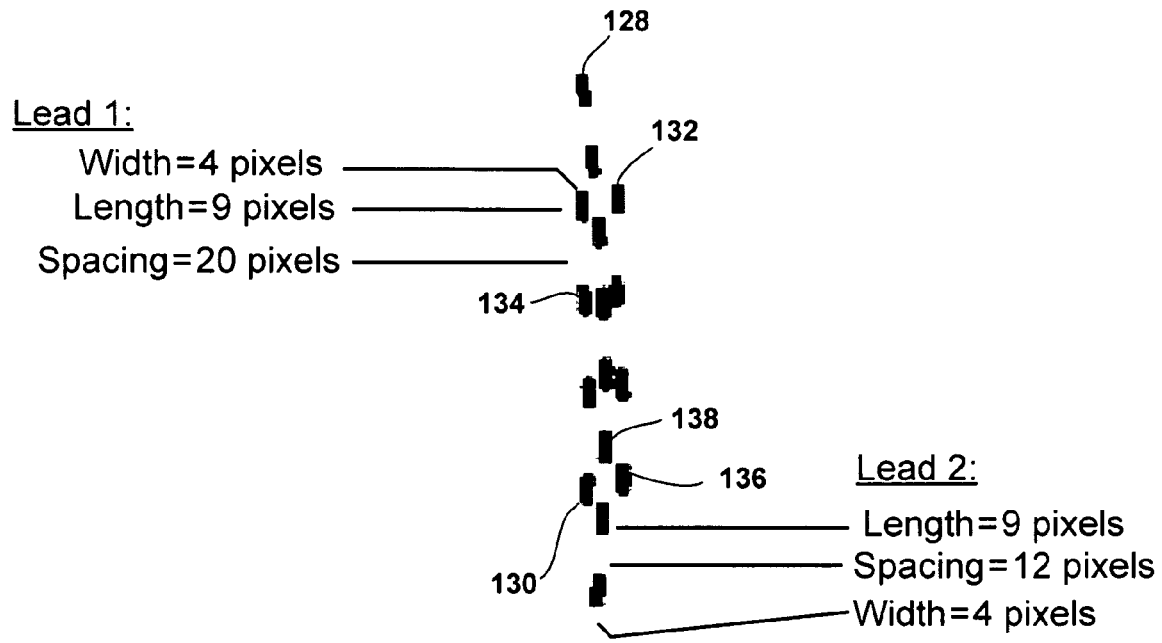

FIGS. 11A, 11B and 11C are examples of image processing operations performed on the image of FIG. 10 by image processing device 52 to identify physical characteristics of the leads. FIG. 11A represents application of a cropping operation to the larger image of FIG. 10 to include only an area of interest, i.e., the area containing the leads 128, 130, and 132 that are relevant to the lead characterization process. As in FIG. 10, lead 128 includes electrode 138, lead 130 includes electrode 134, and lead 132 includes electrode 136. Cropping may be especially desirable if a patient has multiple lead systems, such as old or failed leads implanted near newer functioning leads. In many cases, cropping to an area of interest may be performed automatically using image processing operations. For example, image processing device 52 may automatically crop the image to produce an area of interest based on pattern recognition, optical density recognition, and/or other techniques. As one example, the image may be cropped utilizing ImageJ, a freeware program provided by the National Institute of Health which can be found at http://rsbweb.nih.gov/ij. In some cases, the user may be asked to provide guidance for the cropping operation. For example, the user may be prompted by image processing device 52 to outline a bounding box that contains the area of interest. In addition, the user may also be asked to manually adjust a threshold for threshold filtering until substantially only the electrodes are visible in the resulting image. Such a task of selectively adjusting the threshold may be relatively easy for the user, and may significantly aid the image analysis operations performed by image processing device 52.

In some examples, the gray scale image may be passed through a de-noising filter to reduce or remove inherent noise generated by imaging modality 50. The de-noising filter may, in some example embodiments, be MATLAB's medfilt2, imfilter, and imopen and imclose functions. The medfilt2, imfilter, and imopen and imclose functions may be repeated to form an opening and closing filter. In some examples, not all of the medfilt2, imfilter, and imopen and imclose functions may be necessary to reduce or remove inherent noise generated by imaging modality 50. Medfilt2 function may reduce salt-and-pepper noise. Salt-and-pepper noise may comprise, as one example, random and inadvertent occurring white and black pixels. Medfilt2 may utilize a nonlinear algorithm that preserves edges of the electrodes and reduces or eliminates the salt-and-pepper noise. Imfilter may provide averaging to smooth the image, particularly, the electrode images. As one example, imfilter may provide a filtering mask that traverses the image. The filtering mask may be a rectangle. The filtering mask may provide weighted values which determine how to adjust a pixel of interest. The adjustment to the pixel of interest may be based on surrounding pixels. The imopen and imclose functions executed in succession forms an open-close filter. The imopen and imclose functions provide a traversing rectangle that traverses the image and alters the image based on logic applied to the traversing rectangle as it overlaps the image. For example, a single electrode may appear as two due to noise that appears in the image at two very close electrodes which may be as one example separated by an order of one pixel. The imopen and imclose functions may determine that the two very close electrodes actual comprise one electrode and the separation is due to noise generated by imaging modality 50. By implementing the imopen and imclose functions iteratively the two electrodes may join together as one electrode and the salt-and-pepper noise that caused the separation may be removed.

FIG. 11B represents the result of binarization of the image of FIG. 11A, e.g., using threshold filtering to convert the cropped gray scale image of FIG. 10 into a binary (black/white) image. When the image is converted to black and white, the key objects remaining in the image are the electrodes, as shown in FIG. 11B. After the black/white image of FIG. 11B is generated, image processing device 52 may detect "blobs." A blob is a connected group of 'object' pixels, i.e., pixels designated as a "1." As described above, pixels for electrodes are darker than other pixels and are designated with a value of "1." Therefore, a blob may generally correspond to an electrode of a lead. The number of blobs indicates the number of implanted electrodes. The number of pixels in each blob can be used to determine relative dimensions for lead type identification. For example, the number of pixels in a given direction may be used to determine width, length, spacing, and associated ratios, as discussed above with reference to Table 1.

In general, blobs may be detected and counted using any of a variety of techniques for a pixel array arranged from left-to-right and top-to-bottom. As one example, upon scanning all pixels in the cropped image, pixels associated with a first blob are labeled with the value "1," while pixels associated with other blobs are labeled with blob assignment values of "2," "3", and so forth, depending on the number of blobs in the image. Pixels forming part of blobs can initially be identified by the binary value of "1" assigned to the pixels. However, this binary value is different from the blob assignment value of 1, 2, 3, and so forth, which identifies the particular blob in which a pixel resides. In operation, from the start of a process, the first blob pixel (e.g., having a binary value of 1) is given a blob assignment value of 1, and belongs to blob 1. If the next blob pixel is adjacent to the first blob pixel, or any other pixel in blob 1, then it is also assigned a blob assignment value of 1. If the next blob pixel is not adjacent to a blob 1 pixel, however, it is assigned a blob assignment value of 2, indicating that it belongs to a second blob, blob 2.

The process continues until all blob pixels are assigned to respective blobs, e.g., blob 1, blob 2, blob 3 and so forth. A blob rejection operation may be included to discard spurious blobs. For example, it might be expected that a typical image will yield a reasonable number of large blobs, e.g., 8 or 16 corresponding to 8 or 16 electrodes, and several poorly formed, small blobs, such as single pixels or clusters of pixels. Spurious blobs may be rejected in a number of ways. As an example, a threshold discriminator may be applied to discard blobs that are below a given size, or smaller than an average of the largest blobs, e.g., the largest 8 or 16 blobs. In some embodiments, spurious blobs also could be rejected based on shapes that do not conform to likely electrode shapes.

The number of blobs, and hence the number of electrodes in the implanted lead configuration, can be determined by the highest blob assignment value. If the highest blob assignment value is 16, then there are 16 electrodes in the implanted lead configuration, e.g., as in the case of FIG. 11B. For each blob that is detected, image processing device 52 may define a bounding rectangle. If it is assumed that the electrodes are generally implanted parallel to the image boundaries, image processing device 52 may simply determine the bounding box based on the difference between the maximum and minimum pixel coordinates in each dimension of a blob. As an illustration, if a given blob has a minimum and maximum pixel coordinates in the horizontal direction of 42 and 46, for example, the width of the blob is 4 pixels. Similarly, if the blob has minimum and maximum pixel coordinates in the vertical direction of 125 and 133, then the length of the blob is 8 pixels. In addition, based on the pixel coordinates in the horizontal direction and the pixel coordinates in the vertical direction, image processing device 52 may calculate the center coordinates of the blob. Keeping with the previous example, if the blob has minimum and maximum pixel coordinates in the horizontal direction, i.e., x-axis component of the maximum and minimum pixel coordinates are 42 and 46, the center in the horizontal direction is 44. If the blob has minimum and maximum pixel coordinates in the vertical direction, i.e., y-axis component of the maximum and minimum pixel coordinates are 125 and 133, the center in the vertical direction is 129. Accordingly, the center of the blob is located at coordinate (44, 129).

As another example, the blobs may be detected and counted utilizing a morphological hit-or-miss algorithm. The morphological hit-or-miss algorithm may comprise a structuring element that scans the image in a left-to-right and top-to-bottom fashion, as one example, and determines whether the pixels within the structuring element are binary value 1 or binary value 0. The structuring element may also scan the image in a left-to-right and bottom-to-top fashion, a right-to-left and top-to-bottom fashion, or a right-to-left and bottom-to-top fashion as a few additional examples. The structuring element may be a rectangle with a preprogrammed ratio between the length and the width of the rectangle. Length-to-width ratios for the structuring element may be 3:1, 2:1, and 3:2 as a few examples; however, any ratio is contemplated by this disclosure. A ratio of 3:2 may, in some instances, be the preferred ratio for the structuring element. As shown in FIG. 6 and TABLE 1, the width-to-length ratios for electrodes on leads 72, 74, 76, 78, 80, and 82 are 0.25, 0.5, 0.6, 0.5, 0.5, and 0.5 respectively. Accordingly, the length-to-width ratios for electrodes on leads 72, 74, 76, 78, 80, 82 is 4:1, 2:1, 2:1, 5:3, 2:1, 2:1, and 2:1 respectively. Selecting a length-to-width ratio of 3:2 for the structuring element may, in some instances, be advantageous because the ratio of 3:2 is less than any of the length-to-width ratios for electrodes on leads 72, 74, 76, 78, 80, and 82, thus enabling identification of all electrodes in the image in one iteration of the scan. The length and width of the structuring element may be preprogrammed based on the size of the image generated by imaging modality 50.

In accordance with the morphological hit-or-miss algorithm, the structuring element may identify pixels of the image within the structuring element that are a binary 1 and binary 0. In addition, image processing device 52 may store the coordinates of the each pixel deemed to be a binary 1. As one example, the structuring element may start in the top left corner of the image and determine whether the pixels within the structuring element are binary 1 or binary 0. The structuring element may then traverse to the right and determine whether the pixels are binary 1 or binary 0. The structuring element may keep traversing right until it reaches the rightmost edge of the image. The structuring element then moves down the image and starts at the left end of the image and resumes scanning. The structuring element may then, in this example, complete scanning at the bottom right corner of the image. Notably, each blob may include a plurality of pixels each assigned a binary value of 1. Each blob may be represented as a cluster of pixels where each pixel is assigned a binary value of 1. Each cluster of pixels may be represented as a cluster of pixel coordinates.

Upon completion of the scan by the structuring element, image processing device 52 has stored clusters of pixel coordinates where each pixel coordinate indicates the location of a dark pixel, e.g., coordinate with a binary value of 1. Each cluster of coordinates corresponds to each of the blobs. As described above, each blob may represent an electrode. Similar to before, each blob, e.g., cluster of coordinates, may be assigned a blob assignment value which may also be an assignment value for each electrode.

After finding the cluster of coordinates through the structuring element, image processing device 52 may calculate the location of the center coordinates for each blob, i.e., electrode. In accordance with the morphological hit-or-miss algorithm, image processing device 52 may calculate the center coordinates for each electrode utilizing the maximum and minimum coordinates in the vertical and horizontal directions or a center-of-mass algorithm, as described below.

In one aspect, center coordinates for each electrode may be calculated by averaging the maximum and minimum horizontal direction (i.e., x-axis) values and the maximum and minimum vertical direction (i.e., y-axis) values for each blob. The average of the x-axis and y-axis values provides the center coordinate for each blob. Image processing device 52 may store the center coordinates for each blob, i.e., electrode.

In one aspect, the center coordinates for each electrode may also be calculated by a center-of-mass algorithm. Instead of relying solely on the maximum and minimum x-axis and y-axis coordinates, image processing device 52 averages all the x-axis values for a given blob, and averages all y-axis values for the given blob, in accordance with the center-of mass-algorithm. The center coordinate for the blob is the average x-axis value and average y-axis value. Image processing device 52 may then stores the center coordinates for each blob, i.e., electrode.

If it is assumed that electrodes can be rotated such that the electrodes are not necessarily oriented parallel to the image boundaries, then more complex algorithms may be used to identify bounding rectangles for the blobs. One example of a technique that assumes rotation is described in H. Freeman and R. Shapira, "Determining the Minimal-Area Enclosing Rectangle for an Arbitrary Closed Curve," Comm. ACM, 1975, pages 409-413. Other possible techniques are described, for example, in T. Lindeberg (1998), "Feature detection with automatic scale selection," International Journal of Computer Vision 30 (2), 1998, pages 77-116; D. Lowe, "Distinctive Image Features from Scale-Invariant Keypoints," International Journal of Computer Vision 60 (2), 2004, pages 91-110; and T. Lindeberg, "Detecting Salient Blob-Like Image Structures and Their Scales with a Scale-Space Primal Sketch: A Method for Focus-of-Attention," International Journal of Computer Vision 11(3), 1993, pages 283-318.

After the blobs indicative of individual electrodes are detected, image processing device 52 may determine lead orientation. Lead orientation generally refers to determining which electrodes belong to which implanted leads. An exemplary technique to determine lead orientation is to fit the center points of the bounding rectangles associated with the electrodes to a line or a curve. As an example, the center points of the bounding rectangles associated with the electrodes may be fitted with a line or a curve using regression fit techniques. The center points may be determined by pixel coordinates associated with pixels forming the blobs that define the respective electrodes. A group of electrodes with a regression fit that has a sufficiently low error may be considered to belong together and to a particular lead carrying the electrodes. An exemplary regression technique may be applied to straight lines or to polynomial curves.

As an illustration, a regression fit technique may involve selection of a random group of electrodes, e.g., 4 or 8 electrodes, and performance of a regression fit using the centers of the respective bounding rectangles for the electrodes. If the error is sufficiently low, image processing device 52 groups the selected electrodes together as belonging to the same lead and removes the electrodes from further consideration in the regression fit process. Image processing device 52 then repeats the selection and regression fit analysis until all electrodes have been considered and assigned to leads, and there are no more unassigned electrodes remaining in the image. For each of the resulting leads, image processing device 52 may compare its fit line with other leads. If fit line equations between two leads are sufficiently close, image processing device 52 may group the electrodes from the leads into a single lead. Other pattern or fitting techniques may be used, such as that disclosed in U.S. Pat. No. 3,069,654, to Hough, entitled "Method and Means for Recognizing Complex Patterns."

FIG. 11C is a diagram illustrating extraction of lead and electrode geometries from the image of FIG. 11B. As shown in FIG. 11C, image processing device 52 may obtain measurements, in pixels, of electrode width, length and spacing, as well as the number of electrodes on a lead, as described above. Once electrodes and lead orientations (i.e., grouping of electrodes to leads) are established, the number of pixels in vertical and horizontal dimensions may be used to measure the widths and lengths of the electrodes. The number of pixels may be determined by counting the number of contiguous pixels in respective blobs, using horizontal and vertical scans of the pixel array. For example, a series of eight pixels in a horizontal having the same blob assignment value would indicate a width of eight pixels. As an alternative to scanning, the pixels associated with blobs may be associated with pixel coordinates, e.g., x (horizontal) and y (vertical) values in a pixel coordinate system. In this case, lengths and widths may be determined by the difference between minimum and maximum pixel coordinate values for a blob in the vertical and horizontal dimensions, respectively. Other techniques for determining length and width based on post-implant image analysis may be used.

In the example of FIG. 11C, the width of each electrode, for example, electrode 134 in a left-most lead 130 is 4 pixels, and the length of each electrode, for example, electrode 134 in the left-most lead 130 is 9 pixels. The width of each electrode, for example, electrode 138 in the center lead 128 is 4 pixels and the length of each electrode, for example, electrode 138 in lead 128 is 9 pixels. Hence, the electrode lengths and widths for lead 130 and lead 128 are the same in the example of FIG. 11C. However, intra-lead electrode spacing is different. In particular, given establishment of the electrodes belonging to each lead, image processing device 52 can determine spacing between electrodes on the same lead. In the example of FIG. 11C, the spacing between electrodes on lead 130, with four electrodes, is 20 pixels. The spacing between electrodes on lead 128, with eight electrodes, is 12 pixels. The electrodes on lead 128 are more closely spaced than the electrodes on lead 130.

In some embodiments, in addition to intra-lead electrode spacing on a lead, image processing device 52 may also determine relative positioning of, and spacing between, electrodes on different leads. In this manner, the actual distances between electrodes forming part of an electrode combination for delivery of stimulation can be used to adjust one or more stimulation parameters. In other words, image processing device 52 may permit determination of actual post-implant positioning of electrodes so that stimulation parameters can be modified to compensate for different intra-lead electrode spacing.

Image processing device 52 may match the extracted lead and electrode geometries to those of known leads to determine lead types. For example, by comparing the ratio of electrode width to length and/or intra-lead electrode spacing for each lead to pertinent ratios and/or spacing of known leads, image processing device 52 can determine the type of each lead. A variety of leads that differ in number of electrodes, electrode length, electrode width and electrode spacing may be implanted within a patient, either percutaneously or surgically. This description generally refers to percutaneously implanted leads for purposes of illustration. However, similar results can be obtained for surgically implanted leads.

Even though actual dimensions are not yet known, pixel ratios can be used to match the implanted leads to known leads. With reference to the leads depicted in FIG. 6 and characterized in Table 1, for example, characterization unit 62 (FIG. 5B) may identify a type of lead based on a number of electrodes, a ratio of electrode length to intra-lead electrode spacing, a ratio of electrode width to electrode length, or a combination of such characteristics. Assuming for purposes of illustration that lead possibilities are limited to those shown in FIG. 6, if a lead has four electrodes, it can be determined that it must be one of leads 72, 74, or 76.

Because the ratio of electrode length to intra-lead electrode spacing is the same for each of leads 72, 74, 76, i.e., 0.5, the ratio of electrode width to length is used to determine which lead matches the implanted lead. If the lead has an electrode width to length ratio of approximately 0.5, with reference to lead characterization data such as that shown in Table 1, characterization unit 62 determines that the particular lead corresponds to lead 74 of FIG. 6. Characterization unit 62 of image processing device 52 may repeat this process for each of the leads identified in the image.

As another example, if the lead has eight electrodes, the ratio of electrode width to length is the same, i.e., 0.5, for the leads of FIG. 6 and Table 1. In this case, characterization unit 62 (FIG. 5B) may refer to the ratio between electrode length to intra-lead electrode spacing to determine which lead corresponds to the 8-electrode lead from the image. If the ratio is approximately 0.75, then the pertinent lead is lead 80 from FIG. 6, given the characterization data in Table 1. Notably, identification of the lead type as described above may be performed using numbers of pixels (or voxels or other volumetric units) instead of units of actual measurement.

As shown in FIG. 11C, for example, the number of pixels forming the electrode width, electrode length, and intra-lead electrode spacing can be used to generate the ratios for comparison to the ratios associated with in the known lead types. In this example, the best fit for the left-most lead 130 in the image of FIG. 11C is lead 74 (Pisces Quad lead) and the best fit for the center lead 128 in the image of FIG. 11C is lead 80 (1×8 Subcompact lead).

TABLE 2

|  | Lead Number | | | | | | | |
|---|---|---|---|---|---|---|---|---|
|  | 72 | 74 | 76 | 78 | 80 | 82 | 130 | 128 |
| Number of Electrodes | 4 | 4 | 4 | 8 | 8 | 8 | 4 | 8 |
| Ratio of Electrode Width to Electrode Length | 1.5/6 = 0.25 | 1.5/3 = 0.5 | 1.5/2.5 = 0.6 | 1.5/3 = 0.5 | 1.5/3 = 0.5 | 1.5/3 = 0.5 | 4/9 = .44 | 4/9 = .44 |
| Ratio of Electrode Length to Electrode Spacing | 6/12 = 0.5 | 3/6 = 0.5 | 2.5/5 = 0.5 | 3/1.5 = 2 | 3/4 = 0.75 | 3/6 = 0.5 | 9/20 = .45 | 9/12 = .75 |

Table 2 above shows the correlation between the left-most lead 130 in FIG. 11C and the center lead 128 in FIG. 11C with the known leads of Table 1. As shown in Table 2, the ratio of pixels forming the width and length of the electrodes for each lead is 4/9, which is equal to 0.44 and approximately equal to 0.5. The ratio in pixels of electrode length to intra-lead electrode spacing is 9/20 (equal to 0.45) for the left-most lead 130 and 9/12 (equal to 0.75 for the center lead 128. The lead type for the left-most lead 130 can be determined based on the ratio of electrode width to length, where 0.44 corresponds most closely to the ratio of 0.5 for lead 74. The lead type for the center lead 128 can be determined based on the ratio of electrode length to intra-lead electrode spacing, where 0.75 corresponds to the ratio of 0.75 for lead 80. The same analysis can be performed for right-most lead 132 in the image of FIG. 11C. Higher resolution images may yield closer matches to the ideal ratios.

Hence, as described above, the ratios used to identify lead type may be calculated by first determining the number of pixels necessary to image the width, referred to as "pixel width" herein, and length, referred to as "pixel length" herein, of an electrode. The number of pixels between electrodes on a lead, referred to as "pixel spacing" herein, may also be determined. For example, as shown in FIG. 11C the width of electrode 134 on lead 130 is four pixels. The length of electrode 134 on lead 130 is nine pixels. The spacing between electrodes on lead 130 is twenty pixels. The width of electrode 138 on lead 128 is four pixels. The length of electrode 138 on lead 128 is nine pixels. The spacing between electrodes on lead 128 is twelve pixels.

Once the pixel width, pixel length, and pixel spacing are determined, ratios of pixel width to pixel length, pixel width to pixel spacing, and pixel length to pixel spacing may be calculated. The various ratios may be referred to herein as extracted geometries. The extracted geometries may be compared to geometries of known lead types, as described above, to determine the lead type of the implanted lead. More or fewer ratios may be needed based on the number of lead types and the similarities and differences among the characteristics of the lead types. Accordingly, the ratios shown in Tables 1 and Table 2 are for purposes of example and should not be considered limiting.

Automated extraction of geometries and determination of lead types can reduce the time and effort of users in gathering such information, and promote a more accurate and less error prone result. For example, the actual, post-implant lead configuration may be presented more accurately via programmer 20, reducing the likelihood of programming errors and/or patient risks associated with mismatches between lead configurations and parameter settings. In this manner, programming tools can be more representative of reality. For example, a programming user interface provided by programmer 20 can aid the user in more effectively visualizing actual electrode locations, e.g., for the purpose of using specific configurations such as transverse tripole or the like. In addition, automated, guided programming algorithms executed by programmer 20 can be smarter. As an example, an algorithm that shifts a stimulation zone made up of electrodes on multiple leads longitudinally across the array may also adjust current or voltage amplitude up and down as guarding electrodes shift relative to stimulation electrodes.

Once characterization unit 62 (FIG. 5B) has positively identified the lead types in the post-implant image, it is possible to make a correlation between measured pixels and actual measurement units, such as millimeters. With actual measurement units, actual positioning of electrodes and/or leads may be determined. Using a 1×8 compact lead (corresponding to lead 80 of FIG. 6 and Table 1 and center lead 128 of FIG. 11C), for example, characterization unit 62 can determine that the 12 pixel spacing between electrodes corresponds to 4 mm. The 4 mm spacing is known from the lead characteristics of the known 1×8 compact lead 80. Hence, characterization unit 62 can determine that 1 mm equals 3 pixels.

Upon determination of the lead type, e.g., by comparing extracted geometries to geometries of a known lead type, the dimensional scale of a pixel in the image can be determined. The dimensional scale of the pixel aids in calculating relative, actual positions of various electrodes and/or leads. The dimensional scale of a pixel may be calculated by equating either the pixel length, pixel width, or pixel spacing of electrodes on a lead to the known length, width, or spacing of electrodes on the known lead type. For example, as shown in FIG. 11C, the pixel length for electrode 134 of lead 128 is nine pixels. As calculated above, lead 130 is the Pisces Quad lead. The electrode length for the Pisces Quad lead is 3 mm. Therefore, nine pixels is equal to 3 mm. This translates into the dimension of each pixel being ⅓ mm (3/9). The actual relative positioning of the leads and/or electrodes may be calculated based on the pixels corresponding to the electrodes and the dimension of each pixel. A clinician, patient, image processing device 52, or external programmer 20 may determine the number of pixels between the two leads.

In some examples, the actual determination of the lead type may not be necessary. As described above, the pixel width, pixel length, and/or pixel spacing may be calculated. The pixel width, pixel length, and/or pixel spacing may provide the clinician with guidance for modifying the therapy program. In some examples, the clinician may estimate the lead type based on the pixel width, pixel length, and/or pixel spacing. In such examples, the image processing device may not need to compare the extracted geometries to the geometries of known lead types. Instead, the clinician may approximate the lead type based only on dimensions in terms of pixels.

Furthermore, as described above, in some examples, image processing device 52 may determine the locations of electrodes on the lead and the relative location of the leads with respect to anatomical structures. The clinician or patient may modify the therapy program to select a different electrode on the identified lead based solely on the pixel spacing and the locations of the electrodes, as one example. Accordingly, though the lead type may not be known, the clinician or patient may modify the therapy program to provide more effective therapy relying on the pixel width, pixel length, and/or pixel spacing for identified electrodes. The generation of effective therapy may, in some cases, require trial and error by the clinician or patient.

Figure 12A:
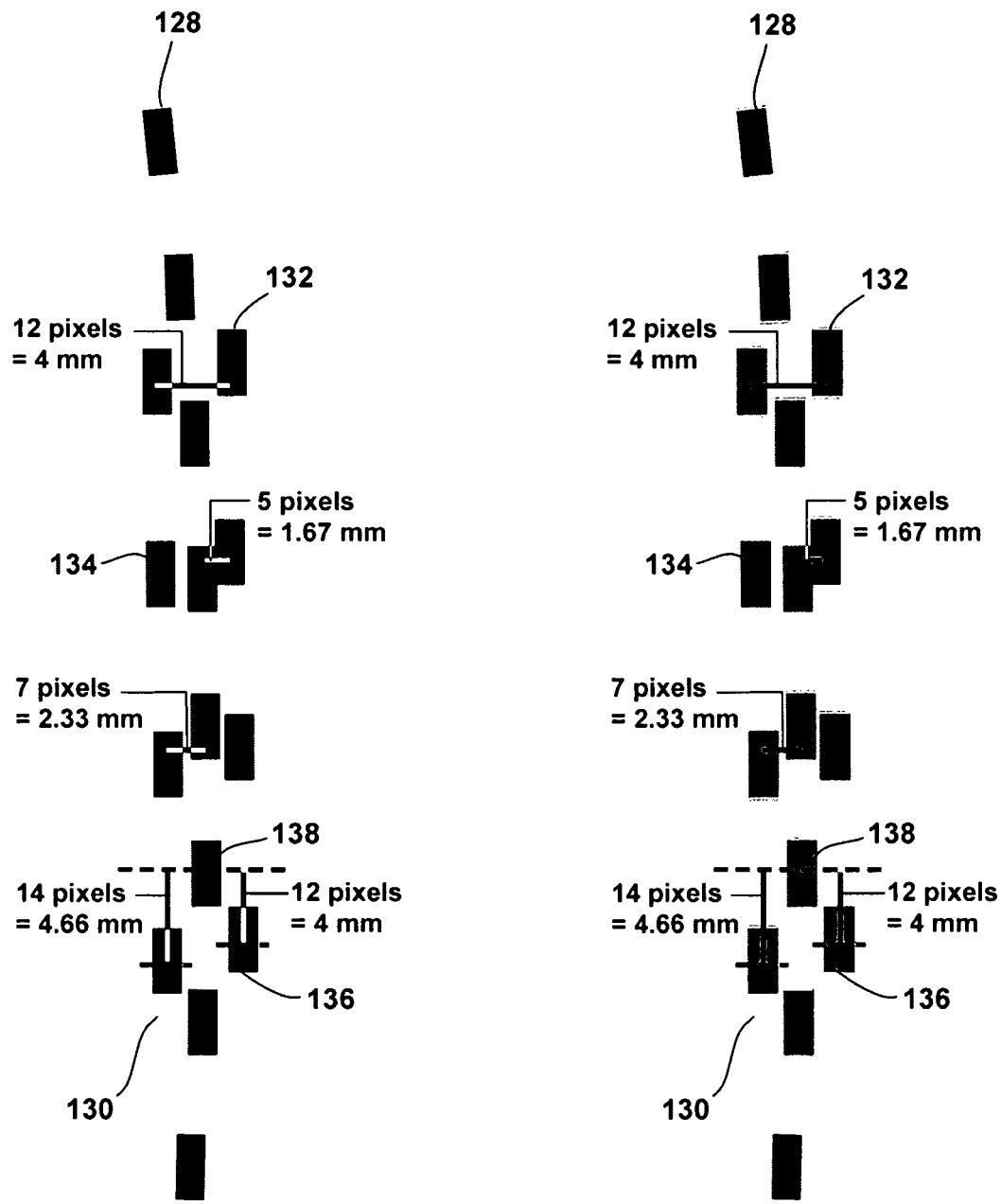
FIGS. 12A and 12B are example images of a lead configuration illustrating use of pixel dimensional scale to determine relative positioning of electrodes.
Figure 12B:
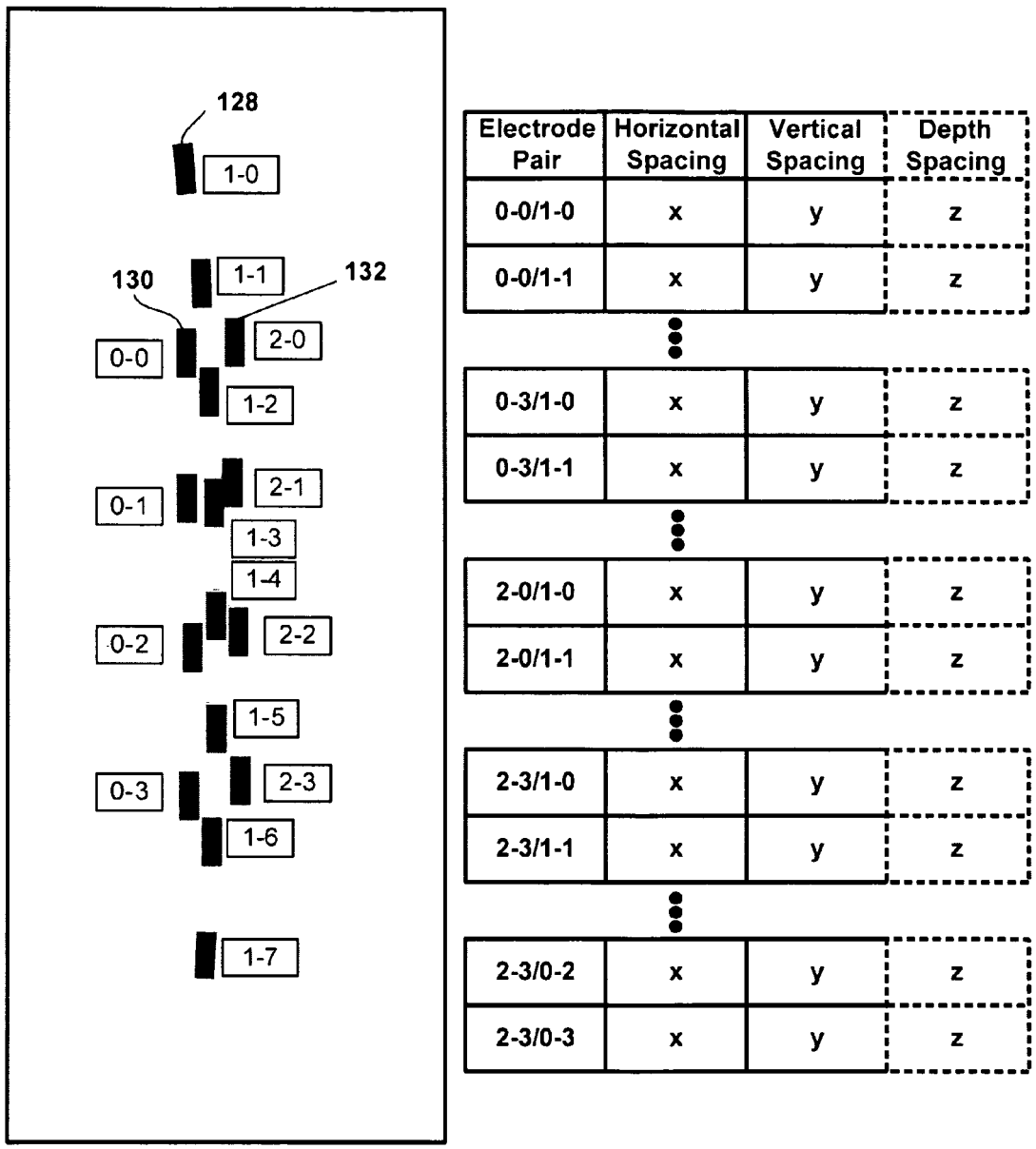

FIGS. 12A and 12B are example images of a lead configuration illustrating use of pixel scale to determine relative positioning of electrodes. The relative positions of leads and/or the electrodes on the leads may be calculated, for example, by multiplying the number of pixels between the leads and the dimension of each pixel. For example, as shown in FIG. 12A, image analysis unit 60 (FIG. 5B) may determine that leads 130 and 128 are separated by 7 pixels. By multiplying 7 by ⅓ mm, characterization unit 62 may determine that the relative lateral spacing between left-most lead 130 and center lead 128 is 2.33 mm.

Similarly, image analysis unit 60 may determine that the spacing between left-most lead 130 and right-most lead 132 is 12 pixels. In this case, characterization unit 62 may determine that the spacing between leads 130 and 132 is 12 pixels multiplied by ⅓ mm per pixel, which is 4 mm. The number of pixels may be counted from the center of an electrode on one lead to the center of another electrode on another lead. The center may be determined as the center pixel of a blob or bounding rectangle defining an electrode. As another example, as shown in FIG. 12A, the spacing between an electrode on center lead 128 and an electrode on right-most lead 132 is 5 pixels, which is equivalent to 5 pixels times ⅓ mm per pixel, i.e., 1.67 mm.

With reference to the example of FIG. 12A, as described above, actual distances between adjacent leads can be determined by determining the number of pixels between adjacent electrodes and multiplying the number of pixels by the scale of each pixel. The leads may be assumed to be generally parallel to each other such that the lateral distance between pixels on different leads can be assumed to represent the spacing between the leads along their entire lengths. In addition, it may be assumed that the adjacent leads reside in substantially the same plane. In some embodiments, however, it may be desirable to determine actual spacing between individual electrodes along the lengths of the leads, taking into account curvature of the leads relative to one another.

It may also be desirable, in some embodiments, to determine not only lateral, i.e., horizontal spacing, but also vertical spacing. In the example of FIG. 12A, although the left-most lead 130 and right-most lead 132 are identical in terms of lead type, the electrodes carried by the leads are positioned at different heights relative to one another and relative to the center lead 128. Therefore, relative vertical spacing of electrodes carried by the leads may be a useful characteristic. In FIG. 12A, from vertical center to vertical center of the electrodes, an electrode on the left-most lead 130 is positioned vertically 14 pixels below an electrode on the center lead 128. A corresponding electrode on the right-most lead 132, however, is positioned vertically 12 pixels below the electrode on the center lead 128. The difference in vertical spacing demonstrates that the right-most lead is positioned slightly higher relative to the left-most lead.

Further, in some embodiments, it may be desirable to determine spacing between electrodes in a third dimension, such as depth, taking into account implantation of the leads in different planes relative to one another. In this case, image processing device 52 may process two or more images of the implanted lead configuration, taken from different perspectives, such as a front view and a side view. In this way, image processing device 52 may detect relative vertical and horizontal spacing of the leads in a first two-dimensional plane, as well as relative spacing of the leads in a plane perpendicular to the first plane, thereby providing differences in depth.

As an illustration, image processing device 52 may generate a comprehensive set of spacing measurements for different pairs of electrodes carried by the multiple leads. The spacing measurements may include horizontal spacing, vertical spacing, and/or depth spacing. FIG. 12B shows an example post-implant image corresponding to 12A, and further including electrode identification values to identify the respective electrodes on the three implanted leads. In the example of FIG. 12B, electrodes on left-most lead 130 are given values 0-0, 0-1, 0-2 and 0-3, from top to bottom, wherein the first number indicates the lead and the second number indicates the electrode on that lead. The eight electrodes on center lead 128 are identified with values 1-0, 1-1, 1-2, 1-3, 1-4, 1-5, 1-6, and 1-7. The four electrodes on the right-most lead 132 are identified with values 2-0, 2-1, 2-2, and 2-3. This numbering system is presented for purposes of illustration, and should not be considered limiting in any way.

With reference to the example electrode identification values for the electrodes on leads 128, 130 and 132 in FIG. 12B, characterization unit 62 may generate a comprehensive set of spacing measurements to represent relative positioning and distances between respective electrodes. The spacing measurements may be determined by scanning the space between the centers of respective electrodes in horizontal, vertical and/or depth dimensions and counting pixels. Alternatively, the spacing measurements may be determined by calculating the differences between pixel coordinate values associated with the centers of the electrodes. The centers of the electrodes may be defined by pixel coordinate values in the horizontal, vertical and/or depth dimensions. As a further alternative, spacing measurements may be determined by scanning or determining the space between adjacent edges of respective electrodes in horizontal, vertical and/or depth dimensions.

Whether based on pixel counts or difference calculations, characterization unit 62 may generate a table of spacing measurements for some or all of the possible pairs of electrodes. As shown in FIG. 12B, the table may include horizontal spacing, vertical spacing, and/or depth spacing coordinates for each pair of electrodes. For example, the electrode pair comprising the top-most electrode on the left-most lead 130 and the top-most electrode on the center lead 128 may be represented as electrode pair 0-0/1-0. As another example, the electrode pair comprising the bottom electrode on left-most lead 130 and the third electrode on right-most lead 132 may be represented as electrode pair 0-3/2-2. Horizontal, vertical and/or depth spacing values may be recorded for the electrode pair, e.g., in a lookup table in memory, and provided to programmer 20 as part of the lead characterization data, e.g., for use in presenting electrode arrays and supporting programming of parameters for electrode combinations within the electrode arrays. Again, spacing measurements in the depth dimension may require analysis of at least one additional image from a different perspective, and therefore may be optional in various embodiments.

As an alternative, instead of predetermining some or all of the spacing measurements, characterization unit 62 may record pixel coordinate values of electrode centers, e.g., in the horizontal, vertical and/or depth dimensions. The pixel coordinate values for the centers of the electrodes can then be used later, as needed, to calculate distances between selected pairs of electrodes, e.g., in programmer 20. In some embodiments, storing pixel coordinate values for later calculation may be more memory efficient and less computationally intensive than pre-calculating spacing values for some or all possible electrode pairs. Instead, when a particular electrode combination is selected by a user, programmer 20 may use the pixel coordinate values associated with the centers of the electrodes in the combination to calculate spacing in the desired dimensions, e.g., the horizontal, vertical, and/or depth dimensions.

Determination of relative spacing between different electrodes in a lead configuration may serve multiple purposes. One purpose may be to support graphic representation of the leads via a display. For example, the spacing measurements may be used to more accurately present a graphical depiction of the lead configuration on a display associated with programmer 20. Programmer 20 may graphically represent simply the types of leads and electrodes in a substantially parallel orientation with a default spacing. Alternatively, programmer 20 may graphically represent the types of leads and electrodes with a constant horizontal spacing determined based on a single measurement or an average of several measurements, e.g., as provided by image processing device 52 as part of the lead characterization data. In this case, programmer 20 may show approximate lead-to-lead spacing but would not reveal differences in spacing along the lengths of the leads due to lead curvature upon implantation.

In another example, programmer 20 may show both approximate vertical and horizontal spacing, or vertical, horizontal and depth spacing in a similar manner. Again, differences in spacing along the lengths of the leads would not be revealed. Therefore, as an alternative, programmer 20 may graphically represent types of leads and electrodes with horizontal, vertical, and/or depth spacing that vary according to the approximate actual spacing between respective pairs of electrodes. In this manner, programmer 20 may more effectively present differences in electrode-to-electrode spacing due to curvature of the leads.

Use of a constant spacing could rely on a single measurement or an average of multiple measurements, e.g., as provided by image processing device 52 as part of the lead characterization data. Use of actual, variable spacing could rely on precalculated spacing values in combination with width, length, and intra-lead electrode spacing values of the electrodes associated with the identified lead types. Alternatively, actual, variable spacing could rely on pixel coordinate values associated with respective electrodes, e.g., in combination with width, length and intra-lead electrode spacing values of the electrodes associated with the identified lead types.

Another purpose of relative spacing between electrodes in the lead configuration, in addition or as an alternative to accurate graphical presentation of a lead configuration, may be to support more manual or automated programming of stimulation parameters associated with the electrodes forming electrode combinations selected by the user or by an automated programming algorithm. For example, if a particular electrode combination includes a cathode and an anode on different leads, the distance between the cathode and anode may influence the values of a parameters, such as current or voltage amplitude, that should be used to deliver electrical stimulation energy via the electrode combination. As an illustration, programmer 20 may adjust amplitude upward based on increased spacing between electrodes, or downward (decrease amplitude) based on decreased spacing between electrode, adjust amplitude upward or downward if spacing between electrodes and an anatomical target increases or decreases, respectively, or adjust amplitude upward or downward if electrode surface areas or lead characteristics change upon implantation of replacement leads or supplemental leads.

If relative spacing information indicates that the electrodes are closer than a reference value, for example, it may be possible to deliver stimulation from stimulator 14 with a reduced amplitude. In particular, reduced current or voltage levels may still be effective over the reduced distance through the tissue of the patient. At the same time, reduced levels may be effective in conserving power, such as battery resources. If relative spacing information indicates the electrodes are further away than a reference value, it may be advisable to deliver stimulation via stimulator 14 with increased current or voltage amplitude to ensure efficacy of the stimulation given the increased distance through the tissue of the patient.

In some embodiments, programmer 20 may propose or automatically select parameter adjustments, such as increases or decreases in current or voltage amplitude, for a given electrode combination based on relative spacing between two or more electrodes forming the electrode combination. For example, an automated programming algorithm executed by programmer 20 may propose an amplitude increase or decrease to the user as a function of the distance between electrodes in an electrode combination.

The increase or decrease may be computed as a mathematical function of the distance between the electrodes or by reference to pre-computed entries in a lookup table that are correlated with particular distances or distance ranges. In either case, the values may be calculated as a function of horizontal, vertical and/or depth distances, or vector values that represent combinations of two or more of such distances. In this manner, automated analysis of one or more post-implant images of the implanted lead configuration can provide electrode positioning feedback for adjustment of stimulation parameters to support continued therapeutic efficacy. Relative positioning information also may be useful as an input to finite element modeling process used to predict an area of recruitment and visualize stimulation.

As a further alternative, programmer 20 may compute amplitude increases or decreases based on incrementing or decrementing the amplitude according to the difference between the actual distance and a reference or default distance. If the actual distance is less than the default distance, for example, the amplitude may be decremented by a fixed amount determined as a function of the difference. Similarly, if the actual distance is greater than the default distance, the amplitude may be increased by a fixed amount determined as a function of the difference. Again, programmer 20 may adjust amplitude upward based on increased spacing between electrodes, or downward (decrease amplitude) based on decreased spacing between electrode, adjust amplitude upward or downward if spacing between electrodes and an anatomical target increases or decreases, respectively, or adjust amplitude upward or downward if electrode surface areas or lead characteristics change upon implantation of replacement leads or supplemental leads.

Programmer 20 also may use relative spacing between electrodes to automatically adjust or propose adjustments for any of a variety of parameters such as amplitude, pulse width, pulse rate, duty cycle, or the like. In addition, in some embodiments, if the actual distance between electrodes in an electrode combination are too close or too far away from one another, e.g., as determined by reference to minimum and maximum distance bounds, programmer 20 may present a message to the user suggesting that the user select a different electrode combination because the intra-lead electrode spacing distance is out of range. Alternatively, programmer 20 may be configured to automatically select or present a proposed selection of a different electrode combination. In some cases, adjustment of parameters and/or selection of different electrode combinations may be fully automatic. In other cases, however, programmer 20 may present such adjustments and/or selections to a user as proposals for review and approval by the user before actual application.

As an additional or alternative purpose, relative spacing between electrodes in the lead configuration may be used to detect lead migration over time. For example, lead characteristics such as relative spacing of electrodes may be obtained from different images taken at different times, and then compared to determine whether one or more of the electrodes has shifted relative to a previous position. Migration may be detected by comparing the positions to anatomical landmarks either by automated image processing, manual inspection, or both.

Alternatively, or additionally, migration may be detected by ensuring a common frame of reference and common scale for each image and comparing pixel coordinate values of the electrodes in the different images to determine whether any migration has occurred. Migration may be in the horizontal, vertical and/or depth dimension. Using migration information, such as relative spacing differences, programmer 20 may automatically adjust or propose adjustments to one or more stimulation parameters, e.g., in a manner similar to that described above.

Figure 13:
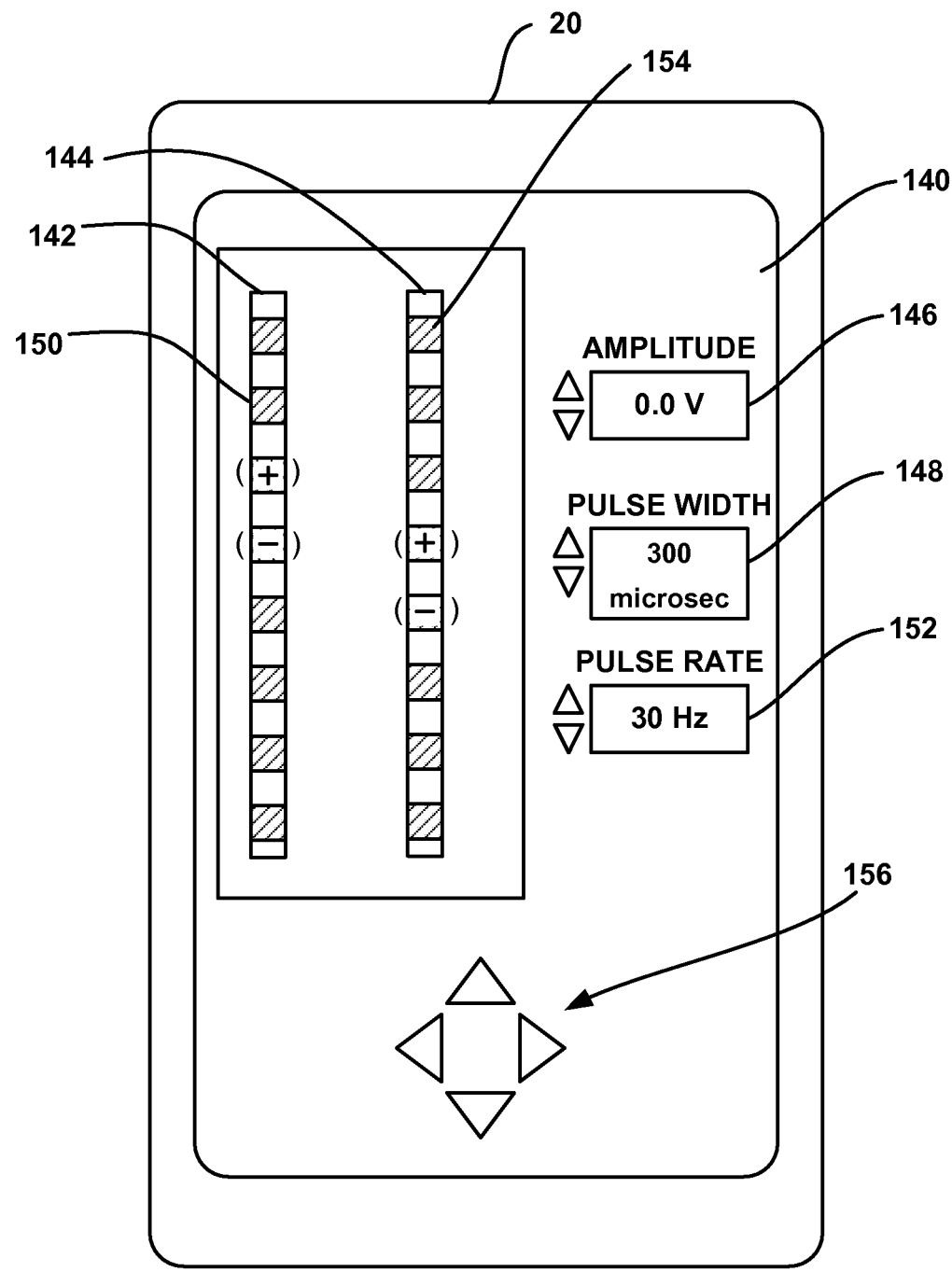
FIG. 13 is conceptual diagram of a user interface associated with an electrical stimulation device programmer.

FIG. 13 is conceptual diagram of a user interface associated with an electrical stimulation device programmer 20. Programmer 20 may automatically present an indication of the characterization of an electrode array on a display 140 associated with a programmer, e.g., based on the lead characterization data provided by image processing device 52. In this manner, display 140 may function as an output unit that automatically generates an indication of the characterization of the electrode array formed by the lead configuration.

Programmer 20 also may be used to set and modify therapy program parameters based at least in part on relative positions of leads and/or electrodes determined based on analysis of a post-implant image. In the example of FIG. 13, programmer 20 includes display 140. Display 140 includes a display of leads 142 and 144, carrying electrodes 150, 154, amplitude selector 146, pulse width selector 148, pulse rate selector 152, and electrode selector 156.

In FIG. 13, for ease of illustration, reference numerals 150, 154 point to only two of the several electrodes on leads 142, 144. Electrode selector 156 may be used to select different electrode combinations along the lengths of leads 142 and 144, e.g., by moving an existing electrode combination upward or downward, or laterally, using the up/down and left/right arrows associated with the selection unit. Amplitude selector 146, pulse width selector 148, and pulse rate selector 152 may include up/down arrows to permit a user to manually increase or decrease respective parameter values.

Display 140 may be a touchscreen display that permits a user to interact with selectors 146, 148, 152, 156 via a stylus or other pointing device. In addition, in some embodiments, the touchscreen may permit user to select individual electrodes on leads 142, 144, and specify polarities, to permit the user to define electrode combinations. Hence, a user such as a physician, clinician or patient, may modify the amplitude, pulse width, and pulse rate of the electrical stimulation energy by amplitude selector 146, pulse width selector 148, and pulse rate selector 152, respectively. Using electrode selector 156 and/or a stylus to select individual electrodes. In this manner, the user may modify which electrodes are used in an electrode combination to deliver stimulation.

In the example of FIG. 13, programmer 20 may use lead characterization data obtained from image processing device 52 to selectively display leads 142, 144. In particular, programmer 20 may use the lead characterization data to determine the lead types, such as 1×8, 1×4, and the like, the number of leads, and lead orientations in the lead configuration, and then drive display 140 to present a representation of the lead configuration. In this manner, the displayed lead configuration is accurate with respect to lead type and number of leads, and can be displayed automatically with little or no user time or effort. In addition, the lead characterization data can be used by programmer 20 to automatically select programming options that are appropriate for the lead configuration, or negate programming options that are not appropriate for the lead configuration. As an added feature, in some embodiments, programmer 20 may automatically present on display 140 each lead type, e.g., 1×8, 1×4, or the like, as well as the lead model number, e.g., Medtronic Pisces Quad Lead Model 3487.

If the lead characterization data indicates two 1×8 leads, for example, programmer 20 may be configured to present only programming options that are appropriate such a lead configuration. For example, programmer 20 may not present programming options, such as shifts of the stimulation zone, that would only be appropriate for a combination of three 1×8 leads, a combination of one 1×8 and two 1×4 leads, or a combination of a 1×8 lead and a 1×4 lead. Likewise, programmer 20 may not present programming options that would support a lateral shift of an electrode combination if the lead configuration only provides two leads. In this case, in general, a lateral shift would be appropriate for a lead configuration with three or more adjacent leads, but not a lead configuration with only two leads. Using the lead characterization data, programmer 20 can accurately present the implanted lead configuration and avoid programming options or features that would present a mismatch with the implanted lead configuration, thereby promoting accuracy, efficacy and/or safety.

In the example of FIG. 13, constant horizontal spacing between the electrodes on leads 142 and 144 is represented, e.g., based on a single relative spacing measurement or an average of multiple measurements. In this manner, leads 142, 144 can be depicted as straight and parallel rather than curved, if applicable, yet still provide meaningful spacing information, e.g., as provided by image processing device 52 as part of the lead characterization data. In addition, in the example of FIG. 13, programmer 20 presents only horizontal spacing and assumes, for purposes of the graphical depiction on display 140, that the leads and associated electrodes are positioned at the same relative heights.

Even if programmer 20 shows leads 142, 144 as straight and vertically aligned, in some embodiments, the programmer may use multiple actual spacing measurements, e.g., from a lookup table or calculated as needed based on pixel coordinates, to aid in programming. For example, programmer 20 may present a simplified version of the lead configuration on display 140, but use more complex measurements to adjust or propose adjustments to one or more parameters such as amplitude.

Programmer 20 may receive user input specifying selection, as an electrode combination, of a plurality of the electrodes displayed in the representation of the electrical stimulation leads 142, 144, and receive user input specifying one or more electrical stimulation parameters associated with electrical stimulation to be delivered by the implantable electrical stimulation device 12 via the selected electrodes. Based on lead types and actual relative positioning, programmer 20 may automatically adjust or propose adjustments to one or more parameters or electrode combinations, e.g., to maintain a desired therapeutic effect and/or conserve power resources.

Figure 14:
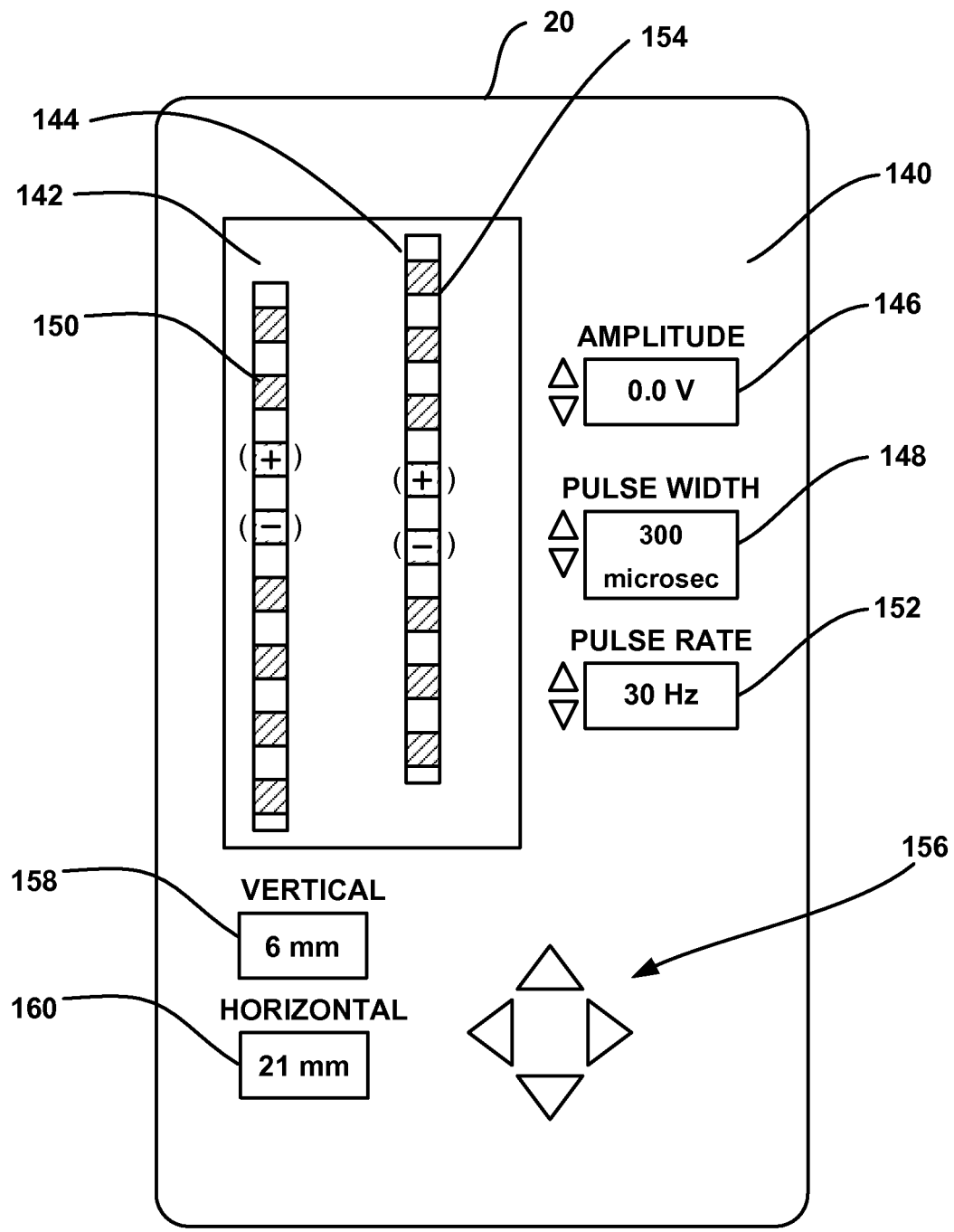
FIG. 14 is a conceptual diagram of the user interface of FIG. 13 showing relative actual vertical and horizontal positioning of electrodes as a function of post-implant image analysis.

FIG. 14 is a conceptual diagram of the user interface of FIG. 13 showing relative actual vertical positioning of electrodes as a function of post-implant image analysis. The graphic depiction of leads 142, 144 in FIG. 14 conforms substantially to that of FIG. 13 in that it relies on constant horizontal relative spacing between the leads 142, 144 and depicts straight, parallel leads. However, in addition to horizontal relative spacing, display 140 presents vertical relative spacing, which may be determined, e.g., based on a single vertical spacing measurement or an average of multiple vertical spacing measurements. In this manner, programmer 20 graphically presents a simplified view of the implanted lead configuration, but conveys useful horizontal and vertical spacing information, e.g., as provided by image processing device 52 as part of the lead characterization data. In some embodiments, leads 142, 144 may be displayed against a graph-like background that provides an indication of distance. Additionally, or alternatively, display 140 may present vertical and horizontal spacing values, e.g., as indicated by reference numerals 158 and 160 in FIG. 14.

Figure 15:
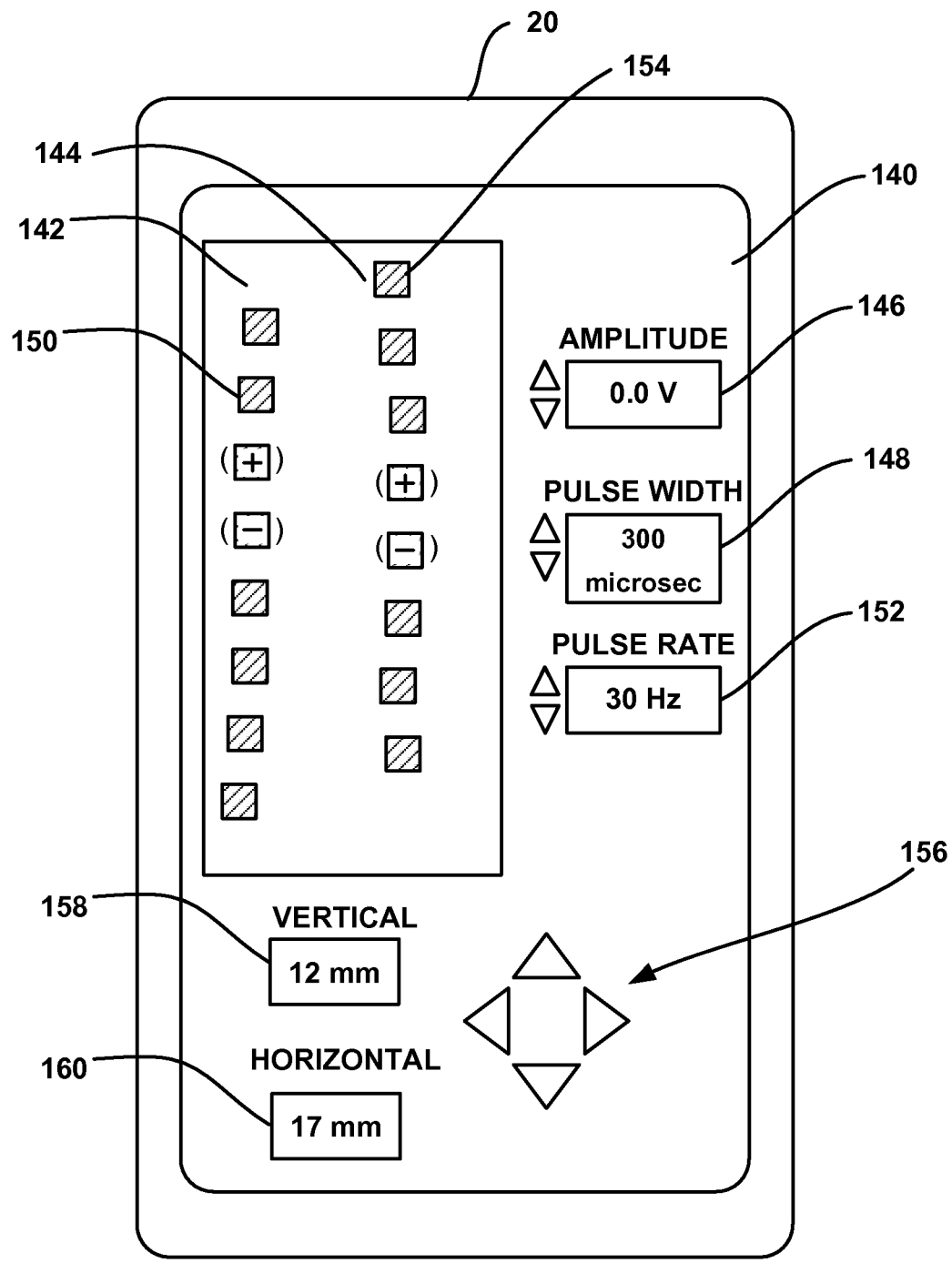
FIG. 15 is a conceptual diagram of another user interface of FIG. 13 showing relative actual vertical and horizontal positioning of electrodes as a function of post-implant image analysis.

FIG. 15 is a conceptual diagram of the user interface of FIG. 13 showing relative actual horizontal and vertical positioning of electrodes as a function of post-implant image analysis. In particular, programmer 20 may display a representation of the electrical stimulation leads 142, 144 in the image on display 140. The representation may indicate the actual relative positions of the electrodes. In the example of FIG. 15, programmer 20 shows actual relative spacing between individual electrodes 150, 154 within leads 142, 144 associated implanted lead configuration. The actual relative spacing may be precalculated based on pixel counts or pixel coordinate values, or by other methods. Such information may be included in the lead characterization data from image processing device 52 or computed by programmer 20 based on information provided in the lead characterization data.

As shown in FIG. 15, programmer 20 may graphically present each electrode 150, 154 on display 140 at a position indicated by the lead characterization data. The depiction of the electrode may be based on the lead type and associated electrode width, length and intra-lead electrode spacing data, as well as the actual electrode position data indicated by pixel coordinates or other data. In this way, programmer 20 presents a view of the electrodes that conveys actual positioning that may result from horizontal or vertical displacement of leads 142, 144 as well as lead curvature. Programmer 20 thereby presents a more complex representation of leads 142, 144 and electrodes 150, 154 that may be capable of conveying more detailed information such as lead curvature and actual, relative positioning of electrodes, and spacing between selected electrodes.

In some embodiments, programmer 20 may be configured to present actual spacing information for selected electrodes on display 140 in terms of the distance (e.g., in mm) between such electrodes. For example, a user may click on two different electrodes to view spacing information for those electrodes. As an illustration, a user could click on an electrode, e.g., via a touchscreen with a stylus, once to select the electrode for a distance indication, twice to select the electrode as a cathode (indicated by a plus sign) and three times to select the electrode as an anode (indicated by a minus sign). Upon clicking another electrode in the same manner to select the electrode for a distance indication, programmer 20 may present vertical and horizontal spacing values between the electrodes in the selected pair, e.g., as indicated by reference numerals 158, 160 in FIG. 15.

In some embodiments, depth information also may be accessible and/or displayed with the vertical and horizontal spacing values, particularly when 3D image information is available. A full 3D visualization of the electrodes may be provided in some embodiments. Depth can be indicated by color, transparency, or relative size of electrodes on a display screen. For example, smaller electrodes may be perceived as further away and therefore "deeper" within the implant region. Programmer 20 may be configured to permit a user to click on an electrode and an anatomical target to obtain distances between the electrode and the target, either as an alternative or in addition to inter-electrode spacing.

Figure 16:
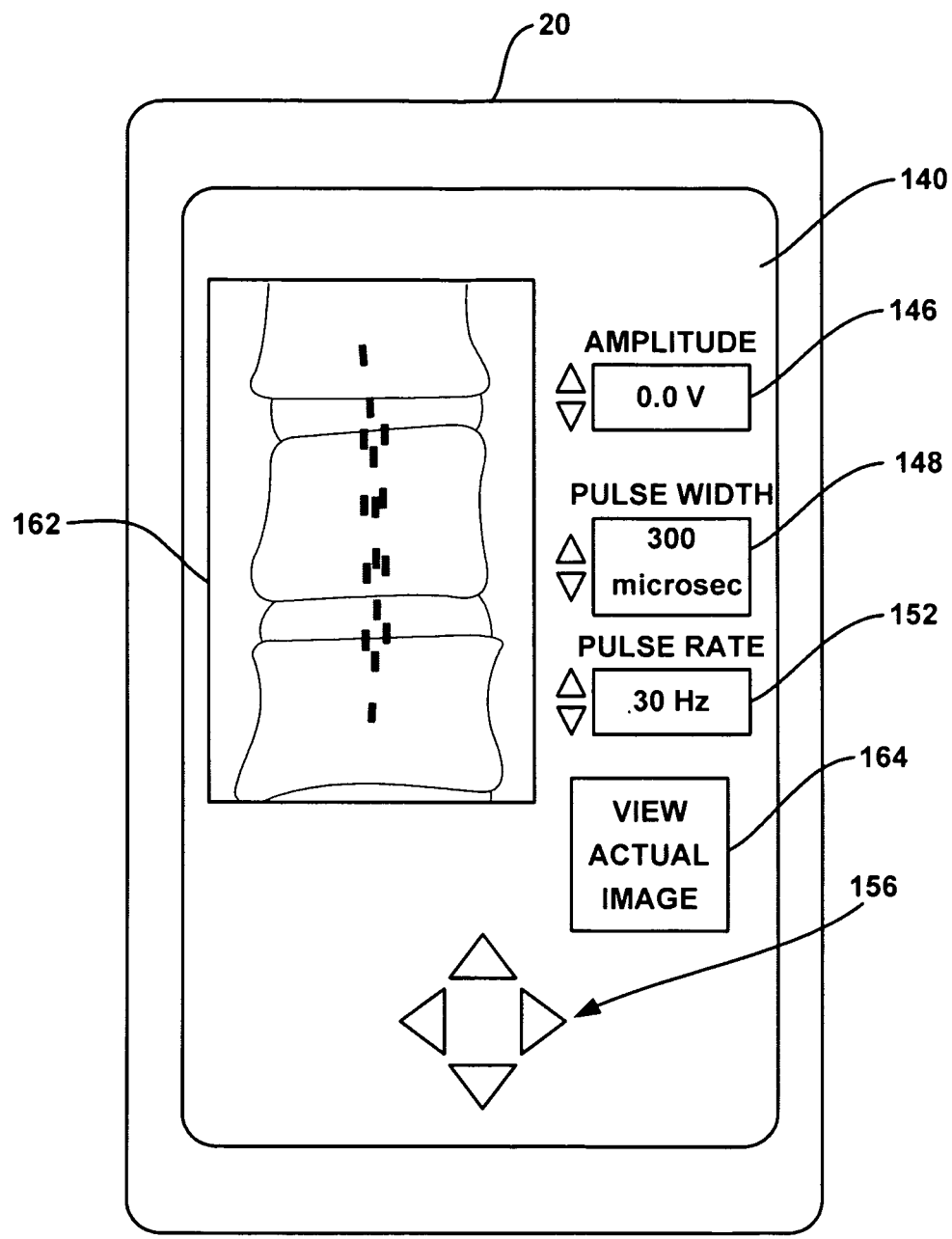
FIG. 16 is a conceptual diagram of the user interface of FIG. 13 showing a post-implant image viewing option.

FIG. 16 is a conceptual diagram of the user interface of FIG. 13 showing another post-implant image viewing option. In the example of FIG. 16, programmer 20 may be configured to permit a user to selectively view either a graphical representation of the lead configuration, such as the configuration of FIG. 13, 14 or 16, or an actual image of the lead configuration, as obtained by the imaging modality 50. The actual image, represented by reference number 162, may be a pixelized image that corresponds to the image obtained by imaging modality 50. The actual image 162 may be scaled down in spatial and/or gray scale resolution relative to the original image, and may be a gray scale image or a binarized image. In either case, the actual image 162 may provide a reasonable facsimile of the original image, and may serve as an alternative to viewing a graphical representation. The actual image 162 be displayed in place of the graphically represented image, or displayed in conjunction with the graphically represented image, e.g., side-by-side or otherwise adjacent to one another. As a further alternative, actual image 162 could be overlayed with the graphically represented image, e.g., using color or transparency to differentiate the two images. The user may selectively view the actual image by clicking on a button, such as the "View Actual Image" button 164 of FIG. 16. In some embodiments, by clicking on button 164 or some other input media, the user may toggle between the actual image of the implanted lead configuration and the graphical representation.

Figure 17:
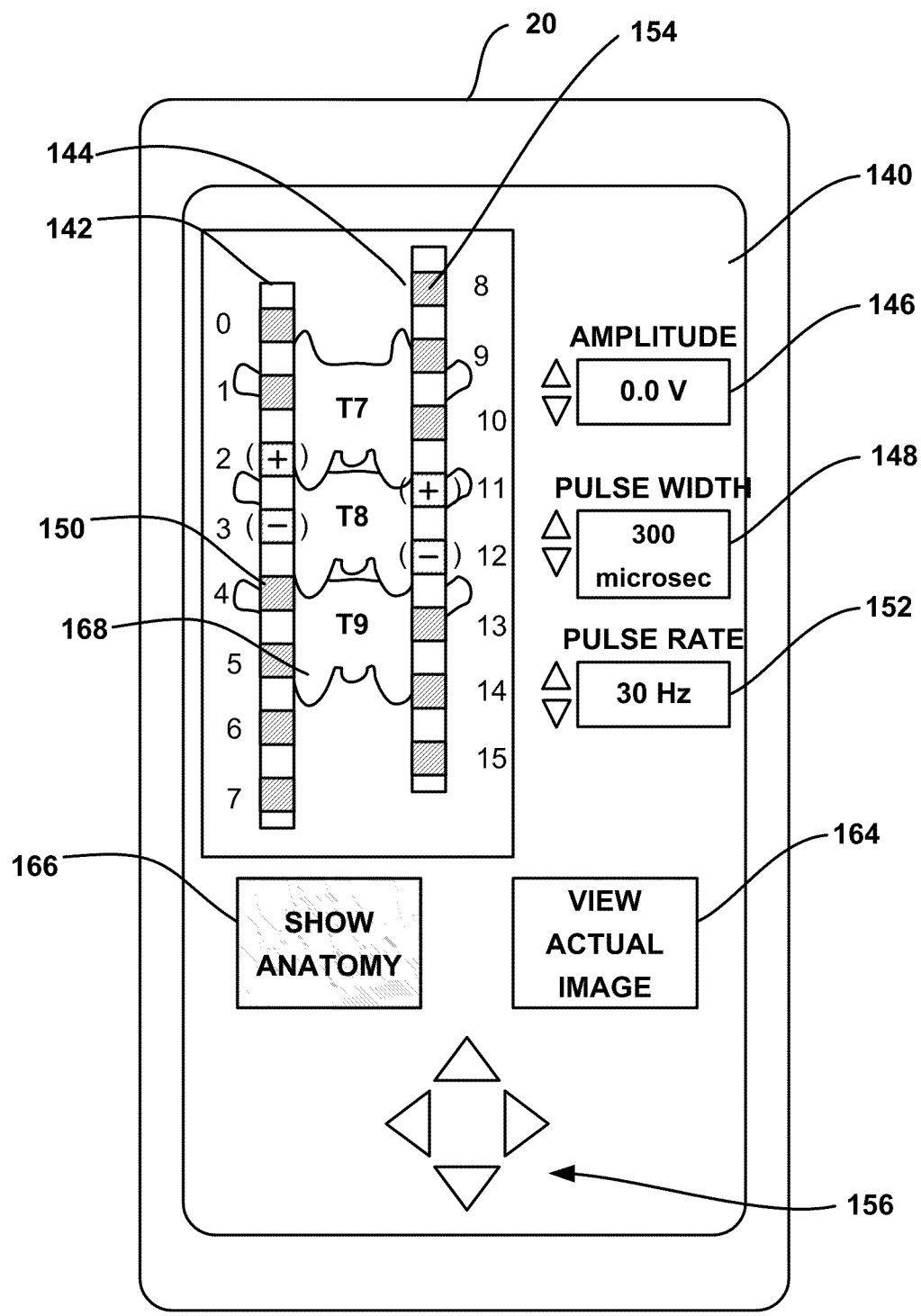
FIG. 17 is a conceptual diagram of the user interface of FIG. 13 showing an anatomical viewing option.

FIG. 17 is a conceptual diagram of the user interface of FIG. 13 showing an anatomical viewing option. As shown in FIG. 17, programmer 20 may present a graphical representation of leads 142, 144 and electrodes 150, 154 in conjunction with a graphical representation or actual image of one or more anatomical features, one of which is indicated by reference numeral 168. In the case of an SCS implantation, for example, leads 142, 144 may be displayed in overlay with selected vertebrae, such as the T7, T8 and T9 vertebrae. In some embodiments, the one or more anatomical features may be graphical depictions of such features. Alternatively, anatomical features may be actual image objects obtained from an actual image of the patient's anatomy.

Programmer 20 may be configured to permit a user to select graphical objects representing anatomical features, and then drag and drop them at desired locations relative to leads 142, 144. For example, the user may refer to the actual image to ascertain the positioning of the leads 142, 144 and electrodes 150, 154 relative to particular anatomical features, and then select and position graphical objects representing those in a foreground or background of the graphical representation of the leads. In some cases, programmer 20 may provide a drop down menu, a bitmap image directory, or other interface for selection of particular graphical objects.

To show anatomical features, and access any user interface features associated with viewing the anatomical features, a user may click on a button such as the "Show Anatomy" button 166 of FIG. 17. Upon clicking the button 166, the user may select the anatomical features and position them relative to the leads 142, 144 shown in the display 140 of FIG. 17. The anatomical features may be presented in combination with a simplified interface that shows constant horizontal spacing and/or constant vertical spacing between leads 142, 144, e.g., as shown in FIGS. 13 and 14. Alternatively, the anatomical features may be presented in combination with a more complex interface that shows an indication of actual horizontal spacing and/or constant vertical spacing between leads 142, 144 and electrodes 150, 154. Anatomical features also can be registered to the same scale and coordinates as the electrodes, allowing a "distance to target," i.e., a distance between an electrode and an anatomical target, to be used by programmer 20 in making automatic adjustments to stimulation parameters such as amplitude. For example, image processing device 52 or programmer 20 may ask the user to pick key landmarks on the anatomy in the image, e.g., by tracing aspects of anatomy such as vertebra, by atlas overlay, or by other techniques.

In other embodiments, image processing device 52 may apply pattern recognition processing to identify anatomical features within the image obtained from imaging modality 50, and generate relative positioning information that indicates the positions of the leads 142, 144, and/or electrodes 150, 154 relative to the anatomical features. The accuracy of the positioning relative to anatomical features may be coarse or fine depending on the processing power applied to resolve the anatomical features, and the complexity of the user interface presented by programmer 20.

In some cases, characterization unit 62 may include anatomical positioning data in the lead characterization data. The anatomical positioning data can be used by programmer 20 for presentation of the lead configuration in conjunction with anatomical features and/or adjustment of stimulation parameters associated with electrical stimulation delivered by different electrode combinations. In addition to relative spacing information between electrodes, image analysis unit 62 also may determine relative spacing between such electrodes and anatomical features such as particular vertebrae. For example, if the approximate spacing between an electrode and an anatomical target is known, programmer 20 may adjust one or more parameters as a function of the spacing to promote efficacy and/or power conservation. Adjustment of one or more stimulation parameters may refer to initial setting of parameters or modification of existing parameters. Techniques similar to those described above for determination of relative electrode spacing, or other techniques, may be used to determine spacing between electrodes or leads and anatomical features.

With relative positioning information for electrodes and one or more anatomical features, programmer 20 may implement pattern-directed programming and/or goal-directed programming. As an example, programmer 20 may be configured to apply pattern-directed programming to produce desired electrical stimulation field patterns such as guarded cathode, longitudinal triple, bipole, oval, teardrop or the like. In particular, using relative spacing information for different electrodes in the implanted lead configuration, programmer 20 may adjust one or more parameters and select different electrodes to produce the desired field patterns.

As another example, using relative spacing information for electrodes and one or more anatomical features, programmer 20 may be configured to apply goal-directed electrode avoidance by which particular electrodes in proximity to particular anatomical features are excluded from programmed electrode combinations. Examples include avoidance of selected electrodes to prevent significant stimulation of anatomical features such as the T9 vertebra or dorsal nerve in the case of spinal cord stimulation (SCS) or pelvic floor stimulation, or the anterior subthalmic nucleus (STN) in the case of deep brain stimulation (DBS).

As a further example, using relative spacing information for electrodes and one or more anatomical features, programmer 20 may be configured to apply goal-directed programming to stimulate particular anatomical features. Examples include selection of particular electrodes based on relative spacing information to stimulate anatomical features such as portions of the spinal cord superior and lateral of the T8 vertebra in the case of spinal cord stimulation (SCS).

In addition to relative positioning, in some embodiments, programmer 20 may display a graphical representation of the shape and size of an electrical stimulation field produced by selected electrode combinations for selected sets of stimulation parameters. Programmer 20 may present the stimulation field representation in conjunction with leads 142, 144 and electrodes 150, 154, e.g., in overlay. In addition, in some embodiments, the stimulation field representation may be displayed in combination with leads 142, 144, electrodes 150, 154 and one or more anatomical features. In this manner, the user interface may permit the user to better visualize the actual characteristics of the implanted lead configuration and the possible field effects of stimulation delivered via selected electrode combinations in the implanted lead configuration.

Figure 18:
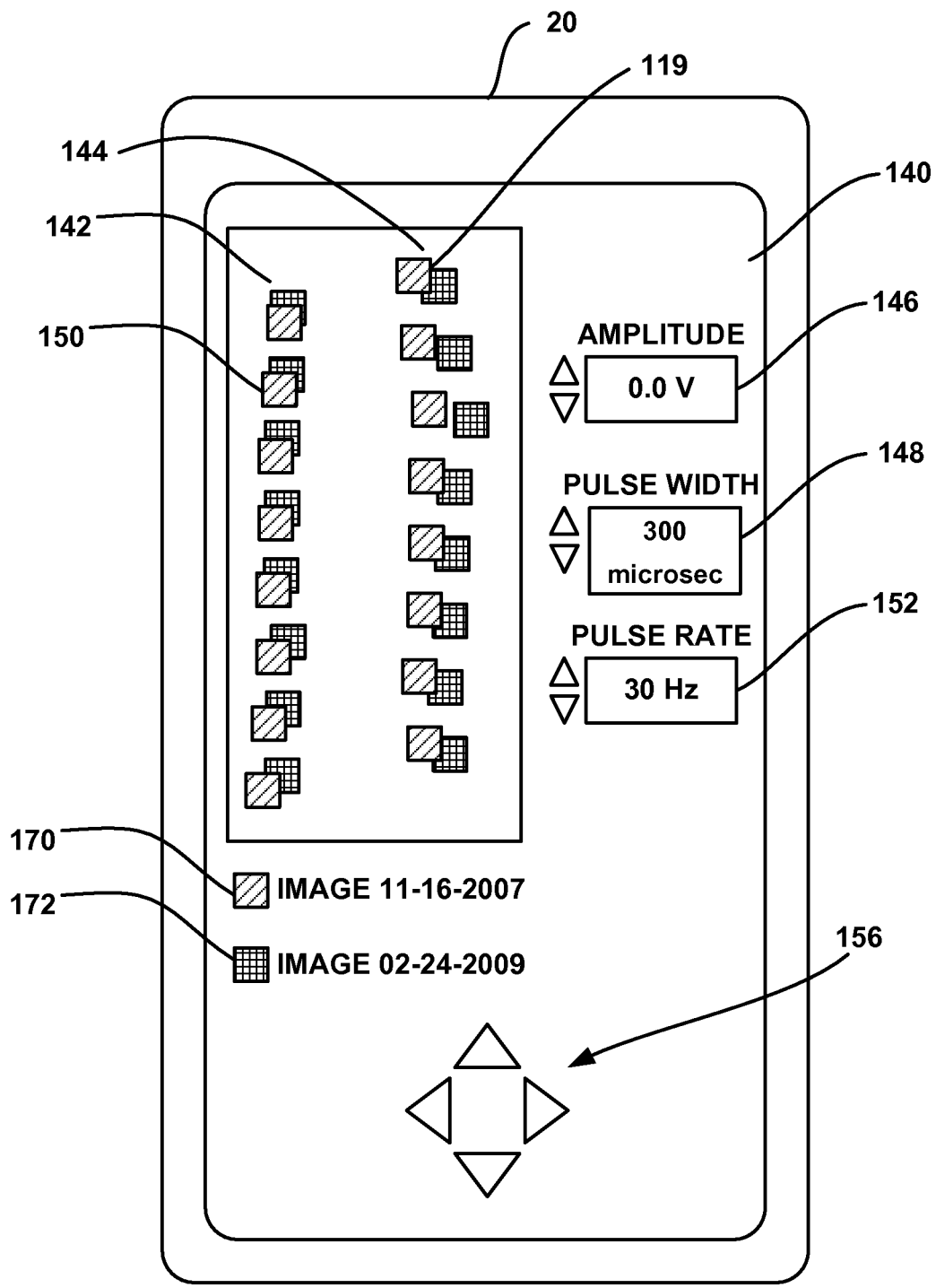
FIG. 18 is a conceptual diagram of the user interface of FIG. 13 showing another viewing option that permits comparison of multiple post-implant images to detect lead migration.

FIG. 18 is a conceptual diagram of the user interface of FIG. 13 showing another viewing option that permits comparison of multiple images to detect lead migration. In operation, imaging modality 50 may obtain a first image of the implanted lead configuration, e.g., a time shortly after the initial implantation, and a subsequent image at some later time. The first image may serve as a baseline image for comparison to the subsequent image.

Imaging modality 50 may be applied to obtain one or more subsequent images at different times throughout the course of therapy, e.g., several months later, a year later, several years later, or at regular or semi-regular intervals. Each of the subsequent images may be compared to the first, original image or to some other subsequent image taken after the initial implant. Each of the subsequent images may be processed in a manner similar to other post-implant images as described in this disclosure to produce lead characteristics. In some embodiments, image processing device 52 or programmer 20 may be configured to generate lead migration metrics, such as percentage of positional change or average change distance in millimeters. In addition, image processing device 52 or programmer 20 may be configured to determine when an electrode is no longer within a sufficient distance of the stimulation target such that stimulation may be ineffective. In this case, programmer 20 may notify the user that an electrode or electrodes are no longer within a target region that existed prior to lead migration.

Determination of some lead characteristics may be omitted from the analysis if they are not expected to vary from the first image, or some other subsequent image. For example, it may not be necessary to analyze electrode width and intra-lead electrode spacing, or perform lead orientation and lead type identification. Rather, it may be assumed in many instances that the same lead configuration is implanted. In these cases, the image analysis may focus on establishment of relative positioning information for spacing between electrodes and/or spacing between electrodes and anatomical features. In other cases, however, a more complete lead characterization including determination of electrode width and length, intra-lead electrode spacing, and lead orientation and lead type identification, may be desirable as a precaution to ensure that the same lead type is still implanted and have not been replaced or supplemented by additional leads.

Once image processing device 52 has generated an updated lead characterization for the subsequent image, programmer 20 may use the updated lead characterization data to display a graphical or actual representation of the lead configuration in the subsequent image. The lead configuration for the subsequent image may be displayed alone or in conjunction with the lead configuration from the first image. If lead configurations from the first and second images are displayed simultaneously, programmer 20 may display them in the same frame of reference so that the user may view positional differences between the electrodes and thereby detect lead migration.

In the example of FIG. 18, programmer 20 displays a graphical representation of a lead configuration consistent with a first image using a first type of cross-hatching, indicated by reference numeral 170. Programmer 20 displays a graphical representation of a lead configuration consistent with the subsequent image using another type of cross-hatching, as indicated by reference numeral 172. In addition, programmer 20 may display a date of the respective image, which may be provided as part of the lead characterization data. By viewing the graphical representations of the lead configurations, a user may readily detect positional changes that may result from lead migration due to axial movement, lateral movement, stretching, twisting or curvature of one or more leads in the lead configuration.

As a further option, the user may be permitted to view representations of the actual first and subsequent images of the lead configurations, e.g., in overlay with one another, as an alternative to graphical depictions of the lead configurations. Also, in some embodiments, image processing device 52 and programmer 20 may be configured to support presentation and analysis of lead configurations represented by one, two, three of more different post-implant images taken at different times. In this manner, a user may view a trend of lead migration, such as movement in a particular direction.

In addition to viewing positional changes, image processing device 52 may quantify positional electrode changes between different images, e.g., based on differences between pixel coordinate values associated with the electrodes. In some embodiments, programmer 20 may present the quantified positional changes, e.g., by displaying numeric values on display 140. A user may view changes for a selected electrode by clicking on the electrode one or more times, in which case programmer 20 may present a numeric value indicating the positional difference of the electrode between the first image and the subsequent image. In addition, programmer 20 may permit the user to view spacing between pairs of electrodes, e.g., in a manner similar to that described with reference to FIG. 15.

As a further feature, in some embodiments, programmer 20 may process the positional difference information provided by the lead characterization data to adjust one or more stimulation parameters, such as voltage or current amplitude, pulse width, pulse rate, duty cycle, electrode combination and/or electrode polarity, where adjustment of stimulation parameters refers to setting of parameters or modification of previously set parameters. If a currently selected program defines a first set of a parameters for a given electrode combination, but the positional difference information indicates a substantial positional shift, programmer 20 may adjust one of more of the parameters based on the shift. In the above manner, image analysis unit 60 may analyze the first and subsequent image and programmer 20 may automatically generate an adjustment to one or more parameters based on a difference between the first and second images.

For example, if lead migration causes the shift to exceed a predetermined threshold, it may be determined that the optimality of the currently selected parameters may be compromised. On this basis, if programmer 20 detects a shift that exceeds the threshold, the programmer may adjust one or more parameters based on the magnitude of the shift, the direction of the shift, or other characteristics. Alternatively, or additionally, programmer 20 may generate a message that advises the user of a significant lead migration that may require user attention, e.g., in order to adjust therapy settings to maintain a desired therapeutic effect. Hence, programmer 20 may be configured to detect lead migration, quantify the extent of lead migration and advise the user that significant lead migration has occurred.

As an illustration, a given electrode combination in the lead configuration may include a cathode and anode separated by a spacing of 20 mm in the first image. If the subsequent image indicates that lateral and/or vertical lead migration has caused the cathode and anode to shift away from one another to a spacing of 28 mm, programmer 20 may increase a voltage or current amplitude of the stimulation delivered via the electrode combination to compensate for the wider spacing across the patient tissue. Conversely, programmer 20 may decrease amplitude if the spacing has decreased due to lateral and/or vertical lead migration.

In each case, the increase or decrease may be a function of the degree of spacing difference between the electrodes according to the first image and the subsequent image. Programmer 20 additionally or alternatively may be configured to select or adjust parameter values based on positional differences between electrodes and anatomical features, e.g., a change in proximity of an electrode to a specific dorsal root nerve. In addition to selecting or adjusting parameters, in some cases, programmer 20 may be configured to select a different electrode combination either automatically or as a proposed combination for review and approval by the user.

Hence, image processing devisee 52 may analyze the post-implant image and determine a relationship of at least some of the electrodes relative to one or more anatomical structures within the patient based on the analysis. The relationship may be expressed, for example, by relative positioning data provided in the lead characterization data provided to programmer 20. By reference to the lead characterization data, programmer 20 may automatically generate an adjustment to the electrical stimulation therapy delivered via the lead configuration based on the analysis and the determined relationship between the electrodes and the anatomical feature or features.

As described above, programmer 20 may automatically specify adjustments to one or more parameters based on an updated lead characterization. In this manner, programmer 20 may reduce time and effort of a user in evaluating lead migration and selecting adjustments to compensate for the lead migration. Instead, with the aid of updated lead characterization data from image processing device 52, programmer 20 may automatically present accurate, comparative imagery and positional difference data that represents the actual extent of lead migration, and also automatically specify one or more adjustments to compensate for the lead migration.

For ease of illustration, situations in which the implanted leads migrate in two dimensions (vertically and horizontally) have been described above. However, in some situations, the implanted lead may migrate in the third (depth) dimension. For example, the top of one lead may migrate in the depth dimension, while the bottom of the lead remains in the same position. The techniques described above are applicable to lead migration in the depth dimension.

For example, if one lead migrates at an angle so that it is deeper than the other lead, or posture changes cause the cerebral spinal fluid to compress and therefore one or more leads migrate closer to the target neurons in the spinal cord, one or more of its electrodes may appear to be smaller than others on that lead. The migration in the depth dimension may be calculated by determining the difference in location of the top electrode and the bottom electrode. For example, image processing device 52 may analyze different sizes of the electrodes in a two-dimensional image to estimate differences in depth, on the assumption that deeper electrodes will appear smaller and that shallower electrodes will appear larger. However, this process may benefit from relatively high resolution images. In this manner, depth may be estimated by analysis of a single two-dimensional image.

Alternatively, to determine migration in the depth dimension, multiple images may be taken, e.g., where one image is taken sagitally and the other is taken axially, such that multiple, two-dimensional images from different perspectives are available. Additionally, or alternatively, other imaging modalities may be used to generate a three dimensional; picture. For example, a magnetic resonance imaging (MRI) or computed tomography (CT) image may be used to capture multiple planes and thereby ascertain the depth of particular electrodes relative to other electrodes and/or relative to anatomical features. In such cases, two dimensional slices, sagitally and axially, of the image may be generated, and the techniques described above may be used on each slice. Accordingly, identifying lead types and relative position may be calculated for three dimensional images.

Some implantable stimulation leads may have complex electrode array geometries. Complex electrode array geometries may include multiple electrodes at different axial and angular positions. A complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead. Another example of a simple electrode array geometry is a planar array of electrodes on a paddle lead.

An example of a complex electrode array geometry is an array of electrodes positioned at different axial positions along the length of a lead, as well as at different angular positions about the circumference of the lead. In some embodiments, the electrodes in the complex array geometry may appear similar to non-contiguous, arc-like segments of a conventional ring electrode. A lead with a complex electrode array geometry may include multiple rings of electrode segments. Each ring is disposed at a different axial position. Each electrode segment within a given ring is disposed at a different angular position. The lead may be cylindrical or have a circular cross-section of varying diameter.

To identify lead configurations with complex electrode array geometries, image processing device 52 may analyze a 3D image or multiple two dimensional images. For example, image processing device 52 may determine axial orientation or rotation for leads that are axially asymmetric. It may be clinically relevant to know the axial orientation of a cylindrical electrode split into three segments. Identification of the location of a fiducial marker, such as a stripe on the surface of an electrode, an electrode with a clipped corner, an electrode with some other characteristic, on two or more axial images may allow the rotational orientation of the lead to be matched to anatomical targets or absolute orientation, e.g., if the angles at which the images or slices were taken is known. Anatomical landmarks such as bone structures or other anatomical features also may be useful in determining orientation or rotation of nonsymmetrical electrode arrays, including electrode arrays carried by non-symmetrical leads such as segmented leads having electrodes at various angular positions around the circumference of the lead.

Figure 19:
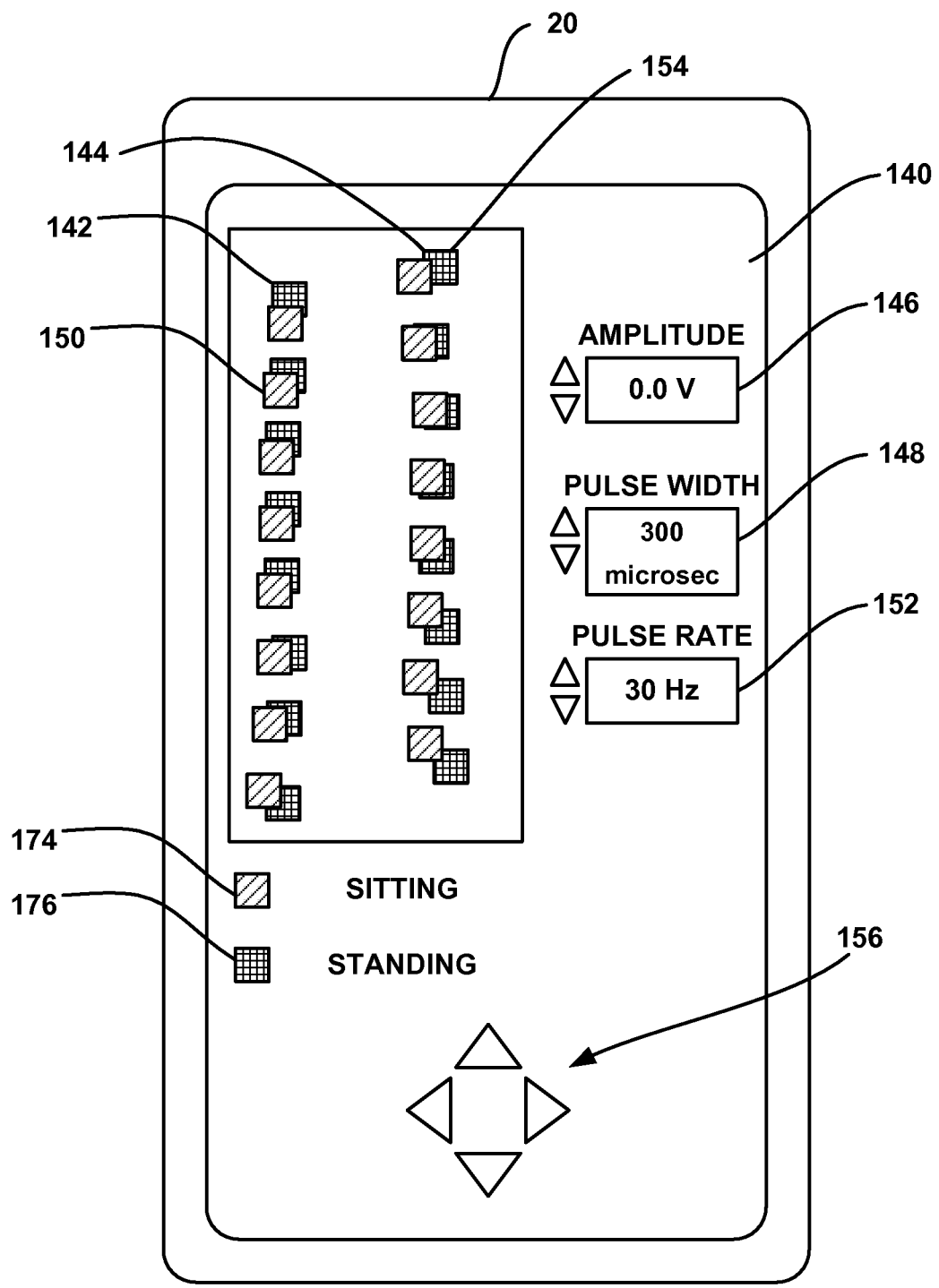
FIG. 19 is a conceptual diagram of the user interface of FIG. 13 showing another viewing option that permits comparison of multiple images to detect lead positions for different postures.

FIG. 19 is a conceptual diagram of the user interface of FIG. 13 showing another viewing option that permits comparison of multiple images to detect lead positions for different postures. As mentioned previously, leads 16 may migrate on a short-term or longer-term basis. Patient posture changes, for example, may cause consistent, short-term lead migration between different positions for different postures. If programmer 20 is equipped to generate different stimulation programs for different postures, which may be activated either in response to posture sensing or patient input, then it may be desirable to view lead positional changes among different postures. Examples of different postures may include sitting, standing, lying down, or the like. In addition, different activities such as working, resting, sleeping, exercising or the like may present different lead configuration positions.

Programmer 20, in some embodiments, may be configured to present a graphical depiction or actual imagery representing the lead configuration based on analysis of images obtained when the patient is in different postures or engaged in different activities. In the example of FIG. 19, different cross-hatching may be used, as indicated by reference numerals 174 and 176, to represent electrode positions in different postures such as sitting and standing. Using this information, the user may perceive positional electrode differences in different postures or different activities and make more informed programming decisions.

Alternatively, or additionally, programmer 20 may be configured to quantify positional differences and specify adjustments to stimulation parameters associated with programs defined for different postures or activities in order to compensate for the positional differences. If a lead stretches or twists, for example, when a user is sitting relative to when the user is standing, electrodes associated with an electrode combination may be further apart when the user is sitting. In this case, programmer 20 may modify one or more parameters, such as amplitude, as a function of the degree of spacing difference between electrodes.

In this manner, programmer 20 may promote better efficacy of the stimulation when the patient is in various postures or engaged in different activities. In particular, relative positioning information obtained from images associated with different postures or activities can assist with programming of therapy for posture specific settings in combination with physician desired electrode settings to autogenerate programs or groups of programs for different postures or activities.

Accordingly, image processing device 52 may analyze a first electronic image of an electrical stimulation lead implanted within a patient when the patient is in a first posture, and analyze a second electronic image of an electrical stimulation lead implanted within a patient when the patient is in a second posture, and programmer 20 may automatically generate adjustments to electrical stimulation therapy configured for delivery via the lead when the patient is in a first posture based on the analysis of the first image, and automatically generate adjustments to electrical stimulation therapy configured for delivery via the lead when the patient is in a second posture based on the analysis of the second image. Again, application of the adjustment may be automatic or subject to review and approval by a user.

Figure 20A:
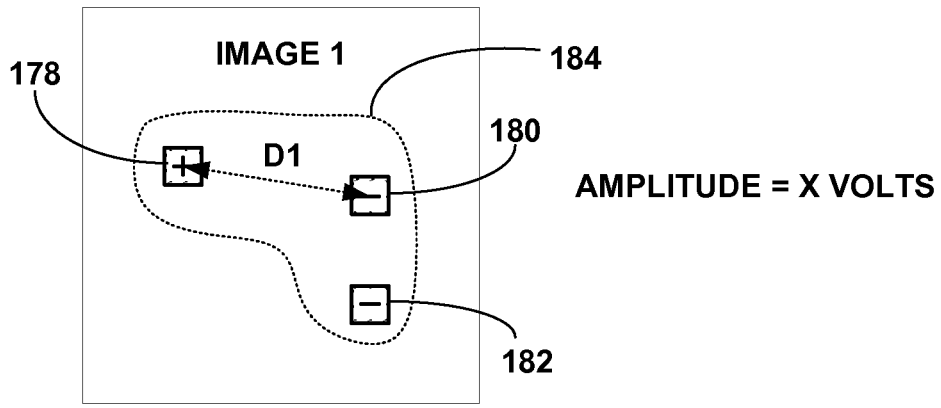
FIGS. 20A, 20B and 20C are diagrams showing differences in inter-lead electrode spacing due to lead migration.
Figure 20B:
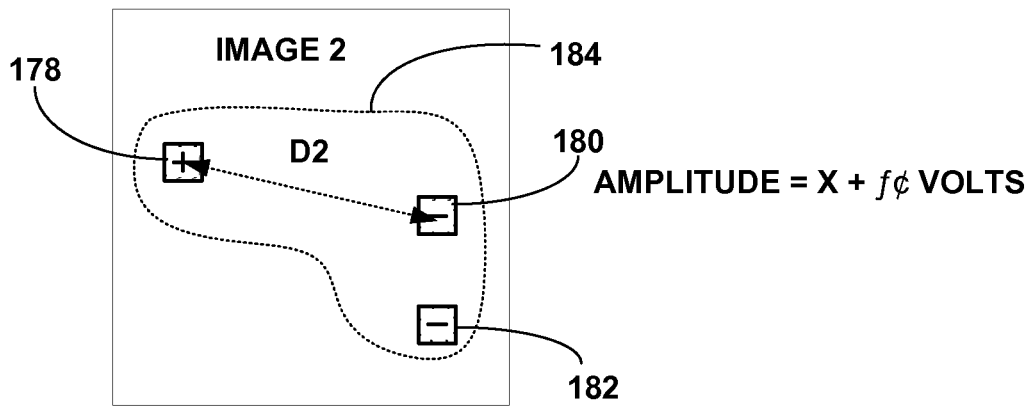
Figure 20C:
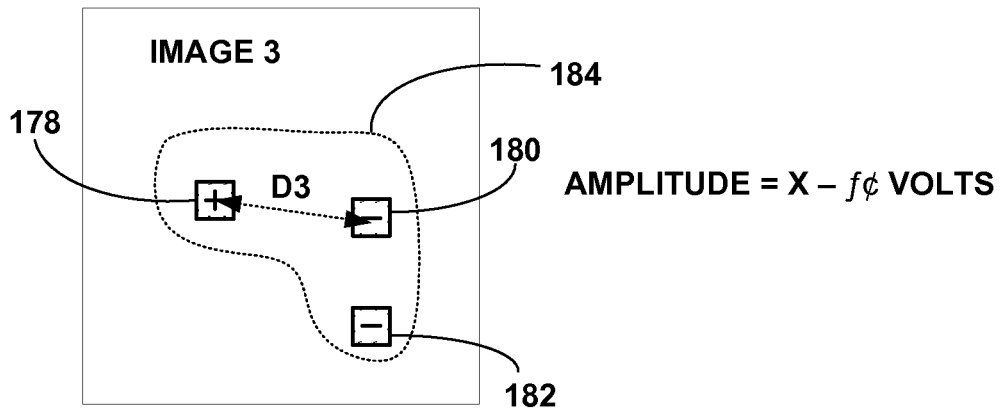

FIGS. 20A, 20B and 20C are diagrams showing differences in inter-lead electrode spacing due to lead migration. FIGS. 20A-20C provide a simplified representation of positional differences that may be observed by analysis of post-implant imagery. In the example of FIG. 20A, a selected electrode combination includes cathode 178 on a first lead and anodes 180 and 182 on a second lead. Application of stimulation energy between electrodes 178, 180, 182 produces an electrical stimulation field 184 that may be applied to an anatomical target to support any of a variety of therapies. Accordingly, FIGS. 20A-20C also illustrate the representation of an electrical stimulation field that models an approximation of the actual field that would be generated by the selected electrode combination given a specified set of stimulation parameters.

As indicated by Image 1 of FIG. 20A, the distance between electrode 178 and 180 is D1 and the stimulation amplitude is X volts. As indicated by Image 2 of FIG. 20B, the distance between electrode 178 and 180 is D2, which is greater than D1. In this case, programmer 20 may automatically adjust the amplitude of the stimulation based on the difference between D1 and D2 to increase the amplitude to a level of X+A volts and maintain the field 184 for therapeutic efficacy. As indicated by Image 3, the distance between electrode 178 and electrode 180 is D3, which is less than D1. In this case, programmer 20 may automatically adjust the amplitude of the stimulation based on the difference between D3 and D1 to decrease the amplitude to a level of X–Δ volts and thereby maintain field 184 but also conserve power resources.

As noted above, techniques in addition to ones described above may be utilized to define a bounding rectangle for each of the blobs, i.e., electrodes. The bounding rectangle may be used to find the size of the electrode (e.g., length and width). One such example technique to define the bounding rectangle, referred to as size estimation, comprises centering an observing rectangle on each blob center point in the black and white image (e.g., FIG. 11C). As described above, the center point for each blob has already been ascertained utilizing the morphological algorithm or user assistance, for example. Initially, the length and width of the observing rectangle may be smaller than the length and width of the blob. Accordingly, the binary pixel value for each pixel within the observing rectangle, as initially sized and oriented, may be 1. As noted above, a pixel value of 1 indicates that the pixel is black, while a pixel value of 0 indicates that the pixel is white. The ratio of the length to width of the observing rectangle may be 3:2; however, other ratios may be used as well. The observing rectangle may then be stretched lengthwise and widthwise while keeping the length to width ratio at 3:2, according to one aspect.

The observing rectangle may be stretched lengthwise and widthwise until the observing rectangle overspills the blob. In one example, overspill is defined as an amount of the area of the observing rectangle that is outside the bounds of the blob. Stated another way, overspill is, in this example, the number of pixels within the blob whose pixel value is 0. The overspill may be calculated by summing the number of pixels that are within the observing rectangle that have a pixel value of 0. The amount of tolerable overspill may be predefined as an overspill threshold value. The overspill threshold value may be defined as a percentage of pixels in the blob with pixel value 0 relative to the total number of pixels within the observing rectangle. For example, after the observing rectangle is stretched lengthwise and widthwise, the total number of pixels with pixel value 0 may be 20% of the total number of pixels within the observing rectangle. In this example, 80% of the pixels within the observing rectangle will have a pixel value of 1 and 20% of the pixels within the observing rectangle will have a pixel value of 0. In one example, the overspill threshold value may be 20%.

After the observing rectangle is stretched lengthwise and widthwise until the overspill is greater than the overspill threshold value, the observing rectangle may be rotated and the amount of overspill may be recalculated for the rotated observing rectangle and compared to the overspill threshold value. In one example, the observing rectangle may be rotated by 10 degrees. However, a rotational angle may be greater than or less than 10 degrees. If the overspill is less than the overspill threshold value, the observing rectangle may be stretched lengthwise and widthwise until the overspill is greater than the overspill threshold value. The observing rectangle may be stretched lengthwise and widthwise; however, the ratio between the length and width of the observing rectangle may remain at 3:2.

If, after the observing rectangle is rotated, the overspill is greater than the overspill threshold value, the observing rectangle is rotated once again, by 10 degrees as one example, and the acts of comparing the overspill to the overspill threshold value and stretching the observing rectangle are repeated until the observing rectangle has been rotated a full 360 degrees. The observing rectangle may be rotated in a clockwise or counter clockwise fashion. The final width of the observing rectangle defines an approximation of the width of the blob, i.e., electrode. Stated another way, the final width of the observing rectangle where the overspill is less than the overspill threshold value defines an approximation of the width of the electrode. The number of the pixels along the width of the observing rectangle defines the width of the electrode.

Once the width of the electrode is ascertained from the size estimation technique described above, the dimension of each pixel, in one example, may be calculated substantially similar to the techniques described above. For example, as described above, a regression fit technique may be utilized to determine which electrodes belong to which lead. After the lead is identified, characterization unit 62 extracts electrode geometries to determine the lead type of the identified lead. After the lead type is determined, characterization unit 62 can determine the dimensions of each pixel. For example, as stated earlier, using a 1×8 compact lead (corresponding to lead 80 of FIG. 6 and Table 1 and center lead 128 of FIG. 11C), for example, characterization unit 62 can determine that the 12 pixel spacing between electrodes corresponds to 4 mm. The 4 mm spacing is known from the lead characteristics of the known 1×8 compact lead 80. Hence, characterization unit 62 can determine that 1 mm equals 3 pixels.

As another example, as seen in Table 1, the electrode width for every lead may be 1.5 mm. Once the width of the electrode is ascertained using the size estimation algorithm, the dimensions of each pixel may be calculated by dividing 1.5 mm by the number of pixels along the observing rectangle. For example, if the width of the observing rectangle is 3 pixels, then the dimension of each pixel may be 0.5 mm (i.e., 1.5 divided by 3).

Figure 21A:
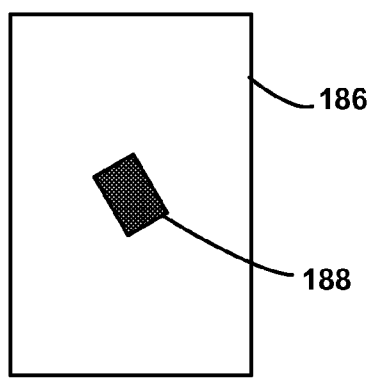
FIGS. 21A-21E are example electrode and observing rectangle diagrams that illustrate an electrode size estimation technique

FIGS. 21A-21E are example electrode and observing rectangle diagrams that illustrate an electrode size estimation technique. Image analysis unit 60 within image processing device 52 (FIG. 5B) may initially generates observing rectangle 188 centered within electrode 186 as shown in FIG. 21A. Observing rectangle 188 may not be displayed to a user and the techniques described with respect to FIGS. 21A-21E may be performed within image processing device 52 with little to no user assistance. For purposes of clarity and illustration, electrode 186 is shown in white and observing rectangle 188 is shown in black to clearly differentiate between electrode 186 and observing rectangle 188. Notably, electrode 186 on the actual black and white image may be black. In some examples, observing rectangle may comprise a length to width ratio of 3:2; however, other ratios are also contemplated by this disclosure.

Observing rectangle 188 is stretched lengthwise and widthwise. Image analysis unit 60 may stretch observing rectangle 188 lengthwise and widthwise in increments of 1%, as one example. The 1% incremental stretching is provided merely for purposes of illustration. In different examples, observing rectangle 188 may be stretched in increments greater or less than 1%. However, in any incremental stretching the 3:2 length-to-width ratio of observing rectangle 188 may need to be maintained, according to one embodiment.

After every incremental stretching of observing rectangle 188, image analysis unit 60 calculates any possible overspill of observing rectangle 188. Image analysis unit 60 determines the total number of pixels within observing rectangle 188 based on the pixel coordinates of each pixel and the boundaries of observing rectangle 188. Techniques for determining whether a pixel resides within observing rectangle 188 is described in more detail with respect to FIG. 23. Additionally, image analysis unit 60 determines the total number of pixels within observing rectangle 188 with pixel value 0.

Image analysis unit 60 then calculates the overspill by dividing the total number of pixels within observing rectangle 188 with pixel value 0 by the total number of pixels within observing rectangle 188. If the divided value is less than or equal to an overspill threshold value, e.g., 20%, image analysis unit 60 stretches observing rectangle 188 by another 1% increment. Image analysis unit 60 then again calculates the overspill, and the process repeats until the overspill is greater than the overspill threshold value. If the divided value is greater than the overspill threshold value, image analysis unit 60 rotates observing rectangle 188 in a clockwise fashion. In some examples, image analysis unit 60 rotates observing rectangle 188 in 10 degree increments, as one example. The 10 degree incremental rotation is provided merely for purposes of illustration. In different examples, observing rectangle 188 may be rotated in increments greater or less than 10 degrees. Furthermore, the clockwise rotation is also provided for purposes of illustration. In different examples, observing rectangle 188 may be rotated in a counter-clockwise fashion.

Figure 21B:
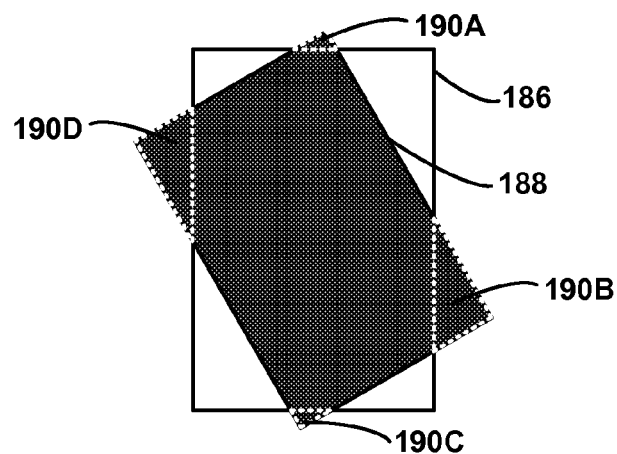

FIG. 21B illustrates observing rectangle 188 stretched from its initial orientation as shown in FIG. 21A. As shown in FIG. 21B, observing rectangle 188 overspills electrode 186. The overspill regions 190A-190D are indicated by the white dashed lines where observing rectangle 188 overspills electrode 186. Overspill regions 190A-190D indicate regions within observing rectangle 188 where the pixel value for the pixels is 0. For purposes of illustration, it should be assumed that overspill regions 190A-190D comprise more than 20% of the total number of pixels within observing rectangle 188. In accordance with this disclosure, when observing rectangle 188 is stretched from its initial orientation, as shown in FIG. 21A, to the orientation shown in FIG. 21B, the overspill of observing rectangle 188 is greater than the overspill threshold value, e.g., 20%. As described above, once the overspill is greater than the overspill threshold value, image analysis unit 60 rotates observing rectangle 188.

Figure 21C:
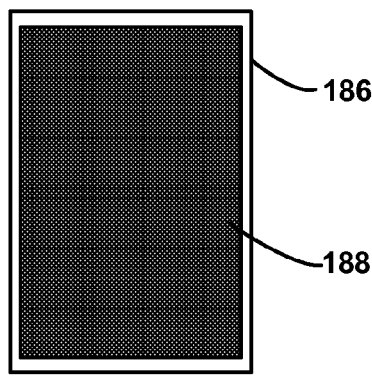

FIG. 21C illustrates observing rectangle 188 rotated from its orientation shown in FIG. 21B. Image analysis unit 60 may then calculate the overspill of observing rectangle 188. As shown in FIG. 21C, observing rectangle 188 is completely encompassed by electrode 186. Accordingly, image analysis unit 60 may determine that there is no overspill. Image analysis unit 60 may then stretch observing rectangle 188 lengthwise and widthwise will maintaining a 3:2 length-to-width ratio for observing rectangle 188.

Figure 21D:
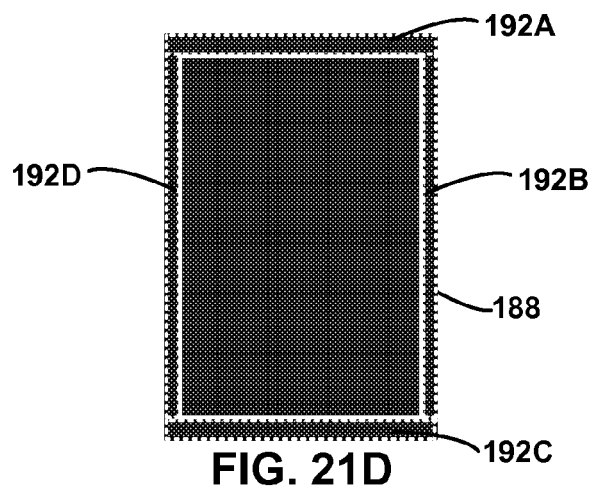

FIG. 21D illustrates observing rectangle 188 stretched lengthwise and widthwise from its orientation in FIG. 21C. Image analysis unit 60 stretched observing rectangle 188 in 1% increments and determined the overspill after each incremental stretch. As described above, observing rectangle 188 is stretched as long as the overspill is less than or equal to the overspill threshold value. As shown in FIG. 21D, observing rectangle 188 completely encompasses electrode 186 be, accordingly electrode 186 is not clearly discernible in FIG. 21D. Though not explicitly referenced in FIG. 21D, for purposes of illustration, electrode 186 is shown as a solid white line rectangle that is completely encompassed by observing rectangle 188. In FIG. 21D, image analysis unit 60 stretched observing rectangle 188 until the overspill became greater than the overspill threshold value. The overspill is represented by overspill regions 192A-192D. The overspill regions 192A-192D are indicated by the white dashed lines where observing rectangle 188 overspills electrode 186. The pixel value is 0 for the pixels within overspill regions 192A-192D. Image analysis unit 60 may then rotate observing rectangle by 10 degrees.

Figure 21E:
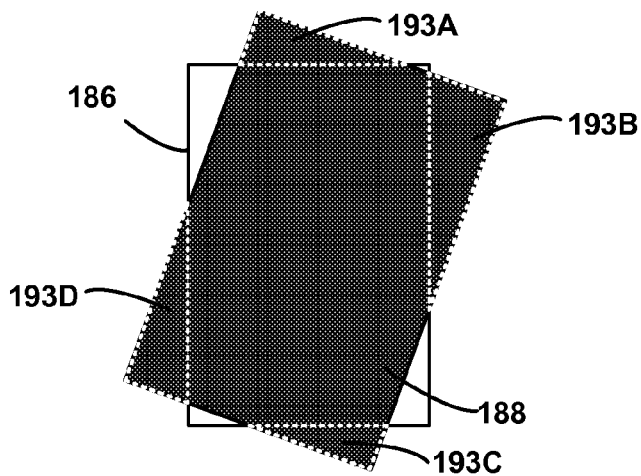

FIG. 21E illustrates observing rectangle 188 rotated from its orientation in FIG. 21D. As shown in FIG. 21E, observing rectangle 188 overspills electrode 186. The overspill regions 193A-193D are indicated by the white dashed lines where observing rectangle 188 overspills electrode 186. Overspill regions 193A-193D indicate regions within observing rectangle 188 where the pixel value for the pixels is 0. For purposes of illustration, it should be assumed that overspill 192A-192D comprise more than 20% of the total number of pixels within observing rectangle 188. As shown in FIG. 21E, the overspill of observing rectangle 188 is greater than the overspill threshold value, e.g., 20%. As described above, once the overspill is greater than the overspill threshold value, image analysis unit 60 rotates observing rectangle 188. In the example shown in FIG. 21E, image analysis unit 60 may not stretch observing rectangle 188 because the overspill of observing rectangle 188 is already greater than the overspill threshold value.

Image analysis unit 60 may rotate observing rectangle 188 once more. Though not shown in the FIGS., it is noticeable that as image analysis unit 60 rotates observing rectangle 188, the overspill for all additional orientations will be greater than the overspill threshold value. Image analysis unit 60 may rotate observing rectangle 188 a full 360 degrees. Stated another way, image analysis unit 60 may keep rotating observing rectangle 188 and determining whether the overspill is greater than the overspill threshold value until image analysis unit 60 has rotated observing rectangle 188 a full 360 degrees.

After image analysis unit 60 has rotated observing rectangle 188 a full 360 degrees, the final width of observing rectangle 188 may be the width of electrode 186. Moreover, the number of pixels along the width of observing rectangle 188 defines an approximation of the width of the electrode, i.e., the pixel width. However, the width of the observing rectangle may be greater than the width of the electrode because the observing rectangle is stretched until the overspill is greater than the overspill threshold value. For a better approximation of the width of the electrode, the width of observing rectangle 188 may, in some instances, be reduced based on the overspill threshold value. For example, if the overspill threshold value is 20%, the width of observing rectangle may be reduced by 20% to provide a potentially more accurate approximation of the width of the electrode. As described above, based on the pixel width and the regression fit technique described above to find the lead type, the dimensions of each pixel may then be calculated. The dimensions of each pixel may then be utilized to calculate relative distances between the identified lead types as described above.

Alternatively, as described above, as another example, as seen in Table 1, the electrode width for every lead is 1.5 mm. Once the width of the electrode is ascertained using the size estimation algorithm as described with respect to FIGS. 21A-21E, the dimensions of each pixel may be calculated by dividing 1.5 mm by the number of pixels along the observing rectangle. For example, if the width of the observing rectangle is 3 pixels, than the dimension of each pixel may be 0.5 mm (e.g., 1.5 divided by 3).

Figure 22:
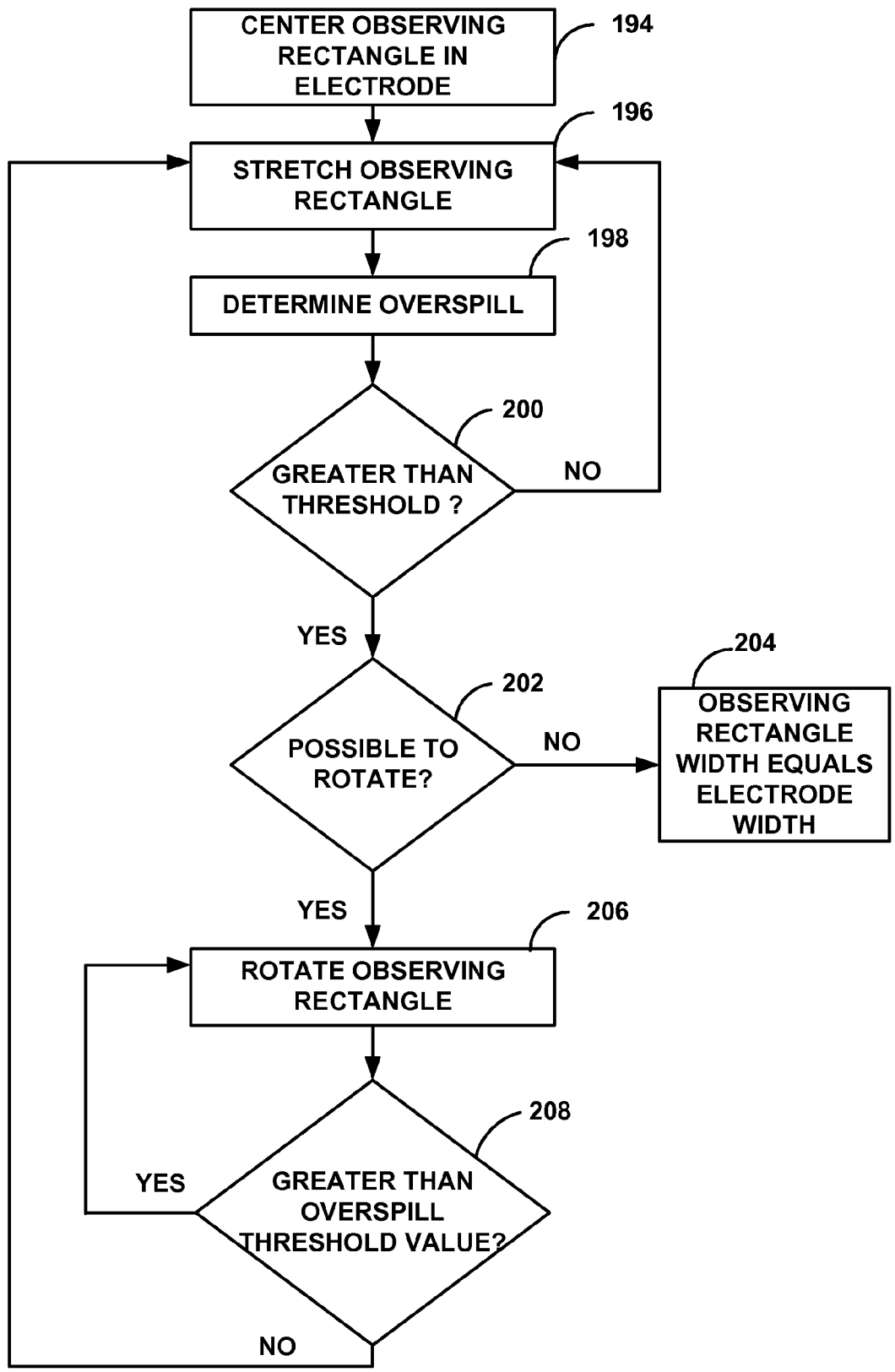
FIG. 22 is a flow chart diagram illustrating an example operation of the electrode size estimation technique.

FIG. 22 is a flow chart diagram illustrating an example operation of the electrode size estimation technique. For purposes of illustration, reference will be made to FIG. 5B. Image analysis unit 60 centers an observing rectangle within a blob, i.e., electrode, of the black and white image (194). As described above, the center of each of the electrodes is determined utilizing the morphological algorithm or user assistance, according to one example. The observing rectangle may be smaller than the electrode and the length-to-width ratio of the observing rectangle may be 3:2. Image analysis unit 60 may then stretch the observing rectangle by a predefined increment, e.g., 1%, while still maintaining the 3:2 ratio (196). Image analysis unit 60 may then determine the overspill (198). Image analysis unit 60 may determine the total number of pixels within the observing rectangle with pixel value of 0 and the total number of pixels within the observing rectangle. Image analysis unit 60 may divide the total number of pixels within the observing rectangle with pixel value of 0 by the total number of pixels within the observing rectangle to determine the overspill.

Next, image analysis unit 60 may determine whether the overspill is greater than an overspill threshold value (200). If the overspill is less than the overspill threshold value (NO of 200), image analysis unit 60 may further stretch the observing rectangle (196). If the overspill is greater than the overspill threshold value (YES of 200), image analysis unit 60 may determine whether the observing rectangle can be rotated (202). The observing rectangle may be rotated (YES of 202), if the observing rectangle has not be fully rotated 360 degrees. The observing rectangle may not be rotated (NO of 202), if the observing rectangle has already been fully rotated 360 degrees. If the observing rectangle cannot be rotated, then the size estimation algorithm ends and the width of the observing rectangle is an approximation of the width of the electrode (204). Stated another way, image analysis unit 60 approximates the electrode width based upon a width of the observing rectangle after the observing rectangle has been fully rotated. In some examples, for a better approximation of the width of the electrode, the width of the observing rectangle may be reduced by the percentage that defined the overspill threshold value. For example, if the overspill threshold value is 20%, the width of the observing rectangle may be reduced by 20% to provide a better approximation of the width of the electrode.

If the observing rectangle can be rotated (YES of 202), image analysis unit 60 rotates the observing rectangle (206). In some examples, image analysis unit 60 may rotate the observing rectangle by 10 degrees. Next, image analysis unit 60 determines whether the overspill of the observing rectangle is greater than the overspill threshold value (208). If the overspill of the observing rectangle is greater than the overspill threshold value (YES of 208), image analysis unit 60 rotates the observing rectangle (206). If the overspill of the observing rectangle is less than the overspill threshold value, image analysis unit 60 stretches the observing rectangle (196).

Figure 23:
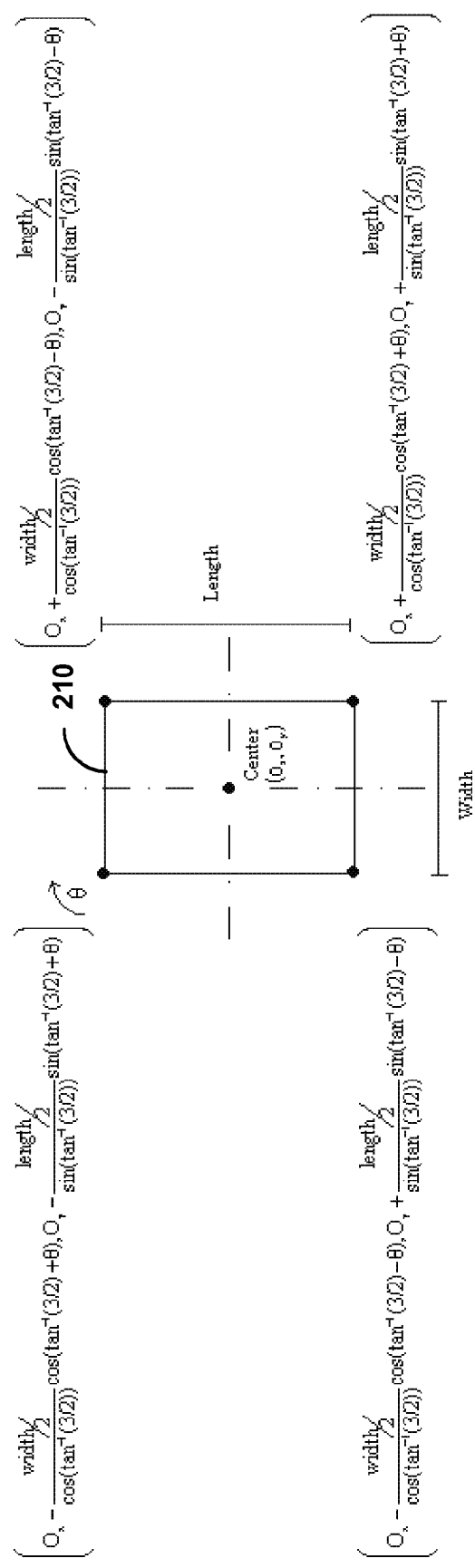
FIG. 23 is a diagram illustrating equations for calculating the corner coordinates for an observing rectangle.

As described above, image analysis unit 60 may rotate the observing rectangle when the overspill of the observing rectangle is greater than the overspill threshold value. Image analysis unit 60 may utilize trigonometry to rotate a rectangle along a fixed point, i.e., along the center of the electrode. FIG. 23 is a diagram illustrating equations for calculating the corner coordinates for observing rectangle 210. As shown in FIG. 23, based on the coordinates of the center of observing rectangle 210 (e.g., ($O_x$, $O_y$)), the rotational angle (e.g., $\Theta$), the length of observing rectangle 210, the width of observing rectangle 210, and a known ratio of the length-to-width of observing rectangle 210 (e.g., 3:2), the coordinates for the corners of observing rectangle 210 may be calculated based on the following equations.

The coordinates for the top left corner of observing rectangle 210 may be calculated as follows:

$x$-axis coordinate=$O_x$−(width/2)/(cos(tan$^{-1}$(3/2))*cos(tan$^{-1}$(3/2)+$\Theta$));      a $y$-axis coordinate=$O_y$−(length/2)/(sin(tan$^{-1}$(3/2))*sin(tan$^{-1}$(3/2)+$\Theta$).      b The coordinates for the top right corner of observing rectangle 210 may be calculated as follows:

$x$-axis coordinate=$O_x$+(width/2)/(cos(tan$^{-1}$(3/2))*cos(tan$^{-1}$(3/2)−$\Theta$));      a $y$-axis coordinate=$O_y$−(length/2)/(sin(tan$^{-1}$(3/2))*sin(tan$^{-1}$(3/2)−$\Theta$).      b The coordinates for the bottom left corner of observing rectangle 210 may be calculated as follows:

$x$-axis coordinate=$O_x$−(width/2)/(cos(tan$^{-1}$(3/2))*cos(tan$^{-1}$(3/2)−$\Theta$));      a $y$-axis coordinate=$O_y$+(length/2)/(sin(tan$^{-1}$(3/2))*sin(tan$^{-1}$(3/2)−$\Theta$).      b The coordinates for the bottom right corner of observing rectangle 210 may be calculated as follows:

$x$-axis coordinate=$O_x$+(width/2)/(cos(tan$^{-1}$(3/2))*cos(tan$^{-1}$(3/2)+$\Theta$));      a $y$-axis coordinate=$O_y$+(length/2)/(sin(tan$^{-1}$(3/2))*sin(tan$^{-1}$(3/2)+$\Theta$).      b Based on the location of each of the corners of observing rectangle 210, lines may be drawn between each corner to render a rectangle. The lines may then form the border of observing rectangle 210. Image analysis unit 60 may determine which pixels lie within observing rectangle 210 and which pixels are outside observing rectangle 210 based on the line equation the defines the border. Image analysis unit 60 may input the coordinates for each pixel into each line equation defining the border. Based on the sign that results from the equation, image analysis unit 60 may determine whether the pixel is within observing rectangle 210. For example, if the result of the line equation is positive, the pixel falls within observing rectangle 210. If the result of the line equation is negative, the pixel falls outside observing rectangle 210.

As described above, image processing device 52 may determine lead orientation. Lead orientation generally refers to determining which electrodes belong to which implanted leads. One example technique for determining which electrodes belong to which implanted leads comprises a regression fit techniques, as described above. In accordance with the regression fit technique, the center points of the bounding rectangles associated with the electrodes may be fitted with a line or a curve using regression fit techniques. The center points may be determined by pixel coordinates associated with pixels forming the blobs that define the respective electrodes. A group of electrodes with a regression fit that has a sufficiently low error may be considered to belong together and to a particular lead carrying the electrodes. An exemplary regression technique may be applied to straight lines or to polynomial curves.

Another example technique for determining which electrodes belong to which implanted leads comprises a triplet fit algorithm. As described earlier, image processing device 52 may determine the center coordinates of each electrode displayed on the image. Alternatively, the user may provide center coordinates of each electrode displayed on the image. Furthermore, as described earlier, image processing device 52 may assign each blob, i.e., electrode, a blob assignment value, which identifies the particular blob in which a pixel resides. For example, the first blob may be identified as blob 1, the second blob may be identified as blob 2, and so on.

In accordance with the triplet fit algorithm, image analysis unit 60 within image processing device 52 may initially calculate the distances between each of the blobs. For example, assume that six blobs, i.e., electrodes, are displayed on the image. The six blobs may be assigned blob values of blob 1 to blob 6. Notably, blob 1 to blob 6 may belong to different leads. Image analysis unit 60 may calculate the distances between each of the blobs. For example, image analysis unit 60 may calculate the distance between blob 1 to blob 2, blob 1 to blob 3, blob 1 to blob 4, blob 1 to blob 5, and blob 1 to blob 6. Similarly, image analysis unit 60 may calculate the distance between blob 2 to blob 3, blob 2 to blob 4, blob 2 to blob 5, and blob 2 to blob 6. Similarly, image analysis unit 60 may calculate the distance between blob 3 and all other blobs, blob 4 and all other blobs, blob 5 and all other blobs, and blob 6 and all other blobs. Image processing device 52 may store the distances between each of the blobs.

Figure 24:
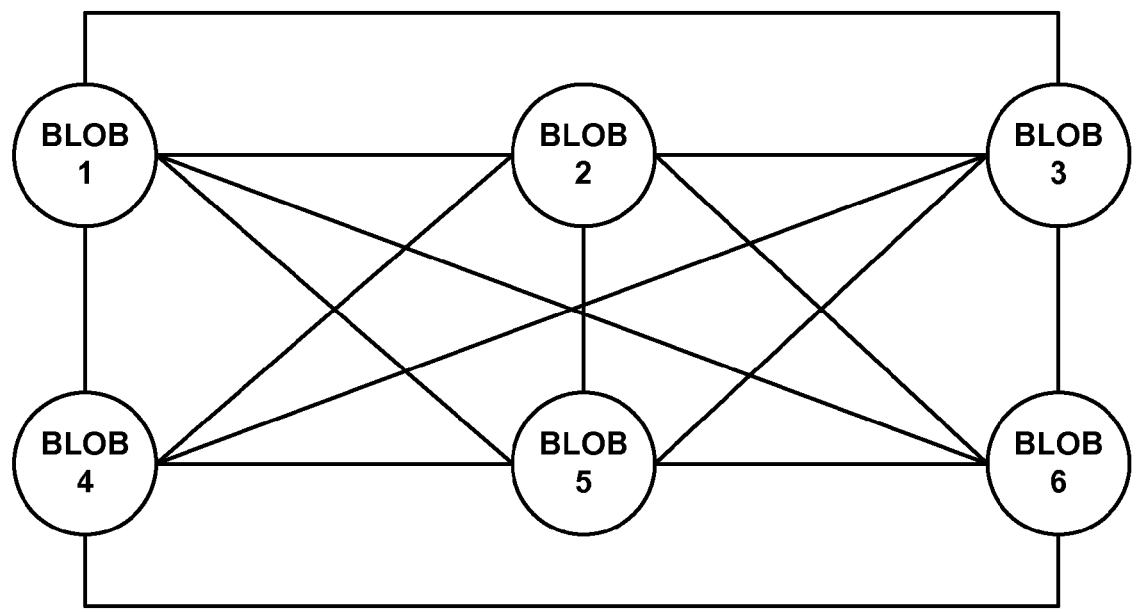
FIG. 24 is an example graphical representation of distances between each of various blobs that represent electrodes.

FIG. 24 is an example graphical representation of the distances between each of the blobs. Image analysis unit 60 may calculate the distances between the respective blobs based on a Pythagorean Theorem, according to one aspect. In this aspect, the distances between two blobs, e.g., blob 1 and blob 2, may be calculated by subtracting and squaring the difference between the x-axis coordinates for blob 1 and blob 2, subtracting and squaring the difference between the y-axis coordinates for blob 1 and blob 2, summing the two squared terms, and taking the square root to find the distance between blob 1 and blob 2. Blobs 1 to 6 are provided merely for illustration purposes. In some examples there may be more or fewer blobs. The coordinates for blob 1 and blob 2 may be the center coordinates for blob 1 and blob 2.

In accordance with the triplet algorithm, image analysis unit 60 may identify groups of at least three blobs, i.e., electrodes, where the distance between a first blob and a second blob of the at least three blobs is substantially the same as the distance between the second blob and a third blob of the at least three blobs. For example, the distances maybe within a threshold percentage of being the same, e.g., 1%, though other percentages are also contemplated by this disclosure. For example, the distance between blob 1 and blob 2 may be substantially the same as the distance between blob 2 and blob 3. Accordingly, image analysis unit 60 may identify blobs 1, 2, and 3 as a first group. Similarly, the distance between blob 2 and blob 3 may be substantially the same as the distance between blob 3 and blob 4. Image analysis unit 60 may identify blobs 2, 3, and 4 as a second group. In some examples, the number of blobs within a group, e.g., three, may be less than the minimum number of electrodes on the known lead types. For example, as shown in FIG. 6, leads 72, 74, 76, 78, 80, and 82 each comprise either 4 electrodes (quads) or 8 electrodes (octads). Each of the groups may comprise fewer blobs than four or eight, e.g., three.

In accordance with the triplet algorithm, image analysis unit 60 may start at a first blob, e.g., blob 1. Image analysis unit 60 may then identify a second blob that the first blob points to. For example, as shown in FIG. 24, blob 1 points to blobs 2 through 6. Image analysis unit 60 may select one of the blobs that the first blob points to and select that as a second blob. The second blob may be one of blobs 2 through 6. Image analysis unit 60 may then determine the distance between the first blob and the second blob. Image analysis unit 60 may then identify a third blob that the second blob points to. For example, if the second blob is selected as blob 2, blob 2 points to blobs 3 through 6 as shown in FIG. 24. The third blob may be blob 3, as one example. Image analysis unit 60 may then determine the distance between the second blob and third blob. Next, image analysis unit 60 may determine whether the distance from the first blob (currently selected as blob 1) to the second blob (currently selected as blob 2) is substantially the same as the distance between the second blob and the third blob (currently selected as blob 3).

If the distance between the first blob and the second blob is substantially the same as the distance between the second blob and third blob, image analysis unit 60 may identify the first, second, and third blobs as a group of blobs (e.g., a triplet). If the distance between the first blob and the second blob is not substantially the same as the distance between the second blob and the third blob, image analysis unit 60 may not identify the first, second and third blobs as a group of blobs. If image analysis unit 60 determines that the distance between the first blob and second blob is not substantially the same as the distance between the second blob and the third blob, image analysis unit 60 may select a different blob for the third blob. For example, image analysis unit 60 may select the third blob as blob 4 since blob 2 also points to blob 4.

Image analysis unit 60 may then determine whether the distance between the first blob (e.g., blob 1) and the second blob (e.g., blob 2) is substantially the same as the distance between the second blob and the newly selected third blob (e.g., blob 4). If the distances are substantially the same, image analysis unit 60 may identify the first, second, and the newly selected third blobs as a group of blobs. If the distances are different, image analysis unit 60 may not identify the first, second, and the newly selected third blobs as a group of blobs. Image analysis unit 60 may compare distances for all possible triplets (each comprising three blobs) to identify groups of blobs. Stated another way, image analysis unit 60 may compare distances for all permutations and combinations of possible triplets of blobs to identify groups of blobs. In some examples, to increase the speed of the triplet algorithm, image analysis unit 60 may only compare distances for all combinations, but not all permutations.

Figure 25:
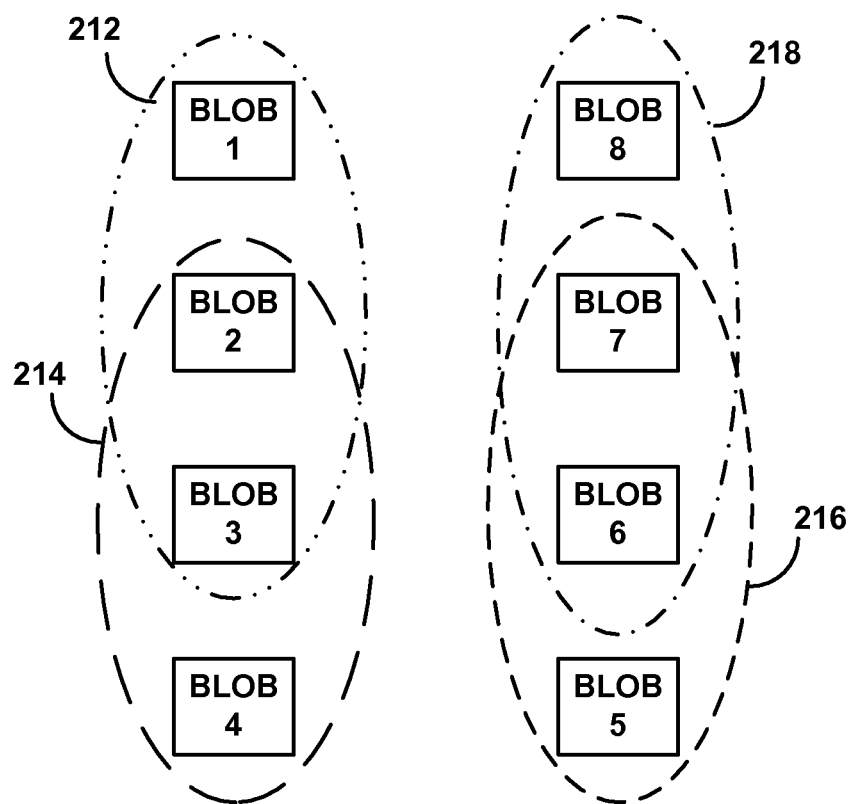
FIG. 25 is a first example of groups of blobs identified by the image analysis unit shown, for example, in FIG. 5B.

FIG. 25 is a first example of groups of blobs identified by the image analysis unit shown 60, for example, in FIG. 5B. In FIG. 25, it is assumed that the distance between blob 1 and blob 2 is substantially the same as the distance between blob 2 and blob 3. Image analysis unit 60 may identify blobs 1, 2, and 3 as group of blobs 212. Blob 1 may be considered as pointing to blob 2, and blob 2 may be considered as pointing to blob 3. In addition, image analysis unit 60 may determine that the distance between blob 2 and blob 3 is substantially the same as the distance between blob 3 and blob 4. Image analysis unit 60 may therefore identify blobs 2, 3, and 4 as group of blobs 214. Blob 3 may be considered as pointing to blob 4.

Additionally, the distance between blob 5 and blob 6 may be determined to be substantially the same as the distance between blob 6 and blob 7. Image analysis unit 60 may identify blobs 5, 6, and 7 as group of blobs 216. Blob 5 may be considered as pointing to blob 6, and blob 6 may be considered as pointing to blob 7. In FIG. 25, the distance between blob 6 and blob 7 is substantially the same as the distance between blob 7 and blob 8. Blob 7 may be considered as pointing to blob 8. Image analysis unit 60 may identify blobs 6, 7, and 8 as group of blobs 218.

As one example, since the distance between blob 1 and blob 2 is substantially the same as the distance between blob 2 and blob 3, image analysis unit 60 may determine that blobs 1, 2, and 3 represent electrodes on the same lead. Similarly, since the distance between blob 2 and blob 3 is substantially the same as the distance between blob 3 and blob 4, image analysis unit 60 may determine that blobs 2, 3, and 4 represent electrodes on the same lead. Since the distance between blob 5 and blob 6 is substantially the same as the distance between blob 6 and blob 7, image analysis unit 60 may determine that blobs 5, 6, and 7 represent electrodes on the same lead. And, since the distance between blob 6 and 7 is substantially the same as the distance between blob 7 and blob 8, image analysis unit 60 may determine that blobs 6, 7, and 8 represent electrodes that on the same lead.

After identifying the groups of blobs, e.g., groups of blobs 212, 214, 216, and 218, image analysis unit 60 may determine which groups have at least two blobs that overlap with those included in another group. For example, as shown in FIG. 25, group of blobs 212 and 214 both include blobs 2 and 3. Similarly, as shown in FIG. 25, group of blobs 216 and 218 both include blobs 6 and 7. Since group of blobs 212 and 214 both include blobs 2 and 3, the distance between blob 1 and 2 is substantially the same as the distance between blob 2 and blob 3, which is substantially the same distance between blob 3 and blob 4. Image analysis unit 60 may therefore determine that blobs 1, 2, 3, and 4 represent electrodes that belong to the same lead. Similarly, image analysis unit 60 may determine that blobs 5, 6, 7, and 8 represent electrodes that belong to the same lead. Moreover, since there is no overlap between blobs 1, 2, 3, and 4 and blobs 5, 6, 7, and 8, image analysis unit 60 may determine that blobs 1, 2, 3, and 4 belong to a first lead, and blobs 5, 6, 7, and 8 belong to a second lead.

Image analysis unit 60 may likewise analyze groups of blobs to find at least two overlapping blobs. Image analysis unit 60 may determine that groups of blobs with at least two overlapping blobs belong to the same lead. However, as seen in Table 1 and FIG. 6, leads 72, 74, 76, and 78 each comprise either 4 electrodes (quads) or 8 electrodes (octads). Accordingly, image analysis unit 60 may, in some instances, identify quads or octads that belong to the same lead and discard all other possible options. Notably, in examples where leads comprise more or fewer than 4 or 8 electrodes, image analysis unit 60 may determine all possible blobs that belong to the same lead.

In some examples, merely relying on distances to determine which blobs represent electrodes that belong to the same lead may result incorrect identification of a lead. For example, as shown in FIG. 25, blobs 1, 2, 3, and 4 are clearly separate from blobs 5, 6, 7, and 8. However, due to the curvature of the patient's spine, as one example, or due to lead migration, as another example, the implanted leads may curve. The distances between blobs of two different leads may, in these types of exemplary cases, become substantially the same as the distances between blobs on the same lead. Accordingly, it may be possible for image analysis unit 60 to incorrectly determine that the two blobs from different leads represent electrodes on the same lead. As described below, to avoid incorrectly determining that blobs from two different leads represent electrodes on the same lead, image analysis unit 60 may, in some instances, utilize slopes between electrodes to build confidence that the identified blobs belong to the same lead.

Figure 26:
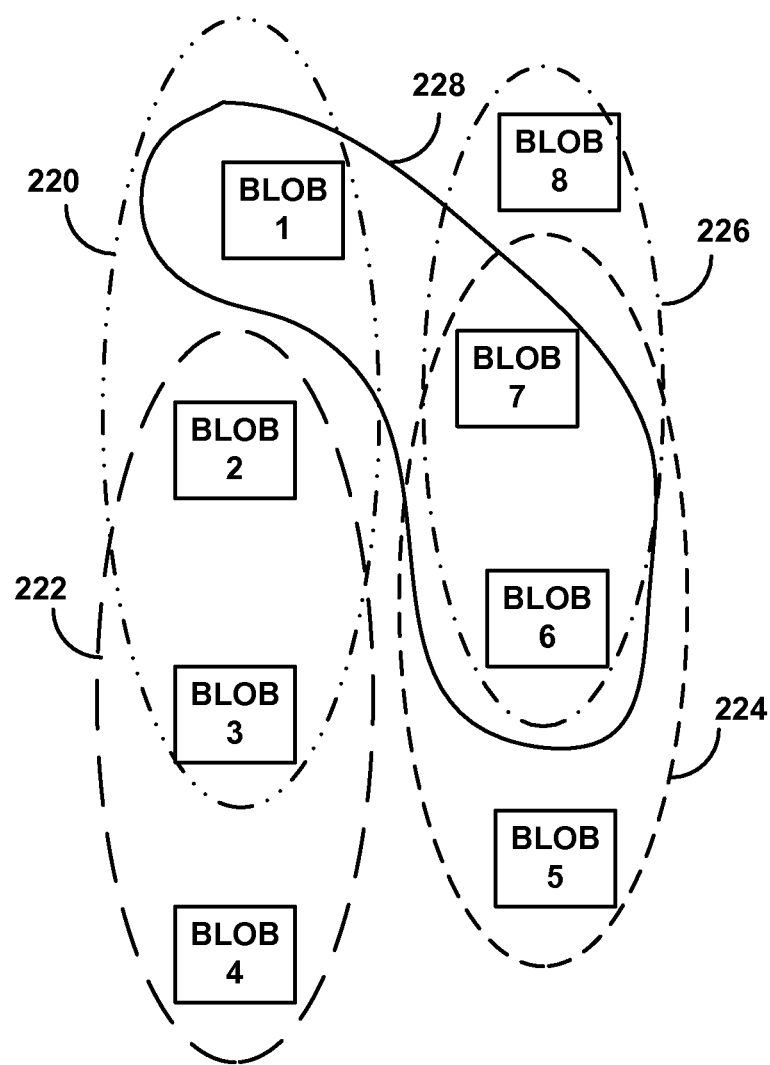
FIG. 26 is a second example of groups of blobs identified by the image analysis unit shown, for example, in FIG. 5B.

FIG. 26 is a second example of groups of blobs identified by the image analysis unit 60 shown, for example, in FIG. 5B. FIG. 26 is not drawn to scale. As seen in FIG. 26, image analysis 60 identified groups of blobs 220, 222, 224, 226, and 228. Similar to FIG. 25, the distance between blob 1 and 2 is substantially the same as distance between blob 2 and 3, and therefore image analysis unit 60 may identify blobs 1, 2, and 3 as group of blobs 220. The distance between blob 2 and 3 is substantially the same as the distance between blob 3 and 4 in the example of FIG. 26, and image analysis unit 60 may identify blobs 2, 3, and 4 as group of blobs 222. The distance between blob 5 and 6 is substantially the same as the distance between blob 6 and 7, and image analysis unit 60 may identify blobs 5, 6, and 7 as group of blobs 224. The distance between blob 6 and 7 is substantially the same as the distance between blob 7 and blob 8, and image analysis unit 60 may identify blobs 6, 7, and 8 as group of blobs 226.

However, the distance between blob 6 and 7 is also substantially the same distance between blob 7 and 1. In this case, image analysis unit 60 may identify blobs 6, 7, and 1 as group 228. Similar to FIG. 25, image analysis unit 60 may determine which groups have at least two blobs that overlap another group. Based on the determination, image analysis unit 60 may determine which blobs belong to the same lead. As shown in FIG. 26, relying solely on distances, image analysis unit 60 may determine that blobs 1, 2, 3, and 4 represent electrodes that belong to a first lead. In the first lead, blob 1 points to blob 2, blob 2 points to blob 3, and blob 3 points to blob 4. Image analysis unit 60 may also determine that blobs 5, 6, 7, and 8 represent electrodes that belong to a second lead. In the second lead, blob 5 points to blob 6, blob 6 points to blob 7, and blob 7 points to blob 8.

Furthermore, in the example of FIG. 26, image analysis unit 60 may also incorrectly determine that blobs 5, 6, 7, and 1 belong to a third lead. In the third lead, blob 5 points to blob 6, blob 6 points to blob 7, and blob 7 points to blob 1.

Clearly, blobs 5, 6, 7 cannot represent electrodes on both the second lead and the third lead. Similarly, blob 1 cannot represent an electrode on both the first lead and the third lead. In accordance with the triplet algorithm, in addition to distances between blobs, image analysis unit 60 may utilize the slopes between blobs to determine which blobs belong to which leads.

Though the leads may curve due to the patient's posture or migration, the leads may be stiff enough to only allow a certain curve threshold. Due to the stiffness of the leads, the leads may be somewhat limited in their ability to bend. Image analysis unit 60 may calculate the slope between electrodes. Image analysis unit 60 may then determine which blobs belong to which leads based on the slope. Image analysis unit 60 may calculate the slopes between two consecutive blobs identified to be on the same lead.

For example, image analysis unit 60 determined that blobs 1, 2, 3, and 4 represent electrodes that belong to the first lead. Image analysis unit 60 may calculate the slopes between a blob and the blob that it points to (e.g., the slope between blob 1 and blob 2, the slope between blob 2 and blob 3, and the slope between blob 3 and 4). However, image analysis unit 60 may not calculate the slopes between blob 1 and blob 3, blob 1 and blob 4, or blob 2 and blob 4, in one embodiment, since blob 1 does not point to blob 3 or blob 4, and blob 2 does not point to blob 4.

Notably, as shown in FIG. 26, blobs 1 through 8 are generally aligned vertically. To avoid a possible divide by zero problem in calculating the slopes between blobs, in some examples, the slope may be defined as the change in the x-axis coordinates between the two blobs divided by the change in the y-axis coordinates between the two blobs However, in examples where the blobs are aligned horizontally, the slope may be defined as the change in the y-axis coordinates between the two blobs divided by the change in the x-axis coordinates between the two blobs.

After determining the slopes between blobs, in one example, image analysis unit 60 may compare the slopes to a curve threshold. If the slope between any of the blobs is greater than the curve threshold, image analysis unit 60 may determine that those blobs do not belong to the same lead. If the slope between any of the blobs is less than the curve threshold, image analysis unit 60 may confirm that those blobs belong to the same lead.

In an alternate example, instead of calculating the slopes between blobs and the blobs that they point to, image analysis unit 60 may only calculate the slopes for blobs that have been identified for two or more leads. For example, as shown in FIG. 26 and described above, image analysis unit 60 may identify the second lead as including blobs 5, 6, 7, and 8. Image analysis unit 60 may also identify the third lead as including blobs 5, 6, 7, and 1. As noted above, for the second lead, blob 7 points to blob 8 and for the third lead blob 7 points to blob 1. Image analysis unit 60 may only determine the slope between blob 7 and blob 8 and the slope between blob 7 and blob 1. In one example, image analysis unit 60 may compare the slope between blob 7 and blob 8 to the slope between blob 7 and blob 1 to the curve threshold. Image analysis unit 60 may determine which of the slopes is smaller. For example, as seen in FIG. 26, the slope between blob 7 and blob 8 is less than the slope between blob 7 and blob 1. Image analysis unit 60 may determine that the slopes for blobs that results in the lower slope value represent electrodes that belong to the same lead.

For example, since the slope between blob 7 and blob 8 is less than the slope between blob 7 and blob 1, image analysis unit 60 may determine that blob 7 and blob 8 belong to the same lead, and blob 7 and blob 1 belong to different leads. Image analysis unit 60 may discard the third lead as a possible lead configuration, after determining that blob 7 and blob 1 belong to different leads.

After identifying possible leads, image analysis unit 60 may extract geometries of the leads. For example, as shown in FIGS. 25A and 25B, image analysis unit 60 identified two leads, the first lead and the second lead. The first lead comprises blobs 1 through 4 and the second lead comprises blobs 5 through 8. Furthermore, the width of each of the blobs is also known based on the size estimation technique described above. Image analysis unit 60 may calculate the ratio between electrode spacing and the electrode width. For example, the electrode width may be divided by the distance between blob 1 and blob 2.

Notably, the distance between blob 1 and blob 2 is the distance between the center of blob 1 to the center of blob 2. However, as shown in FIG. 6 and Table 1, the electrode spacing is defined as the distance between the ends of the electrodes. Table 3 provides the center-to-center distances and the width to center-to-center ratios for leads 72, 74, 76, 78, 80, and 82.

between the electrode width and the electrode spacing will be 6 pixels divided by 72 pixels, which is 0.083333. Image analysis unit 60 may provide the ratio to characterization unit 62. Characterization unit 62 may compare the ratio provided by image analysis unit 60 to known ratios for known lead types. In this example, characterization unit 62 may receive the ratio for the first lead as 0.083333. Characterization unit 62 may determine that the first lead is lead 72 since the ratio of electrode width to electrode spacing for lead 72 is also 0.083333. As described above, lead 72 is the Quad Plus lead type. Accordingly, characterization unit 62 may determine that the first lead is the Quad Plus lead. Image analysis unit 60 and characterization unit 62 may also determine the lead type for the second lead based on similar techniques.

Similar to the above description, once the lead types are known, image processing device 52 may calculate pixel dimensions. For example, first lead is determined to be Quad Plus lead. The center-to-center electrode spacing for Quad Plus lead is 18 mm. The center-to-center electrode spacing for the first lead is 72 pixels. Therefore the pixel dimension for each pixel may be 0.25 mm, e.g., 18 mm divided by 72. As described above, after pixel dimensions are calculated, the spacing between leads may be calculated. The spacing between leads may be utilized to update or modify the therapy program.

Figure 27:
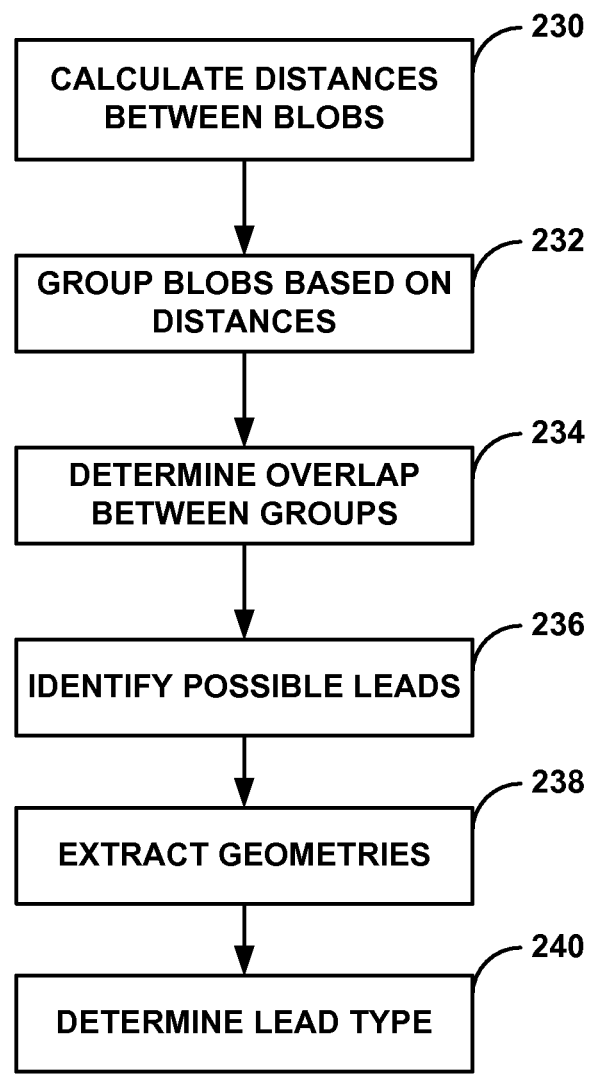
FIG. 27 is a flow chart illustrating an example operation of the triplet algorithm that may be implemented to determine which electrodes belong to which leads.

FIG. 27 is a flow chart illustrating an example operation of the triplet algorithm described above. For purposes of illustration, reference will be made to FIG. 5B with respect to the flow chart shown in FIG. 27.

As shown in FIG. 27, image analysis unit 60 may calculate the distances between blobs, i.e. electrodes contained within an electronic image, e.g., FIG. 11B (230). Image analysis unit 60 may then identify groups of blobs based on the calculated distances that each include a plurality of electrode images within the electronic image (232). Image analysis unit 60 may identify triplets of blobs where the distance from a first blob of a triplet to a second blob of the triplet is substantially the same as the distance between the second blob of the triplet to a third blob of the triplet. Stated another way, one of the blobs within the triplets of blobs is substantially equidistant from the other two blobs within the triplet of blobs, i.e., within a threshold percentage of being equidistant, e.g., 1%, though other percentages are also contemplated by this disclosure. Image analysis unit 60 may then determine overlap between the groups of blobs (234). Image analysis unit 60 may analyze groups of blobs to find at least two overlapping blobs. Image

TABLE 3

| | Lead Number | | | | | |
|---|---|---|---|---|---|---|
| | 72 | 74 | 76 | 78 | 80 | 82 |
| Electrode Width (mm) | 1.5 | 1.5 | 1.5 | 1.5 | 1.5 | 1.5 |
| Electrode Length (mm) | 6 | 3 | 2.5 | 3 | 3 | 3 |
| Electrode Spacing (center-to-center) (mm) | 18 | 9 | 7.5 | 4.5 | 7 | 9 |
| Number of Electrodes | 4 | 4 | 4 | 8 | 8 | 8 |
| Ratio of Electrode Width to Electrode Center-to-Center Spacing | 1.5/18 = 0.08333 | 1.5/9 = 0.16666 | 1.5/7.5 = 0.2 | 1.5/4.5 = 0.3333 | 1.5/7 = 0.2143 | 1.5/9 = 0.16666 |

As described above, image analysis unit 60 may compare the ratio between the electrode width and the distance between blob 1 and blob 2 to the ratios provided in Table 3. For example, if the electrode width for blob 1 is 6 pixels and the distance between blob 1 and blob 2 is 72 pixels, the ratio analysis unit 60 may determine that the identified groups of blobs with at least two overlapping blobs belong to the same lead (236). Stated another way, image analysis unit 60 may identify one or more leads based on the identified groups of blobs with at least two overlapping blobs.

As shown in FIG. 6, as one example, leads 72, 74, 76, 78, 80, and 82 comprise either four electrodes or eight electrodes. Image analysis unit 60 may identify possible leads that comprise either four electrodes or eight electrodes. Furthermore, in some examples, image analysis unit 60 may calculate slopes between one electrode and an electrode that it points to. In one example, image analysis unit 60 may compare the slope to a curve threshold. If the slope is greater than the curve threshold, image analysis unit 60 may determine that the lead configuration was identified incorrectly. If the slope is less than the curve threshold, image analysis unit 60 may confirm that the electrodes belong to the same lead. In another example, image analysis unit 60 may only compare slopes between electrodes identified to be on at least two different leads. Image analysis unit 60 may determine that the electrodes that produce the lower slope belong to the same lead, and that the electrodes that produce the greater slope do not belong to the same lead.

Image analysis unit 60 may then extract lead geometries (238). As one example, the lead geometries may comprise a ratio between the width of an electrode and the center-to-center spacing between an adjacent electrode that belongs to the same lead. For example, referring back to FIG. 25, the electrode width for blob 1 may be 6 pixels and the distance between blob 1 and blob 2 may be 72 pixels. The ratio between the width of blob 1 and the center-to-center spacing between blob 1 and blob 2 may be 0.08333.

Characterization unit 62 may receive the extracted geometries and determine the lead type (240). Characterization unit 62 may compare the extracted geometries to extracted geometries for known lead types. Based on the comparison, characterization unit 62 may determine the lead type. For example, the extracted geometry for a first lead may be 0.08333. As shown in Table 3, lead 72 comprises an extracted geometry of 0.08333. As described above, lead 72 may be the Quad Plus lead. Accordingly, characterization unit 62 may determine that the first lead is the Quad Plus lead.

For purposes of illustration only, the triplet algorithm has been described above to identify leads and lead types. However, other aspects of this disclosure are not so limited. For example, in some instances, a doublet algorithm may be used instead of a triplet algorithm. The doublet algorithm may be substantially similar to the triplet algorithm. In accordance with the doublet algorithm, image analysis unit 60 may compare all distances between blobs, i.e., electrodes, and find distances that are substantially the same. For example, referring to FIG. 25, image analysis unit 60 may determine that the distance between blob 1 and blob 2 is substantially the same as the distance between blob 2 and blob 3, which is also substantially the same distance between blob 3 and blob 4. As another example, image analysis unit 60 may determine that the distance between blob 1 and blob 3 is substantially the same as the distance between blob 2 and blob 4. As yet another example, referring to FIG. 26, image analysis unit 60 may determine that the distance between blob 5 and blob 6 is substantially the same as the distance between blob 6 and blob 7, which is substantially the same as the distance between blob 7 and the distance between blob 8 and blob 7 and blob 1.

When utilizing the doublet algorithm, image analysis unit 60 may generate groups of doublets. For example, referring to FIG. 25, a first group may comprise of blob 1 and blob 2, a second group may comprise of blob 2 and blob 3, a third group may comprise blob 1 and blob 3, a fourth group may comprise blob 2 and blob 4, and so on. Image analysis unit 60 may then compare the groups to determine which groups have an overlap of at least one blob. For example, image analysis unit 60 may determine that the first group and the second group both comprise blob 2, and that the first group and the third group both comprise blob 1.

Image analysis unit 60 may then identify groups that have at least one common blob as groups of blobs that belong to the same lead. For example, image analysis unit 60 may determine that blobs 1, 2, and 3 belong to the same lead because the first group and the second group both include blob 2. Accordingly, image analysis unit 60 may identify possible leads based on groups that include at least one common blob.

Image analysis unit 60 may then calculate the slopes between the blobs for each group. For example, image analysis unit 60 may calculate the slopes between blob 1 and blob 2, blob 2 and blob 3, and so on. If the slope for a group of doublets (i.e., two blobs) is less than the defined curve threshold, then image analysis unit 60 may determine that blobs belonging to that group may belong to the same lead. If the slope of a group of doublets is greater than the curve threshold, then image analysis unit 60 may determine that the blobs belonging to that group may not belong to the same lead.

Based on the overlap of blobs between groups of doublets and the slopes between blobs that are less than the curve threshold, image analysis unit 60 may identify leads. After identifying leads, image analysis unit 60 may extract geometries as described above. For example, image analysis unit 60 may calculate the ratio between the width of the blob and spacing between blobs on the same lead. The extracted geometries may then be provided to characterization unit 62. Characterization unit 62 may identify the lead types for each identified lead based on the extracted geometries as described above.

To reiterate, image analysis unit 60 may utilize a doublet algorithm or a triplet algorithm to identify leads on an electronic image of blobs, i.e., electrode images. However, image analysis unit 60 may group the blobs in more than doubles or triples. For example, image analysis unit 60 may group the blobs in quadruples or quintuples. Generally, image analysis unit 60 may group any plurality of blobs, i.e., electrode images, to identify leads. In some examples, the number of blobs within each group may be less than the minimum number of electrodes on known lead types. For example, the number of blobs within each group may be less than the number of electrodes on leads 72, 74, 76, 78, 80, and 82 (FIG. 6).

The techniques described in this disclosure, including those attributed to image processing device 52, programmer 20, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The techniques described in this disclosure can be applied for electrode array characterization and visualization, and stimulation parameter adjusting and programming, for electrical stimulation systems applicable to any of a wide variety of symptoms or conditions such as chronic pain, tremor, Parkinson's disease, epilepsy, urinary or fecal incontinence, sexual dysfunction, obesity, or gastroparesis. For example, the techniques may be applied to implantable medical devices configured to deliver neurostimulation or other electrical stimulation therapy via implanted electrode arrays, carried by leads or otherwise, located proximate to the spinal cord, pelvic nerves, peripheral nerves, the stomach or other gastrointestinal organs, or within the brain of a patient.

Many embodiments of the invention have been described. Various modifications may be made without departing from the scope of the claims. These and other embodiments are within the scope of the following claims.

The invention claimed is:

1. A method comprising:
   obtaining an analysis of a first electronic image of a plurality of electrical stimulation leads implanted within a patient relative to a second electronic image of the plurality of electrical stimulation leads, wherein the first electronic image is obtained at a first time and the second electronic image is obtained at a second time, wherein each one of the plurality of leads includes one or more electrodes, and wherein the analysis comprises a comparison of locations of electrodes in the first electronic image to locations of electrodes in the second electronic image;
   determining a configuration of the leads based on the analysis; and
   automatically generating an adjustment to electrical stimulation therapy delivered via at least one of the leads based on the configuration of the leads.

2. The method of claim 1, wherein the adjustment includes an adjustment of one or more parameters associated with the electrical stimulation therapy delivered via at least one of the leads.

3. The method of claim 1, wherein the adjustment includes an adjustment of one or more electrode combinations associated with the electrical stimulation therapy delivered via at least one of the leads.

4. The method of claim 1, wherein the configuration includes types of at least some of the leads, orientations of at least some the leads within the patient, and relative positions of at least some of the electrodes on at least one of the leads relative to some of the electrodes on at least one other lead of the plurality of leads.

5. The method of claim 4, wherein the configuration further includes at least one of a shape and surface area of at least some of the electrodes.

6. The method of claim 1, further comprising automatically generating an indication of lead migration based on a difference between the first and second images.

7. The method of claim 1, further comprising:
   analyzing a third electronic image of an electrical stimulation lead implanted within the patient when the patient is in a first posture, wherein the first posture is same or different than a posture of the patient when the first and second electronic images were taken;
   analyzing a fourth electronic image of an electrical stimulation lead implanted within the patient when the patient is in a second posture different from the first posture;
   automatically generating adjustments to electrical stimulation therapy configured for delivery via the lead when the patient is in the first posture based on the analysis of the third image; and
   automatically generating adjustments to electrical stimulation therapy configured for delivery via the lead when the patient is in the second posture based on the analysis of the fourth image.

8. The method of claim 1, further comprising:
   determining a relationship of at least some of the electrodes relative to one or more anatomical structures within the patient based on the analysis
   wherein automatically generating an adjustment to electrical stimulation therapy comprises automatically generating the adjustment to the electrical stimulation therapy delivered via at least one of the leads based further on the analysis and the determined relationship.

9. The method of claim 1, wherein automatically generating an adjustment comprises automatically generating an initial setting of one or more electrical stimulation therapy parameters.

10. The method of claim 1, wherein automatically generating an adjustment comprises automatically modifying one or more existing electrical stimulation therapy parameters.

11. The method of claim 1, further comprising automatically applying the adjustment to electrical stimulation therapy delivered via at least one of the leads.

12. The method of claim 1, further comprising applying the adjustment upon user approval.

13. The method of claim 1, further comprising automatically generating a programming search sequence for electrode combinations for delivery of electrical stimulation therapy based on the analysis, wherein automatically generating an adjustment to electrical stimulation therapy comprises automatically generating the adjustment to electrical stimulation therapy based further on the generated programming search sequence.

14. The method of claim 1, further comprising automatically inhibiting selection of particular electrode combinations for delivery of electrical stimulation therapy based on the analysis, wherein automatically generating an adjustment to electrical stimulation therapy comprises automatically generating the adjustment to electrical stimulation therapy based further on the inhibited selection of particular electrode combinations.

15. The method of claim 1, further comprising determining one or more inter-electrode distances based upon the analysis, and wherein automatically generating an adjustment to electrical stimulation therapy delivered via at least one of the leads comprises automatically generating an adjustment to electrical stimulation therapy delivered via at least one of the leads based further on the one or more inter-electrode distances.

16. The method of claim 1, further comprising determining one or more electrode sizes based upon the analysis, and wherein automatically generating an adjustment to electrical stimulation therapy delivered via at least one of the leads comprises automatically generating an adjustment to electrical stimulation therapy delivered via at least one of the leads based further on the one or more electrode sizes.

17. The method of claim 1, further comprising determining one or more inter-electrode sizes based upon the analysis, and wherein automatically generating an adjustment to electrical stimulation therapy delivered via at least one of the leads comprises automatically generating an adjustment to electrical stimulation therapy delivered via at least one of the leads based further on the one or more inter-electrode sizes.

18. The method of claim 1, wherein automatically generating the adjustment comprises at least one of automatically setting initial one or more electrical stimulation therapy parameters based on the configuration of the leads, and automatically modifying one or more existing electrical stimulation therapy parameters based on the configuration of the leads.

19. A device comprising:
an image analysis interface configured to obtain an analysis of a first electronic image of a plurality of electrical stimulation leads implanted within a patient relative to a second electronic image of the plurality of electrical stimulation leads and obtain a configuration of the plurality of leads based on the analysis, wherein the first electronic image is obtained at a first time and the second electronic image is obtained at a second time, wherein each one of the plurality of leads includes one or more electrodes, and wherein the analysis comprises a comparison of locations of electrodes in the first electronic image to locations of electrodes in the second electronic image; and
a programming unit configured to automatically generate an adjustment to electrical stimulation therapy delivered via at least one of the leads based on the configuration of the leads.

20. The device of claim 19, wherein the adjustment includes an adjustment of one or more parameters associated with the electrical stimulation therapy delivered via at least one of the leads.

21. The device of claim 19, wherein the adjustment includes an adjustment of one or more electrode combinations associated with the electrical stimulation therapy delivered via at least one of the leads.

22. The device of claim 19, wherein the configuration includes types of at least some of the leads, orientations of at least some the leads within the patient, and relative positions of at least some of the electrodes on at least one of the leads relative to some of the electrodes on at least one other lead of the plurality of leads.

23. The device of claim 22, wherein the configuration further includes at least one of a shape and surface area of at least some of the electrodes.

24. The device of claim 19, wherein the programming unit automatically generates an indication of lead migration based on a difference between the first and second images.

25. The device of claim 19, wherein the image analysis interface is configured to obtain an analysis of a third electronic image of an electrical stimulation lead implanted within the patient when the patient is in a first posture, wherein the first posture is same or different than a posture of the patient when the first and second electronic images were taken, and analysis of a fourth electronic image of an electrical stimulation lead implanted within the patient when the patient is in a second posture different from the first posture, and wherein the programming unit automatically generates adjustments to electrical stimulation therapy configured for delivery via the lead when the patient is in the first posture based on the analysis of the third image, and automatically generates adjustments to electrical stimulation therapy configured for delivery via the lead when the patient is in the second posture based on the analysis of the fourth image.

26. The device of claim 19, wherein the interface obtains a determination of a relationship of at least some of the electrodes relative to one or more anatomical structures within the patient, and the programming unit automatically generates an adjustment to electrical stimulation therapy delivered via at least one of the leads based further on the analysis and the determined relationship.

27. The device of claim 19, wherein automatically generation of an adjustment comprises automatically generation of an initial setting of one or more electrical stimulation therapy parameters.

28. The device of claim 19, wherein automatically generation of an adjustment comprises automatic modification of one or more existing electrical stimulation therapy parameters.

29. The device of claim 19, wherein the programming unit automatically applies the adjustment to electrical stimulation therapy delivered via at least one of the leads.

30. The device of claim 19, wherein the programming unit applies the adjustment upon user approval.

31. The device of claim 19, wherein the programming unit automatically generates a programming search sequence for electrode combinations for delivery of electrical stimulation therapy based on the analysis, wherein the programming unit automatically generates an adjustment to electrical therapy based further on the generated programming search sequence.

32. The device of claim 19, where in the programming unit automatically inhibits selection of particular electrode combinations for delivery of electrical stimulation therapy based on the analysis, wherein the programming unit automatically generating an adjustment to electrical stimulation therapy based further on the inhibited selection of particular electrode combinations.

33. The device of claim 19, wherein the programming unit determines one or more inter-electrode distances based upon the analysis, and wherein the programming unit automatically generates an adjustment to electrical stimulation therapy delivered via at least one of the leads based further on the one or more inter-electrode distances.

34. The device of claim 19, wherein the programming unit determines one or more electrode sizes based upon the analysis, and wherein the programming unit automatically generates an adjustment to electrical stimulation therapy delivered via at least one of the leads based further on the one or more electrode sizes.

35. The device of claim 19, wherein the programming unit determines one or more inter-electrode sizes based upon the analysis, and wherein the programming unit automatically generates an adjustment to electrical stimulation therapy delivered via at least one of the leads based further on the one or more inter-electrode sizes.

36. The device of claim 19, wherein the programming unit automatically sets initial one or more electrical stimulation therapy parameters based on the configuration of the leads to automatically generate the adjustment to the electrical stimulation therapy.

37. The device of claim 19, wherein the programming unit automatically modifies one or more existing electrical stimulation therapy parameters based on the configuration of the leads.

38. A system comprising:
an image capture device configured to obtain a first electronic image, at a first time, of a plurality of electrical stimulation leads implanted within a patient and to obtain a second electronic image, at a second time, of the plurality of electrical stimulation leads implanted within the patient, wherein each one of the plurality of leads includes one or more electrodes;
an image analysis device configured to analyze the first image of the plurality of electrical stimulation leads relative to the second image of the plurality of electrical stimulation leads and determine a configuration of the plurality of leads based on the analysis, wherein the analysis comprises a comparison of locations of electrodes in the first electronic image to locations of electrodes in the second electronic image; and
a programming device configured to automatically generate an adjustment to electrical stimulation therapy delivered by an electrical stimulation device via at least one of the plurality of leads based on the configuration of the leads.

39. The system of claim 38, wherein the adjustment includes an adjustment of one or more parameters associated with the electrical stimulation therapy delivered via at least one of the leads.

40. The system of claim 38, wherein the adjustment includes an adjustment of one or more electrode combinations associated with the electrical stimulation therapy delivered via at least one of the leads.

41. The system of claim 38, wherein the configuration includes types of at least some of the leads, orientations of at least some the leads within the patient, and relative positions of at least some of the electrodes on at least one of the leads relative to some of the electrodes on at least one other lead of the plurality of leads.

42. The system of claim 38, wherein the programming device automatically generates an indication of lead migration based on a difference between the first and second images.

43. The system of claim 38, wherein the analysis device analyzes a third electronic image of an electrical stimulation lead implanted within the patient when the patient is in a first posture, wherein the first posture is same or different than a posture of the patient when the first and second electronic images were taken, and analyzes a fourth electronic image of an electrical stimulation lead implanted within the patient when the patient is in a second posture different from the first posture, and wherein the programming device automatically generates adjustments to electrical stimulation therapy configured for delivery via the lead when the patient is in the first posture based on the analysis of the third image, and automatically generates adjustments to electrical stimulation therapy configured for delivery via the lead when the patient is in the second posture based on the analysis of the fourth image.

44. The system of claim 38, wherein the image analysis device determines a relationship of at least some of the electrodes relative to one or more anatomical structures within the patient, and the programming device automatically generates an adjustment to electrical stimulation therapy delivered via at least one of the leads based further on the analysis and the determined relationship.

45. A system comprising:
means for obtaining an analysis of a first electronic image of a plurality of electrical stimulation leads implanted within a patient relative to a second electronic image of the plurality of electrical stimulation leads, wherein the first electronic image is obtained at a first time and the second electronic image is obtained at a second time, wherein each one of the plurality of leads includes one or more electrodes, and wherein the analysis comprises a comparison of locations of electrodes in the first electronic image to locations of electrodes in the second electronic image;
means for determining a configuration of the plurality of leads based on the analysis; and
means for automatically generating an adjustment to electrical stimulation therapy delivered via at least one of the leads based on the configuration of the leads.

46. The system of claim 45, wherein the adjustment includes an adjustment of one or more parameters associated with the electrical stimulation therapy delivered via at least one of the leads.

47. The system of claim 45, wherein the adjustment includes an adjustment of one or more electrode combinations associated with the electrical stimulation therapy delivered via at least one of the leads.

48. The system of claim 45, wherein the configuration includes types of at least some of the leads, orientations of at least some the leads within the patient, and relative positions of at least some of the electrodes.

49. The system of claim 48, wherein the configuration further includes at least one of a shape and surface area of at least some of the electrodes.

50. The system of claim 45, the system further comprising means for automatically generating an indication of lead migration based on a difference between the first and second images.

51. The system of claim 50, further comprising:
means for analyzing a third electronic image of an electrical stimulation lead implanted within the patient when the patient is in a first posture, wherein the first posture is same or different than a posture of the patient when the first and second electronic images were taken;
means for analyzing a fourth electronic image of an electrical stimulation lead implanted within the patient when the patient is in a second posture different from the first posture;
means for automatically generating adjustments to electrical stimulation therapy configured for delivery via the lead when the patient is in the first posture based on the analysis of the third image; and
means for automatically generating adjustments to electrical stimulation therapy configured for delivery via the lead when the patient is in the second posture based on the analysis of the fourth image.

52. The system of claim 50, further comprising:
means for determining a relationship of at least some of the electrodes relative to one or more anatomical structures within the patient based on the analysis
wherein the means for automatically generating an adjustment to electrical stimulation therapy comprises means for automatically generating the adjustment to electrical stimulation therapy delivered via at least one of the leads based further on the analysis and the determined relationship.

53. A non-transitory computer-readable medium comprising instructions to cause one or more processors to:
- obtain an analysis of a first electronic image of a plurality of electrical stimulation leads implanted within a patient relative to a second electronic image of the plurality of electrical stimulation leads, wherein the first electronic image is obtained at a first time and the second electronic image is obtained at a second time, wherein each one of the plurality of leads includes one or more electrodes, and wherein the analysis comprises a comparison of locations of electrodes in the first electronic image to locations of electrodes in the second electronic image;
- determine a configuration of the leads based on the analysis; and
- automatically generate an adjustment to electrical stimulation therapy delivered via at least one of the leads based on the configuration of the leads.

* * * * *